US008795660B2

(12) United States Patent
Watts et al.

(10) Patent No.: US 8,795,660 B2
(45) Date of Patent: Aug. 5, 2014

(54) NEUROPILIN ANTAGONISTS

(71) Applicant: Genentech, Inc., South San Francisco, CA (US)

(72) Inventors: Ryan J. Watts, San Mateo, CA (US); Yan Wu, Foster City, CA (US)

(73) Assignee: Genentech, Inc., South San Francisco, CA (US)

( * ) Notice: Subject to any disclaimer, the term of this patent is extended or adjusted under 35 U.S.C. 154(b) by 21 days.

(21) Appl. No.: 13/740,080

(22) Filed: Jan. 11, 2013

(65) Prior Publication Data

US 2013/0115214 A1 May 9, 2013

Related U.S. Application Data

(60) Division of application No. 13/489,299, filed on Jun. 5, 2012, now Pat. No. 8,378,080, which is a division of application No. 13/173,890, filed on Jun. 30, 2011, now Pat. No. 8,211,429, which is a division of application No. 12/107,544, filed on Apr. 22, 2008, now Pat. No. 7,994,286, which is a continuation of application No. PCT/US2006/043516, filed on Nov. 8, 2006.

(60) Provisional application No. 60/820,561, filed on Jul. 27, 2006, provisional application No. 60/734,798, filed on Nov. 8, 2005.

(51) Int. Cl.
*A61K 39/395* (2006.01)

(52) U.S. Cl.
USPC .................. 424/130.1; 424/133.1; 424/135.1; 424/136.1; 424/139.1; 424/141.1; 424/155.1

(58) Field of Classification Search
None
See application file for complete search history.

(56) References Cited

U.S. PATENT DOCUMENTS

| | | | |
|---|---|---|---|
| 4,675,187 A | 6/1987 | Konishi et al. | |
| 4,816,567 A | 3/1989 | Cabilly et al. | |
| 5,427,908 A | 6/1995 | Dower et al. | |
| 5,432,018 A | 7/1995 | Dower et al. | |
| 5,498,530 A | 3/1996 | Schatz et al. | |
| 5,500,362 A | 3/1996 | Robinson et al. | |
| 5,521,184 A | 5/1996 | Zimmermann | |
| 5,580,717 A | 12/1996 | Dower et al. | |
| 5,658,727 A | 8/1997 | Barbas et al. | |
| 5,723,286 A | 3/1998 | Dower et al. | |
| 5,733,743 A | 3/1998 | Johnson et al. | |
| 5,750,373 A | 5/1998 | Garrard et al. | |
| 5,837,242 A | 11/1998 | Holliger et al. | |
| 5,969,108 A | 10/1999 | Mccafferty et al. | |
| 6,172,197 B1 | 1/2001 | Mccafferty et al. | |
| 6,204,011 B1 | 3/2001 | Kendall et al. | |
| 6,573,293 B2 | 6/2003 | Tang et al. | |
| 6,727,256 B1 | 4/2004 | Carter et al. | |
| 7,273,612 B2 | 9/2007 | Klagsbrun et al. | |
| 7,335,357 B2 | 2/2008 | Klagsbrun et al. | |
| 7,638,606 B2 | 12/2009 | Carter et al. | |
| 7,994,286 B2 | 8/2011 | Watts et al. | |
| 8,378,080 B2 * | 2/2013 | Watts et al. | 530/387.1 |
| 2002/0132774 A1 | 9/2002 | Klagsbrun et al. | |
| 2006/0166878 A1 | 7/2006 | Klagsbrun et al. | |
| 2008/0076906 A1 | 3/2008 | Klagsbrun et al. | |
| 2008/0213268 A1 | 9/2008 | Watts et al. | |

FOREIGN PATENT DOCUMENTS

| | | |
|---|---|---|
| EP | 0 368 684 B1 | 5/1990 |
| EP | 0 564 409 | 10/1993 |
| EP | 0 404 097 B1 | 9/1996 |
| EP | 0 817 648 B1 | 12/2004 |
| WO | 89/06692 | 7/1989 |
| WO | 93/11161 | 6/1993 |
| WO | 94/11499 | 5/1994 |
| WO | 95/27062 | 10/1995 |
| WO | 95/33050 | 12/1995 |
| WO | 96/40769 | 12/1996 |
| WO | 97/08313 | 3/1997 |
| WO | 98/35958 | 8/1998 |
| WO | 98/45331 | 10/1998 |
| WO | 98/45332 | 10/1998 |
| WO | 99/29729 | 6/1999 |
| WO | 99/29858 | 6/1999 |
| WO | 99/29861 | 6/1999 |
| WO | 99/35146 | 7/1999 |
| WO | 01/60814 A2 | 8/2001 |
| WO | 03/102157 A2 | 12/2003 |
| WO | 2004/056874 | 7/2004 |

OTHER PUBLICATIONS

Adamis, A. P. et al., "Inhibition of Vascular Endothelial Growth Factor Prevents Retinal Ischemia-Associated Iris Neovascularization in a Nonhuman Primate" Arch Ophthalmol-Chic 114(1):66-71 (1996).

Aiello, L. P. et al., "Vascular endothelial growth factor in ocular fluid of patients with diabetic retinopathy and other retinal disorders" New Engl J Med 331(22):1480-1487 (Dec. 1, 1994).

Amit et al., "Three-Dimensional Structure of an Antigen-Antibody Complex at 2.8 A Resolution" Science 233:747-753 (Aug. 1986).

Bachelder et al., "Vascular Endothelial Growth Factor Is an Autocrine Survival Factor for Neuropilin-expressing Breast Carcinoma Cells" Cancer Research 61:5736-5740 (Aug. 1, 2001).

Baluk et al., "Cellular Abnormalities of Blood Vessels as Targets in Cancer" Current Opinion in Genetics & Development 15:102-111 (2005).

Barbas & Burton, "Selection and evolution of high-affinity human anti-viral antibodies" Trends Biotech 14:230-234 (1996).

Barbas et al., "In vitro Evolution of a Neutralizing Human Antibody to Human Immunodeficiency Virus Type 1 to Enhance Affinity and Broaden Strain Cross-Reactivity" P Natl Acad Sci USA 91:3809-3813 (1994).

(Continued)

*Primary Examiner* — Jeffrey Stucker
*Assistant Examiner* — Stephen Gucker
(74) *Attorney, Agent, or Firm* — Clark & Elbing LLP; Karen L. Elbing

(57) ABSTRACT

Novel anti-NRP1 antibodies and variants thereof having unique structural and functional characteristics are disclosed. Also provided are uses of the antibodies in research, diagnostic and therapeutic applications.

18 Claims, 13 Drawing Sheets

(56) References Cited

OTHER PUBLICATIONS

Basile et al., "Class IV Semaphorins Promote Angiogenesis by Stimulating Rho-Initiated Pathways through Plexin-B" Cancer Research 64:5212-5224 (Aug. 1, 2004).

Benjamin et al., "A plasticity window for blood vessel remodelling is defined by pericyte coverage of the preformed endothelial network and is regulated by PDGF-B and VEGF" Development 125:1591-1598 (1998).

Bergers et al., "Benefits of targeting both pericytes and endothelial cells in the tumor vasculature with kinase inhibitors" J Clin Invest 111:1287-1295 (2003).

Berkman, R. A. et al., "Expression of the vascular permeability factor/vascular endothelial growth factor gene in central nervous system neoplasms" J Clin Invest 91:153-159 (Jan. 1993).

Bielenberg et al., "Neuropilins in neoplasms: Expression, regulation, and function" Exp. Cell Res. 312:584-593 (2006).

Bodey et al., "Failure of cancer vaccines: the significant limitations of this approach to immunotherapy" Anticancer Research 20(4):2665-2676 (Jul.-Aug. 2000).

Borgstrom, P. et al., "Complete inhibition of angiogenesis and growth of microtumors by anti-vascular endothelial growth factor neutralizing antibody: novel concepts of angiostatic therapy from intravital videomicroscopy" Cancer Res 56(17):4032-4039 (Sep. 1, 1996).

Bradbury and Marks, "Antibodies from phage antibody libraries" J Immunol Methods 290:29-49 (2004).

Brown, L. F. et al., "Expression of vascular permeability factor (vascular endothelial growth factor) and its receptors in breast cancer" Hum Pathol 26(1):86-91 (1995).

Brown, L. F. et al., "Expression of vascular permeability factor (vascular endothelial growth factor) and its receptors in adenocarcinomas of the gastrointestinal tract" Cancer Res 53:4727-4735 (Oct. 1, 1993).

Cai et al., "Cloning and Characterization of Neuropilin-1-Interacting Protein: A PSD-95/Dlg/ZO-1 Domain-Containing Protein That Interacts with the Cytoplasmic Domain of Neuropilin-1" J. Neurosci. 19:6519-6527 (1999).

Carmeliet and Tessier-Lavigne, "Common mechanisms of nerve and blood vessel wiring" Nature 436:193-200 (Jul. 14, 2005).

Carmeliet, P. et al., "Angiogenesis in cancer and other diseases" Nature 407(6801):249-257 (Sep. 14, 2000).

Carter et al., "High level *Escherichia coli* expression and production of a bivalent humanized antibody fragment" Bio-Technol 10(2):163-167 (Feb. 1992).

Carter et al., "Humanization of an Anti-p185 $^{HER2}$ Antibody For Human Cancer Therapy" P Natl Acad Sci USA 89(10):4285-4289 (May 1992).

Champe et al., "Monoclonal antibodies that block the activity of leukocyte function-associated antigen 1 recognize three discrete epitopes in the inserted domain of CD11a" J Biol Chem 270:1388-1394 (1995).

Chen et al., "Akt1 regulates pathological angiogenesis, vascular maturation and permeability in vivo" Nat Med 11:1188-1196 (2005).

Chen et al., "Neuropilin-2, a Novel Member of the Neuropilin Family, Is a High Affinity Receptor for the Semaphorins Sema E and Sema IV but Not Sema III" Neuron 19:547-559 (Sep. 1997).

Chothia et al., "Canonical structures for the hypervariable regions of immunoglobulins" J Mol Biol 196:901-917 (1987).

Chothia, C. et al., "Conformations of immunoglobulin hypervariable regions" Nature 342(21):877-883 (Dec. 28, 1989).

Clackson et al., "Making Antibody Fragments Using Phage Display Libraries" Nature 352(6336):624-628 (Aug. 15, 1991).

Connolly, J., "Analytical Molecular Surface Calculation" J. Appl. Cryst. 16:548-558 (1983).

Cross et al., "VEGF-receptor signal transduction" Trends Biochem. 28(9):488-494 (Sep. 2003).

Cunningham et al., "High-resolution epitope mapping of hGH-receptor interactions by alanine-scanning mutagenesis" Science 244:1081-1085 (Jun. 2, 1989).

de Haard et al., "A large non-immunized human Fab fragment phage library that permits rapid isolation and kinetic analysis of high affinity antibodies" Journal of Biological Chemistry 274(26):18218-18230 (Jun. 25, 1999).

De Vries et al., "GIPC, a PDZ domain containing protein, interacts specifically with the C terminus of RGS-GAIP" Proc. Natl. Acad. Sci. USA 95:12340-12345 (Oct. 1998).

de Wildt et al., "Antibody arrays for high-throughput screening of antibody-antigen interactions" Nat Biotechnol. 18(9):989-994 (Sep. 2000).

Deng et al., "Selection of Antibody Single-chain Variable Fragments with Improved Carbohydrate Binding by Phage Display" Journal of Biological Chemistry 269:9533-9538 (1994).

Dermer, G., "Another anniversary for the war on cancer" Biotechnology 12:320 (1994).

Dickson et al., "Molecular Mechanisms of Axon Guidance" Science 298:1959-64 (Dec. 6, 2002).

Dorrell and Friedlander, "Mechanisms of endothelial cell guidance and vascular patterning the developing mouse retina" Prog Retin Eye Res 25:277-95 (2006).

Dougher and Terman, "Autophosphorylation of KDR in the kinase domain is required for maximal VEGF-stimulated kinase activity and receptor internalization" Oncogene 18(8):1619-1627 (Feb. 25, 1999).

Dvorak et al., "Vascular permeability factor/vascular endothelial growth factor, microvascular hyperpermeability, and angiogenesis" Am J Pathol 146(5):1029-1039 (May 1995).

Erber et al., "Combined inhibition of VEGF and PDGF signaling enforces tumor vessel regression by interfering with pericyte-mediated endothelial cell survival mechanisms" Faseb J 18:338-340 (2004).

Ezzell, C., "Cancer 'Vaccines': An Idea Whose Time Has Come?" Journal of NIH Research 7:46-49 (Jan. 1995).

FDA News, "FDA Approves First Angiogenesis Inhibitor to Treat Colorectal Cancer" http://www.fda.gov/bbs/topics/NEWS/2004/NEW01027.html pp. P04-P23 (Feb. 26, 2004).

Ferrara and Davis-Smyth, "The Biology of Vascular Endothelial Growth Factor" Endocr Rev 18(1):4-25 (1997).

Ferrara and Kerbel et al., "Angiogenesis as a therapeutic target" Nature 438(7070):967-974 (Dec. 15, 2005).

Ferrara et al., "Clinical applications of angiogenic growth factors and their inhibitors" Nat Med 5(12):1359-1364 (Dec. 1999).

Finkle et al., "HER2-targeted therapy reduces incidence and progression of midlife mammary tumors in female murine mammary tumor virus huHER2-transgenic mice" Cinical Cancer Research 10(7):2499-2511 (Apr. 1, 2004).

Folkman and Shing, "Angiogenesis" J Biol Chem 267(16):10931-10934 (Jun. 5, 1992).

Folkman, J. et al., "Induction of angiogenesis during the transition from hyperplasia to neoplasia" Nature 339(6219):58-61 (1989).

Folkman, Judah, "Angiogenesis in cancer, vascular, rheumatoid and other disease" Nature Medicine 1(1):27-31 (1995).

Forsberg et al., "Identification of framework residues in a secreted recombinant antibody fragment that control production level and localization in *Escherichia coli*" J Biol Chem. 272(19):12430-12436 (May 1997).

Freshney, R. Culture of Animal Cells: A Manual of Basic Technique, New York:Alan R. Liss, Inc. pp. 3-4 (1983).

Fujisawa and Kitsukawa, "Receptors for collapsin/semahorins" Curr Opin Neurobiol 8:587-592 (1998).

Gallop et al., "Applications of Combinatorial Technologies to Drug Discovery Background and peptide combinatorial libraries" J Med Chem 37(9):1233-1251 (Apr. 29, 1994).

Garner, A. Pathobiology of Ocular Disease. A Dynamic Approach "Vascular Diseases" Garner, A., Klintworth GK Eds., 2nd edition, NY:Marcel Dekker,:1625-1710 (1994).

Garrand and Henner, "Selection of an anti-IGF-1 Fab from a Fab phage library created by mutagenesis of multiple CDR loops" Gene 128:103 (1993).

Gengrinovitch et al., "Platelet Factor-4 Inhibits the Mitogenic Activity of VEGF $_{121}$ and VEGF $_{165}$ Using Several Concurrent Mechanisms" Journal of Biological Chemistry 270(5):15059-15065 (1995).

(56) References Cited

OTHER PUBLICATIONS

Gerber et al., "Vascular endothelial growth factor induces expression of the antiapoptotic proteins Bcl-2 and A1 in vascular endothelial cells" J Biol Chem. 273(21):13313-13316 (May 22, 1998).
Gerhardt et al., "Neuropilin-1 Is Required for Endothelial Tip Cell Guidance in the Developing Central Nervous System" Dev Dyn 231:503-509 (2004).
Gerhardt et al., "VEGF guides angiogenic sprouting utilizing endothelial tip cell filopodia" J Cell Biol 161:1163-1177 (2003).
Goodman et al., "Unified Nomenclature for the Semaphorins/Collapsins" Cell 97:551-552 (May 28, 1999).
Gray et al., "Neuropilin-1 Suppresses Tumorigenic Properties in a Human Pancreatic Adenocarcinoma Cell Line Lacking Neuropilin-1 Coreceptors" Cancer Research 65(9):3664-3670 (May 1, 2005).
Griffiths et al., "Isolation of High Affinity Human Antibodies Directly From Large Synthetic Repertoires" EMBO Journal 13:3245-3260 (1994).
Gu et al., "Characterization of Neuropilin-1 Structural Features That Confer Binding to Semaphorin 3A and Vascular Endothelial Growth Factor 165" Journal of Biological Chemistry 277:18069-76 (2002).
Gu et al., "Neuropilin-1 Conveys Semaphorin and VEGF Signaling during Neural and Cardiovascular Development" Dev Cell 5:45-57 (2003).
Gura, T., "Systems for identifying new drugs are often faulty" Science 278:1041-1042 (Nov. 7, 1997).
Hanahan, D., "Signaling vascular morphogenesis and maintenance" Science 277:48-50 ( 1997).
Hansel et al., "Expression of Neuropilin-1 in High-grade Dysplasia, Invasive Cancer, and Metastases of the Human Gastrointestinal Tract" American Journal of Pathology 28(3):347-356 (Mar. 2004).
Harvard College 1994 ID R51427 standard, Protein, 33 AA, Accession No. R51726:A-geneseq32 Database.
Hawkins et al., "Selection of Phage Antibodies by Binding Affinity Mimicking Affinity Maturation" J Mol Biol 226:889-896 ( 1992).
He and Tessier-Lavigne, "Neuropilin Is a Receptor for the Axonal Chemorepellent Semaphorin III" Cell 90:739-751 (1997).
Herzog et al., "Differential expression of neuropilin-1 and neuropilin-2 in arteries and veins" Mech Dev 109:115-119 (2001).
Hillier et al., "yx21h06.s1 Soares melanocyte 2NbHM *Homo sapiens* cDNA clone Image:262427" Accession No. H99253, embl-est56 Database (1995).
Hoeschst Japan Ltd., 1994 ID R49994 standard, 1128 AA, Accession No. R49994:A-geneseq32 Database.
Hogan, B. L. M. et al., "Organogenesis: molecular mechanisms of tubulogenesis" Nat Rev Genet 3(7):513-523 (Jul. 2002).
Hollinger et al., ""Diabodies": Small Bivalent and Bispecific Antibody Fragments" Proc. Natl. Acad. Sci. USA 90:6444-6448 (Jul. 1993).
Hoogenboom et al., "Antibody phage display technology and its applications" Immunotechnology 4:1-20 (1998).
Horak et al., "Angiogenesis, assessed by platelet/endothelial cell adhesion molecule antibodies, as indicator of node metastises and survival in breast cancer" Lancet 340(8828):1120-1124 (1992).
Houck et al. et al., "The Vascular Endothelial Growth Factor Family: Identification of a Fourth Molecular Species and Characterization of Alternative Splicing of RNA" Mol Endocrinol 5(12):1806-14 ( 1991).
Huber et al., "Signaling at the Growth Cone: Ligand-Receptor Complexes and the Control of Axon Growth and Guidance" Annu. Rev. Neurosci. 26:509-63 (2003).
Inai et al., "Inhibition of Vascular Endothelial Growth Factor (VEGF) Signaling in Cancer Causes Loss of Endothelial Fenestrations, Regression of Tumor Vessels, and Appearance of Basement Membrane Ghosts" American Journal of Pathology 165(1):35-52 (Jul. 2004).
Jaalouk et al., "The Original Pathologische Anatomie Leiden-Endothelium Monoclonal Antibody Recognizes a Vascular Endothelial Growth Factor Binding Site within Neuropilin-1" Cancer Research 67(20):9623-9629 (Oct. 15, 2007).
Jackson et al., "In vitro antibody maturation. Improvement of a high affinity, neutralizing antibody against IL-1 beta" J Immunol 154(7):3310-3319 (Apr. 1, 1995).
Jain, R.K. et al., "Lessons from phase III clinical trial on anti-VEGF therapy for cancer" Nat. Clin. Pract. Oncol. 3(1):24-40 (Jan. 2006).
Jia et al., "Characterization of a Bicyclic Peptide Neuropilin-1 (NP-1) Antagonist (EG3287) Reveals Importance of Vascular Endothelial Growth Factor Exon 8 for NP-1 Binding and Role of NP-1 in KDR Signaling" Journal of Biological Chemistry 281(19):13493-13502 (May 12, 2006).
Jones et al., "Replacing the Complementarity-Determining Regions in a Human Antibody with Those From a Mouse" Nature 321(6069): 522-525 (May 29, 1986).
Kabat et al., "Unusual distributions of amino acids in complementarity-determining (hypervariable) segments of heavy and light chains of immunoglobulins and their possible roles in specificity of antibody-combining sites" J Biol. Chem. 252(19):6609-6616 (1997).
Kimiya et al., "The preserved expresison of neuropilin (NRP) 1 contributes to a better prognosis in colon cancer" Oncol. Rep. 15:369-373 (2006).
Karihaloo, A., et al., "Vascular Endothelial Growth Factor Induces Branching Morphogenesis/Tubulogenesis in Renal Epithelial Cells in a Neuropilin-dependent Fashion" Molecular & Cellular Biology 25(17):7441-7448 (Sep. 2005).
Kawakami et al., "Developmentally Regulated Expression of a Cell Surface Protein, Neuropilin, in the Mouse Nervous System" Journal of Neurobiology 29(1):1-17 (Jan. 1, 1996).
Kawakami et al., "Neuropilin 1 and Neuropilin 2 Co-Expression Is Significantly Correlated with Increased Vascularity and Poor Prognosis in Nonsmall Cell Lung Carcinoma" Cancer 95:2196-2201 (2002).
Kawasaki et al., "A Requirement for Neuropilin-1 in Embryonic Vessel Formation" Development 126:4895-4902 (1999).
Kerbel R.S. et al., "Possible mechanisms of acquired resistance to anti-angiogenic drugs: implications for the use of combination therapy approaches" Cancer Metastisis Rev. 20:79-86 (2001).
Kim et al., "Inhibition of Vascular Endothelial Growth Factor-Induced Angiogenesis Suppresses Tumour Growth in vivo" Nature 362:841-844 (Apr. 29, 1993).
Klagsbrun and D'Amore, "Regulators of angiogenesis" Ann Rev Physiol 53:217-239 ( 1991).
Klagsbrun et al., "The role of neuropilin in vascular and tumor biology" Adv Exp Med Biol 515:33-48 (2002).
Klagsbrun et al., "VEGF/VPF: the angiogenesis factor found?" Current Biology 3(10):699-702 (Jan. 1993).
Knappik et al., "Fully Synthetic Human Combinatorial Antibody Libraries (HuCAL) Based on Modular Consensus Frameworks and CDRs Randomized with Trinucleotides" J. Mol. Biol. 296(1):57-86 (Feb. 11, 2000).
Kohler and Milstein, "Continuous cultures of fused cells secreting antibody of predefined specificity" Nature 256:495-497 (Aug. 7, 1975).
Kolodkin et al., "Neuropilin Is a Semaphorin III Receptor" Cell 90:753-762 (Aug. 22, 1997).
Kowanetz et al., "Vascular Endothelial Growth Factor Signaling Pathways: Therapeutic Perspective" Clin Cancer Res 12(17):5018-5022 (2006).
Kunkel et al., "Efficient site-directed mutagenesis uracil-containing DNA" Methods in Enzymology 204:125-139 (1991).
Kunkel, T., "Rapid and Efficient Site-Specific Mutagenesis Without Phenotype Selection" Proc. Natl. Acad. Sci. 82(2):488-492 (Jan. 1985).
Latil et al., "VEGF overexpressions in clinically localized prostate tumors and neuropilin-1 overexpression in metastatic forms" Int. J. Cancer 89:167-171 (2000).
Lee et al., "Bivalent antibody phage display mimics natural immunoglobulin" J Immunol Methods. 284(1-2):119-132 (Jan. 2004).
Lee et al., "The Interpretation of Protein Structures: Estimation of Static Accessibility" J. Mol. Biol. 55:379-400 (1971).
Lee et al., "High-affinity human antibodies from phage-displayed synthetic Fab libraries with a single framework scaffold" J Mol Biol 340(5):1073-1093 (Jul. 23, 2004).

(56) References Cited

OTHER PUBLICATIONS

Leung et al. et al., "Vascular Endothelial Growth Factor is a Secreted Angiogenic Mitogen" Science 246:1306-1309 (Dec. 8, 1989).
Li et al., "Pancreatic Carcinoma Cells Express Neuropilins and Vascular Endothelial Growth Factor, but Not Vascular Endothelial Growth Factor Receptors" Cancer 101(10):2341-2350 (Nov. 15, 2004).
Liang et al. et al., "Function Blocking Antibodies to Neuropilin-1 Generated from a Designed Human Synthetic Antibody Phage Library" J Mol Biol 366:815-829 ( 2007).
Liang et al., "Cross-species vascular endothelial growth factor (VEGF)-blocking antibodies completely inhibit the growth of human tumor xenografts and measure the contribution of stromal VEGF" J Biol Chem. 281(2):951-61 (Jan. 2006).
Liu et al., "Upregulation of neuropilin-1 by basic fibroblast growth factor enhances vascular smooth muscle cell migration in response to VEGF" Cytokine 32:206-212 (2005).
Lopez, P. F. et al., "Transdifferentiated retinal pigment epithelial cells are immunoreactive for vascular endothelial growth factor in surgically excised age-related macular degeneration-related choroidal neurovascular membranes" Invest Ophth Vis Sci 37(5):855-868 (Apr. 1996).
Lowman and Wells, "Monovalent Phage Display: A Method for Selecting Variant Proteins from Random Libraries" Methods: A Companion to Methods in Enzymology 3:205-216 (Dec. 1991).
Lubarsky et al., "Tube morphogenesis: making and shaping biological tubes" Cell 112(1):19-28 (Jan. 10, 2003).
Macchiarini et al., "Relation of neovascularisation to metastasis of non-small-cell lung cancer" Lancet 340(8812):145-146 (1992).
Marks et al., "By-Passing Immunization: Human Antibodies From V-gene Libraries Displayed On Phage" J Mol Biol 222(3):581-597 (Dec. 5, 1991).
Mattern, J. et al., "Association of vascular endothelial growth factor expression with intratumoral microvessel density and tumour cell proliferation in human epidermoid lung carcinoma" Brit J Cancer 73:931-934 ( 1996).
Matthies et al., "Neuropilin-1 Participates in Wound Angiogenesis" American Journal of Pathology 160(1):289-296 (Jan. 2002).
Melnyk et al., "Vascular endothelial growth factor promotes tumor dissemination by a mechanism distinct from its effect on primary tumor growth" Cancer Res 56(4):921-924 (Feb. 15, 1996).
Mian et al., "Structure, function and properties of antibody binding sites" J. Mol. Biol. 217:133-151 (1991).
Miao et al., "Neuropilin-1 expression by tumor cells promotes tumor angiogenesis and progression" Faseb J 14:2532-2539 (2000).
Miao et al., "Neuropilin-1 Mediates Collapsin-1/Semaphorin III Inhibition of Endothelial Cell Motility: Functional Competition of Collapsin-1 and Vascular Endothelial Growth Factor-165" J Cell Biol 146:233-242 (1999).
Miller, "Issues and Challenges for Antiangiogenic Therapies" Breast Cancer Research and Treatment 75:S45-S50 (2002).
Morrison et al., "Chimeric human antibody molecules: Mouse antigen-binding domains with human constant region domains" P Natl Acad Sci USA 81:6851-6855 (Nov. 1984).
Muller et al., "Novel gene families involved in neural pathfinding" Current Opinion in Genetics and Development 6(4):469-474 (1996).
Murga et al., "Neuropilin-1 regulates attachment in human endothelial cells independently of vascular endothelial growth factor receptor-2" Blood 105:1992-1999 (2005).
Nakatsu et al., "Angiogenic sprouting and capillary lumen formation modeled by human umbilical vein endothelial cells (HUVEC) in fibrin gels: the role of fibroblasts and Angiopoietin-1" Microvasc Res. 66(2):102-112 (Sep. 2003).
Nasarre et al., "Semaphorin SEMA3F and VEGF Have Opposing Effects on Cell Attachment and Spreading" Neoplasia 5(1):83-92 (Jan. 2003).
Nasarre et al., "Semaphorin SEMA3F Has a Repulsing Activity on Breast Cancer Cells and Inhibits E-Cadherin-Mediated Cell Adhesion" Neoplasia 7(2):180-189 (Feb. 2005).
Neufeld et al., "Semaphorins in Cancer" Frontiers in Bioscience 10(751-760) (2005).
Ngo et al. The Protein Folding Problem and Tertiary Struction Prediction, Merz and Le Grand (Eds), Springer Verlag pp. 492-495 (Aug. 1994).
Nicolaou et al., "Calicheamicin $\theta^I{}_1$: A rationally designed molecule with extremely potent and selective DNA cleaving properties and apoptosis inducing activity" Angew Chem Intl Ed Engl 33(2):183-186 ( 1994).
Oh et al., "Selective induction of neuropilin-1 by vascular endothelial growth factor (VEGF): A mechanism contributing to VEGF-induced angiogenesis" Proceedings of the National Academy of Sciences 99(1):383-388 (Jan. 8, 2002).
Omura et al., "Identification of a 190-kDa Vascular Endothelial Growth Factor 165 Cell Surface Binding Protein on a Human Glioma Cell Line" Journal of Biological Chemistry 272(37):23317-23322 (Sep. 12, 1997).
Pacios, L., et al., "ARVOMOL/CONTOUR: molecular surface areas and volumes on personal computers" Computers Chem. 18(4):377-385 (1994).
Pan et al., "Blocking Neuropilin-1 Function Has an Additive Effect with Anti-VEGF to Inhibit Tumor Growth" Cancer Cell 11:53-67 (Jan. 2007).
Pharmagenics Inc. 1993 ID Q31949 standard, DNA, 405 bp, Accession No. Q31949:N-geneseq 32 Database.
Poltorak et al., "VEGF $_{145}$, a secreted vascular endothelial growth factor isoform that binds to extracellular matrix" J Biol Chem. 272(11):7151-8 (Mar. 14, 1997).
Pozas et al., "Age-Dependent Effects of Secreted Semaphorins 3A, 3F, and 3E on Devleoping Hippocampal Axons: In Vitro Effects and Phenotype of Semaphorin 3A (−/−) Mice" Molecular and Cellular Neuroscience 18:26-43 (2001).
Presta et al., "Humanization of an Anti-Vascular Endothelial Growth Factor Monoclonal Antibody for the Therapy of Solid Tumors and Other Disorders" Cancer Res 57(20):4593-4599 (Oct. 15, 1997).
Presta, "Antibody Engineering" Curr Opin Struc Biol 2:593-596 ( 1992).
Raper, "Semaphorins and their receptors in vertebrates and invertebrates" Curr Opin Neurobiol 10:88-94 (2000).
Riechmann et al., "Reshaping Human Antibodies for Therapy" Nature 332:323-327 (Mar. 24, 1988).
Rossignol et al., "Genomic Organization of Human Neuropilin-1 and Neuropilin-2 Genes: Identification and Distribution of Splice Variants and Soluble Isoforms" Genomics 70:211-222 (2000).
Rousseau et al., "p38 MAP kinase activation by vascular endothelial growth factor mediates actin reorganization and cell migration in human endothelial cells" Oncogene 15(18):2169-2177 (Oct. 1997).
Sato, "Molecular diagnosis of tumor angiogenesis and anti-angiogenic cancer therapy" Int J Clin Oncol 8(4):200-206 (Aug. 2003).
Serini et al., "Class 3 semaphorins control vascular morphogenesis by inhibiting integrin function" Nature 424:391-397 (Jul. 2003).
Sheets et al., "Efficient construction of a large nonimmune phage antibody library: the production of high-affinity human single-chain antibodies to protein antigens" Proc. Natl. Acad. Sci. USA 95(11):6157-6162 (May 1998).
Shojaei et al., "Antiangiogenesis to treat cancer and intraocular neovascular disorders" Laboratory Investigation 87:227-230 (2007).
Sidhu et al., "Phage-displayed Antibody Libraries of Synthetic Heavy Chain Complementarity Determining Regions" J Mol Biol 338(2):299-310 ( 2004).
Six et al., "Akt signaling mediates VEGF/VPF vascular permeability in vivo" FEBS Lett 532:67-69 (2002).
Skerra and Pluckthun, "Assembly of a functional immunoglobulin F$_v$ fragment in *Escherichia coli*" Science 240:1038-1041 (1988).
Smith, "Filamentous Fusion Phage: Novel Expression Vectors That Display Cloned Antigens on the Virion Surface" Science 228:1315-1317 (1985).
Soker et al., "Characterization of Novel Vascular Endothelial Growth Factor (VEGF) Receptors on Tumor Cells That Bind VEGF $_{165}$ via Its Exon 7-encoded Domain" Journal of Biological Chemistry 271(10):5761-5767 (Mar. 8, 1996).

(56) References Cited

OTHER PUBLICATIONS

Soker et al., "Inhibition of Vascular Endothelial Growth Factor (VEGF)-induced Endothelial Cell Proliferation by a Peptide Corresponding to the Exon 7-Encoded Domain of VEGF$_{165}$" Journal of Biological Chemistry 272(50):31582-31588 (Dec. 12, 1997).

Soker et al., "Neuropilin-1 is Expressed by Endothelial and Tumor Cells as an Isoform-Specific Receptor for Vascular Endothelial Growth Factor" Cell 92:735-745 (Mar. 20, 1998).

Soker et al., "VEGF$_{165}$ Mediates Formation of Complexes Containing VEGFR-2 and Neuropilin-1 That Enhance VEGF$_{165}$-Receptor Binding" J. Cell. Biochem. 85:357-368 (2002).

Spitler, Lynn E., "Cancer Vaccines: The interferon Analogy" Cancer Biotherapy 10:1-3 (1995).

Stephenson et al., "Neuropilin-1 Is Differentially Expressed In Myoepithelial Cells and Vascular Smooth Muscle Cells In Preneoplastic and Neoplastic Human Breast: A Possible Marker For The Progression of Breast Cancer" Int. J. Cancer 101:409-414 (2002).

Streit et al., "Angiogenesis, lymphangiogenesis, and melanoma metastisis" Oncogene 22(20):3172-3179 (May 19, 2003).

Takagi et al., "Expression of a Cell Adhesion Molecule, Neuropilin, in the Developing Chick Nervous System" Developmental Biology 170:207-222 (1995).

Takagi et al., "The A5 antigen, a candidate for the neuronal recognition molecule, has homologies to complement components and coagulation factors" Neuron 7:295-307 (1991).

Takahashi et al., "A single autophosphorylation site on KDR/Flk-1 is essential for VEGF-A-dependent activation of PLC-γ and DNA synthesis in vascular endothelial cells" EMBO Journal 20(11):2768-2778 (2001).

Takahashi et al., "VEGF activates protein kinase C-dependent, but Ras-independent Raf-MEK-MAP kinase pathway for DNA synthesis in primary endothelial cells" Oncogene 18:2221-2230 (1999).

Takashima et al., "Targeting of both mouse meuropilin-1 and neuropilin-2 genes severely impairs developmental yolk sac and embryonic angiogenesis" Proc. Natl. Acad. Sci. USA 99(6):3657-3662 (Mar. 19, 2002).

Tonini et al., "Molecular basis of angiogenesis and cancer" Oncogene 22(42):6549-6556 (Sep. 29, 2003).

Tordjman et al., "A neuronal receptor, neuropilin-1, is essential for the initiation of the primary immune response" Nature Immunology 3(5):477-482 (May 2002).

Ulrich et al., "Expression studies of catalytic antibodies" Proc. Natl. Acad. Sci. USA 92(25):11907-11911 (Dec. 5, 1995).

Vanveldhuizen et al., "Differential expression of neuropilin-1 in malignant and benign prostatic stromal tissue" Oncol. Rep. 10:1067-1071 (2003).

Vaughan et al., "Human Antibodies With Sub-nanomolar Affinities Isolated From a Large Non-immunized Phage Display Library" Nat Biotechnol 14:309-314 (Mar. 1996).

Verhoeyen et al., "Reshaping Human Antibodies: Grafting an Antilysozyme Activity" Science 239:1534-1536 (Mar. 1988).

Wang et al., "C terminus of RGS-GAIP-interacting protein conveys neuropilin-1-mediated signaling during angiogenesis" Faseb J 20:1513-1515 (2006).

Wang et al., "Neuropilin-1-mediated Vascular Permeability Factor/Vascular Endothelial Growth Factor-dependent Endothelial Cell Migration" Journal of Biological Chemistry 278(49):48848-48860 (2003).

Warren et al., "Regulation by vascular endothelial growth factor of human colon cancer tumorigenesis in a mouse model of experimental liver metastisis" J. Clin. Invest. 95(4):1789-1797 (Apr. 1995).

Watson et al., "Recombination at the Molecular Level" Molecular Biology of the Gene pp. 313-338 (1987).

Weidner, N. et al., "Tumor angiogenesis and metastisis—correlation in invasive breast carcinoma" New Engl J Med 324(1):1-8 (1991).

Weissenbach et al., "*H. sapiens* (D5S429) DNA segment containing (CA) repeat; clone AFM242xb10" Accession No. Z17097 enb156 Database (1994).

Wells and Lowman et al., "Rapid evolution of peptide and protein binding properties in vitro" Curr Opin Biotechnol 3:355-362 (1992).

Wey et al., "Overexpression of neuropilin-1 promotes constitutive MAPK signalling and chemoresistance in pancreatic cancer cells" Br. J. Cancer 93:233-241 (2005).

Wu, T., et al., "Length distribution of CDRH3 in antibodies" Proteins: Structure, Function, and Genetics 16:1-7 (1993).

Xu et al., "Diversity in the CDR3 region of V(H) is sufficient for most antibody specificities" Immunity 13(1):37-45 (Jul. 2000).

Yamada et al., "Exogenous clustered neuropilin 1 enhances vasculogenesis and angiogenesis" Blood 97(6):1671-8 (2001).

Yelton et al., "Affinity Maturation of the BR96 Anti-Carcinoma Antibody by Codon-Based Mutagenesis" J Immunol 155:1994-2004 (1995).

Yuan et al., "Abnormal lymphatic vessel development in neuropilin 2 mutant mice" Development 129:4797-4806 (2002).

Zapata et al., "Engineering linear F(ab')$_2$ fragments for efficient production in *Escherichia coli* and enhanced antiproliferative activity" Protein Eng 8(10):1057-1062 (1995).

Bendig, Mary M., "Humanization of Rodent Monoclonal Antibodies by CDR Grafting" Methods: A Companion to Methods in Enzymology 8:83-93 (1995).

Coleman, P.M., "Effects of amino acid sequence changes on antibody-antigen interactions" Res Immunol 145:33-36 (1994).

Paul, William E., "Structure and Function of Immunoglobulins" Fundamental Immunology, 3rd edition, New York:Raven Press Ltd., Chapter 9, pp. 292-295 (1993).

Rudikoff et al., Proc. Natl. Acad. Sci. USA, 79(6):1979-1983 (Mar. 1982).

\* cited by examiner

Light Chain

| Kabat No. | 1 2 3 4 5 6 7 8 9 10 11 12 13 14 15 16 17 18 19 20 21 22 23 | 24 25 26 27 28 29 30 31 32 33 34 35 36 37 |
|---|---|---|
| | | Kabat - CDR L1 |
| | | Chothia - CDR L1 |
| | | Contact - CDR L1 |
| h4D5 | D I Q M T Q S P S S L S A S V G D R V T I T C | R A S Q D V S T A V A W Y Q |
| αNRP1(YW64.3) | D I Q M T Q S P S S L S A S V G D R V T I T C | R A S Q S I S S Y L A W Y Q |
| αNRP1(YW107.4.87) | D I Q M T Q S P S S L S A S V G D R V T I T C | R A S Q S I F S Y L A W Y Q |

| Kabat No. | 38 39 40 41 42 43 44 45 46 47 48 49 | 50 51 52 53 54 55 56 | 57 58 59 60 61 62 63 64 65 66 67 68 69 70 71 72 73 74 75 76 77 78 79 80 |
|---|---|---|---|
| | | Kabat - CDR L2 | |
| | | Chothia - CDR L2 | |
| | | Contact - CDR L2 | |
| h4D5 | Q K P G K A P K L L I Y | S A S F L Y S | G V P S R F S G S G S G T D F T L T I S S L Q P |
| αNRP1(YW64.3) | Q K P G K A P K L L I Y | G A S S R A S | G V P S R F S G S G S G T D F T L T I S S L Q P |
| αNRP1(YW107.4.87) | Q K P G K A P K L L I Y | G A S S R A S | G V P S R F S G S G S G T D F T L T I S S L Q P |

| Kabat No. | 81 82 83 84 85 86 87 88 | 89 90 91 92 93 94 95 96 97 | 98 99 100 101 102 103 104 105 106 107 108 |
|---|---|---|---|
| | | Kabat - CDR L3 | |
| | | Chothia - CDR L3 | |
| | | Contact - CDR L3 | |
| h4D5 | E D F A T Y Y C | Q Q S Y T T P P T | F G Q G T K V E I K R | (SEQ ID NO:1) |
| αNRP1(YW64.3) | E D F A T Y Y C | Q Q Y E M S V P I T | F G Q G T K V E I K R | (SEQ ID NO:3) |
| αNRP1(YW107.4.87) | E D F A T Y Y C | Q Q Y L G S P P T | F G Q G T K V E I K R | (SEQ ID NO:5) |

*FIG. 3A*

Heavy Chain

| Kabat No. | 1 2 3 4 5 6 7 8 9 10 11 12 13 14 15 16 17 18 19 20 21 22 23 24 25 26 27 28 29 30 31 32 33 34 35 36 37 38 39 40 |
|---|---|
| h4D5 | E V Q L V E S G G G L V Q P G G S L R L S C A A S G F N I K D T Y I H W V R Q A |
| αNRP1(YW64.3) | E V Q L V E S G G G L V Q P G G S L R L S C A A S G F S F S S E P I S W V R Q A |
| αNRP1(YW107.4.87) | E V Q L V E S G G G L V Q P G G S L R L S C A A S G F T F S S Y A M S W V R Q A |

Kabat - CDR H1
Chothia - CDR H1
Contact - CDR H1

| Kabat No. | 41 42 43 44 45 46 47 48 49 50 51 52 A 53 54 55 56 57 58 59 60 61 62 63 64 65 66 67 68 69 70 71 72 73 74 75 76 77 78 |
|---|---|
| h4D5 | P G K G L E W V A R I Y P T N G Y T R Y A D S V K G R F T I S A D T S K N T A |
| αNRP1(YW64.3) | P G K G L E W V S I W G K G T Y Y A D S V K G R F T I S A D T S K N T A |
| αNRP1(YW107.4.87) | P G K G L E W V S Q I S P A G G Y T N Y A D S V K G R F T I S A D T S K N T A |

Contact - CDR H2
Chothia - CDR H2
Kabat - CDR H2

| Kabat No. | 79 80 81 82 A B C 83 84 85 86 87 88 89 90 91 92 93 94 95 96 97 98 99 100 A B C D E F G H 101 102 103 104 105 106 107 |
|---|---|
| h4D5 | Y L Q M N S L R A E D T A V Y Y C S R W G G D G F Y A M D Y W G Q G T |
| αNRP1(YW64.3) | Y L Q M N S L R A E D T A V Y Y C A R M G K K V Y G M D V W G Q G T |
| αNRP1(YW107.4.87) | Y L Q M N S L R A E D T A V Y Y C A R B L P Y Y R M S K V M D V W G Q G T |

Kabat - CDR H3
Chothia - CDR H3
Contact - CDR H3

| Kabat No. | 108 109 110 111 112 113 |
|---|---|
| h4D5 | L V T V S S (SEQ ID NO:2) |
| αNRP1(YW64.3) | L V T V S S (SEQ ID NO:4) |
| αNRP1(YW107.4.87) | L V T V S S (SEQ ID NO:6) |

*FIG. 3B*

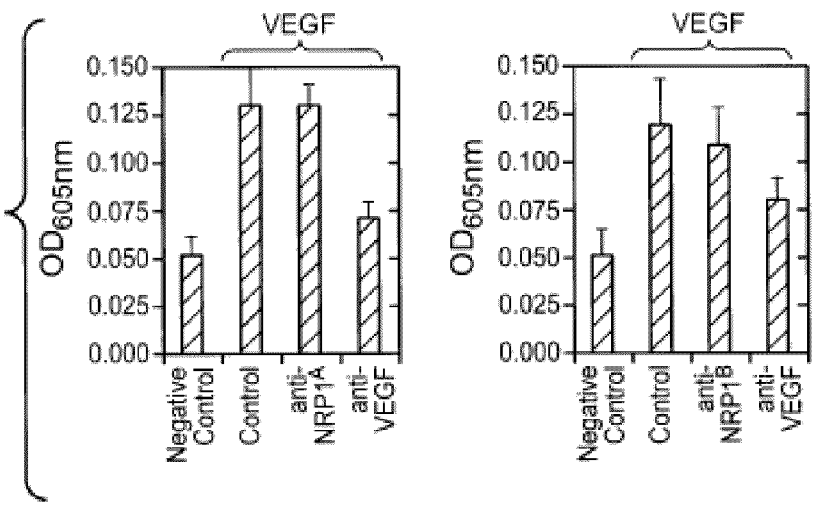
FIG. 8A
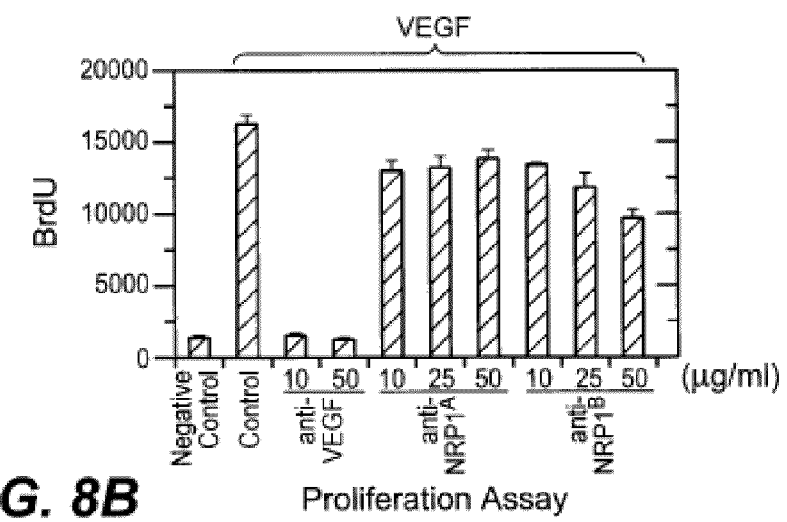
FIG. 8B  Proliferation Assay
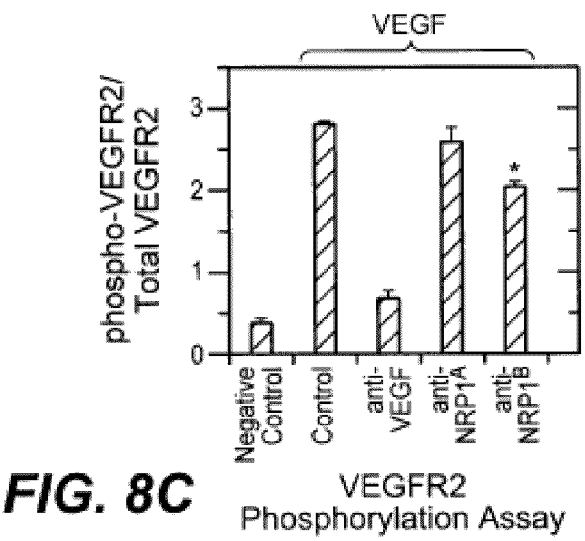
FIG. 8C  VEGFR2 Phosphorylation Assay

SEQUENCE LISTING

<160> NUMBER OF SEQ ID NOS: 135

<210> SEQ ID NO 1
<211> LENGTH: 108

<212> TYPE: PRT
<213> ORGANISM: Artificial sequence
<220> FEATURE:
<223> OTHER INFORMATION: sequence is synthesized

<400> SEQUENCE: 1

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Asp Val Ser
                20                  25                  30

Thr Ala Val Ala Trp Tyr Gln Gln Lys Pro Gly Lys Ala Pro Lys
                35                  40                  45

Leu Leu Ile Tyr Ser Ala Ser Phe Leu Tyr Ser Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

Ser Tyr Thr Thr Pro Pro Thr Phe Gly Gln Gly Thr Lys Val Glu
                95                 100                 105

Ile Lys Arg

<210> SEQ ID NO 2
<211> LENGTH: 120
<212> TYPE: PRT
<213> ORGANISM: Artificial sequence
<220> FEATURE:
<223> OTHER INFORMATION: sequence is synthesized

<400> SEQUENCE: 2

Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Asn Ile Lys
                20                  25                  30

Asp Thr Tyr Ile His Trp Val Arg Gln Ala Pro Gly Lys Gly Leu
                35                  40                  45

Glu Trp Val Ala Arg Ile Tyr Pro Thr Asn Gly Tyr Thr Arg Tyr
                50                  55                  60

Ala Asp Ser Val Lys Gly Arg Phe Thr Ile Ser Ala Asp Thr Ser
                65                  70                  75

Lys Asn Thr Ala Tyr Leu Gln Met Asn Ser Leu Arg Ala Glu Asp
                80                  85                  90

Thr Ala Val Tyr Tyr Cys Ser Arg Trp Gly Gly Asp Gly Phe Tyr
                95                 100                 105

Ala Met Asp Tyr Trp Gly Gln Gly Thr Leu Val Thr Val Ser Ser
               110                 115                 120

<210> SEQ ID NO 3
<211> LENGTH: 108
<212> TYPE: PRT
<213> ORGANISM: Artificial sequence
<220> FEATURE:
<223> OTHER INFORMATION: sequence is synthesized

<400> SEQUENCE: 3

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Ser Ile Ser
                20                  25                  30

```
Ser Tyr Leu Ala Trp Tyr Gln Gln Lys Pro Gly Lys Ala Pro Lys
            35                  40                  45

Leu Leu Ile Tyr Gly Ala Ser Ser Arg Ala Ser Gly Val Pro Ser
            50                  55                  60

Arg Phe Ser Gly Ser Gly Ser Gly Thr Asp Phe Thr Leu Thr Ile
            65                  70                  75

Ser Ser Leu Gln Pro Glu Asp Phe Ala Thr Tyr Tyr Cys Gln Gln
            80                  85                  90

Tyr Met Ser Val Pro Ile Thr Phe Gly Gln Gly Thr Lys Val Glu
            95                 100                 105

Ile Lys Arg

<210> SEQ ID NO 4
<211> LENGTH: 119
<212> TYPE: PRT
<213> ORGANISM: Artificial sequence
<220> FEATURE:
<223> OTHER INFORMATION: sequence is synthesized

<400> SEQUENCE: 4

Glu Val Gln Leu Val Glu Ser Gly Gly Gly Leu Val Gln Pro Gly
  1               5                  10                  15

Gly Ser Leu Arg Leu Ser Cys Ala Ala Ser Gly Phe Ser Phe Ser
            20                  25                  30

Ser Glu Pro Ile Ser Trp Val Arg Gln Ala Pro Gly Lys Gly Leu
            35                  40                  45

Glu Trp Val Ser Ser Ile Thr Gly Lys Asn Gly Tyr Thr Tyr Tyr
            50                  55                  60

Ala Asp Ser Val Lys Gly Arg Phe Thr Ile Ser Ala Asp Thr Ser
            65                  70                  75

Lys Asn Thr Ala Tyr Leu Gln Met Asn Ser Leu Arg Ala Glu Asp
            80                  85                  90

Thr Ala Val Tyr Tyr Cys Ala Arg Trp Gly Lys Lys Val Tyr Gly
            95                 100                 105

Met Asp Val Trp Gly Gln Gly Thr Leu Val Thr Val Ser Ser
           110                 115

<210> SEQ ID NO 5
<211> LENGTH: 108
<212> TYPE: PRT
<213> ORGANISM: Artificial sequence
<220> FEATURE:
<223> OTHER INFORMATION: sequence is synthesized

<400> SEQUENCE: 5

Asp Ile Gln Met Thr Gln Ser Pro Ser Ser Leu Ser Ala Ser Val
  1               5                  10                  15

Gly Asp Arg Val Thr Ile Thr Cys Arg Ala Ser Gln Tyr Phe Ser
            20                  25                  30

Ser Tyr Leu Ala Trp Tyr Gln Gln Lys Pro Gly Lys Ala Pro Lys
            35                  40                  45

Leu Leu Ile Tyr Gly Ala Ser Ser Arg Ala Ser Gly Val Pro Ser
            50                  55                  60

Arg Phe Ser Gly Ser Gly Ser Gly Thr Asp Phe Thr Leu Thr Ile
            65                  70                  75

Ser Ser Leu Gln Pro Glu Asp Phe Ala Thr Tyr Tyr Cys Gln Gln
            80                  85                  90
```

Tyr Leu Gly Ser Pro Pro Thr Phe Gly Gln Gly Thr Lys Val Glu
                95                 100                 105

Ile Lys Arg

<210> SEQ ID NO 6
<211> LENGTH: 122
<212> TYPE: PRT
<213> ORGANISM: Artificial sequence
<220> FEATURE:
<223> OTHER INFORMATION: sequence is synthesized

<400> SEQUENCE: 6

Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Thr Phe Ser
                20                  25                  30

Ser Tyr Ala Met Ser Trp Val Arg Gln Ala Pro Gly Lys Gly Leu
                35                  40                  45

Glu Trp Val Ser Gln Ile Ser Pro Ala Gly Gly Tyr Thr Asn Tyr
                50                  55                  60

Ala Asp Ser Val Lys Gly Arg Phe Thr Ile Ser Ala Asp Thr Ser
                65                  70                  75

Lys Asn Thr Ala Tyr Leu Gln Met Asn Ser Leu Arg Ala Glu Asp
                80                  85                  90

Thr Ala Val Tyr Tyr Cys Ala Arg Glu Leu Pro Tyr Tyr Arg Met
                95                 100                 105

Ser Lys Val Met Asp Val Trp Gly Gln Gly Thr Leu Val Thr Val
                110                 115                 120

Ser Ser

<210> SEQ ID NO 7
<211> LENGTH: 6
<212> TYPE: PRT
<213> ORGANISM: Artificial sequence
<220> FEATURE:
<223> OTHER INFORMATION: sequence is synthesized

<400> SEQUENCE: 7

Tyr Met Ser Val Pro Ile
 1               5

<210> SEQ ID NO 8
<211> LENGTH: 6
<212> TYPE: PRT
<213> ORGANISM: Artificial sequence
<220> FEATURE:
<223> OTHER INFORMATION: sequence is synthesized

<400> SEQUENCE: 8

Tyr Tyr Ser Ser Pro Leu
 1               5

<210> SEQ ID NO 9
<211> LENGTH: 6
<212> TYPE: PRT
<213> ORGANISM: Artificial sequence
<220> FEATURE:
<223> OTHER INFORMATION: sequence is synthesized

<400> SEQUENCE: 9

Tyr Tyr Ser Ser Pro Leu

<210> SEQ ID NO 10
<211> LENGTH: 6
<212> TYPE: PRT
<213> ORGANISM: Artificial sequence
<220> FEATURE:
<223> OTHER INFORMATION: sequence is synthesized

<400> SEQUENCE: 10

Tyr Tyr Ser Ser Pro Leu
 1               5

<210> SEQ ID NO 11
<211> LENGTH: 6
<212> TYPE: PRT
<213> ORGANISM: Artificial sequence
<220> FEATURE:
<223> OTHER INFORMATION: sequence is synthesized

<400> SEQUENCE: 11

Tyr Tyr Ser Ser Pro Leu
 1               5

<210> SEQ ID NO 12
<211> LENGTH: 6
<212> TYPE: PRT
<213> ORGANISM: Artificial sequence
<220> FEATURE:
<223> OTHER INFORMATION: sequence is synthesized

<400> SEQUENCE: 12

Arg Tyr Ser Val Pro Ile
 1               5

<210> SEQ ID NO 13
<211> LENGTH: 6
<212> TYPE: PRT
<213> ORGANISM: Artificial sequence
<220> FEATURE:
<223> OTHER INFORMATION: sequence is synthesized

<400> SEQUENCE: 13

Tyr Tyr Ser Ser Pro Leu
 1               5

<210> SEQ ID NO 14
<211> LENGTH: 6
<212> TYPE: PRT
<213> ORGANISM: Artificial sequence
<220> FEATURE:
<223> OTHER INFORMATION: sequence is synthesized

<400> SEQUENCE: 14

Tyr Tyr Ser Ser Pro Leu
 1               5

<210> SEQ ID NO 15
<211> LENGTH: 6
<212> TYPE: PRT
<213> ORGANISM: Artificial sequence
<220> FEATURE:
<223> OTHER INFORMATION: sequence is synthesized

<400> SEQUENCE: 15

Tyr Tyr Ser Ser Pro Leu
 1               5

```
<210> SEQ ID NO 16
<211> LENGTH: 6
<212> TYPE: PRT
<213> ORGANISM: Artificial sequence
<220> FEATURE:
<223> OTHER INFORMATION: sequence is synthesized

<400> SEQUENCE: 16

Tyr Tyr Ser Ser Pro Leu
 1               5

<210> SEQ ID NO 17
<211> LENGTH: 6
<212> TYPE: PRT
<213> ORGANISM: Artificial sequence
<220> FEATURE:
<223> OTHER INFORMATION: sequence is synthesized

<400> SEQUENCE: 17

Tyr Tyr Ser Ser Pro Leu
 1               5

<210> SEQ ID NO 18
<211> LENGTH: 8
<212> TYPE: PRT
<213> ORGANISM: Artificial sequence
<220> FEATURE:
<223> OTHER INFORMATION: sequence is synthesized

<400> SEQUENCE: 18

Phe Ser Phe Ser Ser Glu Pro Ile
 1               5

<210> SEQ ID NO 19
<211> LENGTH: 8
<212> TYPE: PRT
<213> ORGANISM: Artificial sequence
<220> FEATURE:
<223> OTHER INFORMATION: sequence is synthesized

<400> SEQUENCE: 19

Phe Thr Phe Ser Ser Tyr Ala Met
 1               5

<210> SEQ ID NO 20
<211> LENGTH: 8
<212> TYPE: PRT
<213> ORGANISM: Artificial sequence
<220> FEATURE:
<223> OTHER INFORMATION: sequence is synthesized

<400> SEQUENCE: 20

Tyr Ser Phe Ser Ser His Met Met
 1               5

<210> SEQ ID NO 21
<211> LENGTH: 8
<212> TYPE: PRT
<213> ORGANISM: Artificial sequence
<220> FEATURE:
<223> OTHER INFORMATION: sequence is synthesized

<400> SEQUENCE: 21

Phe Thr Phe Ser Ser Tyr Ala Met
 1               5
```

<210> SEQ ID NO 22
<211> LENGTH: 8
<212> TYPE: PRT
<213> ORGANISM: Artificial sequence
<220> FEATURE:
<223> OTHER INFORMATION: sequence is synthesized

<400> SEQUENCE: 22

Phe Thr Phe Ser Ser Tyr Ala Met
  1               5

<210> SEQ ID NO 23
<211> LENGTH: 8
<212> TYPE: PRT
<213> ORGANISM: Artificial sequence
<220> FEATURE:
<223> OTHER INFORMATION: sequence is synthesized

<400> SEQUENCE: 23

Phe Thr Phe Ser Ser Tyr Gln Leu
  1               5

<210> SEQ ID NO 24
<211> LENGTH: 8
<212> TYPE: PRT
<213> ORGANISM: Artificial sequence
<220> FEATURE:
<223> OTHER INFORMATION: sequence is synthesized

<400> SEQUENCE: 24

Phe Thr Phe Ser Ser Tyr Ala Met
  1               5

<210> SEQ ID NO 25
<211> LENGTH: 8
<212> TYPE: PRT
<213> ORGANISM: Artificial sequence
<220> FEATURE:
<223> OTHER INFORMATION: sequence is synthesized

<400> SEQUENCE: 25

Phe Thr Phe Ser Gln Tyr Ser Ile
  1               5

<210> SEQ ID NO 26
<211> LENGTH: 8
<212> TYPE: PRT
<213> ORGANISM: Artificial sequence
<220> FEATURE:
<223> OTHER INFORMATION: sequence is synthesized

<400> SEQUENCE: 26

Phe Thr Phe Thr Ser Arg Thr Met
  1               5

<210> SEQ ID NO 27
<211> LENGTH: 8
<212> TYPE: PRT
<213> ORGANISM: Artificial sequence
<220> FEATURE:
<223> OTHER INFORMATION: sequence is synthesized

<400> SEQUENCE: 27

Phe Thr Phe Ser Ser Tyr Ala Met
  1               5

```
<210> SEQ ID NO 28
<211> LENGTH: 8
<212> TYPE: PRT
<213> ORGANISM: Artificial sequence
<220> FEATURE:
<223> OTHER INFORMATION: sequence is synthesized

<400> SEQUENCE: 28

Phe Thr Phe Ser Ser Tyr Ala Met
 1               5

<210> SEQ ID NO 29
<211> LENGTH: 9
<212> TYPE: PRT
<213> ORGANISM: Artificial sequence
<220> FEATURE:
<223> OTHER INFORMATION: sequence is synthesized

<400> SEQUENCE: 29

Ser Ile Thr Gly Lys Asn Gly Tyr Tyr
 1               5

<210> SEQ ID NO 30
<211> LENGTH: 9
<212> TYPE: PRT
<213> ORGANISM: Artificial sequence
<220> FEATURE:
<223> OTHER INFORMATION: sequence is synthesized

<400> SEQUENCE: 30

Ser Ile Ala Gly Ser Gly Gly Tyr Tyr
 1               5

<210> SEQ ID NO 31
<211> LENGTH: 9
<212> TYPE: PRT
<213> ORGANISM: Artificial sequence
<220> FEATURE:
<223> OTHER INFORMATION: sequence is synthesized

<400> SEQUENCE: 31

Ser Ile Tyr Pro Pro Gly Gly Tyr Tyr
 1               5

<210> SEQ ID NO 32
<211> LENGTH: 9
<212> TYPE: PRT
<213> ORGANISM: Artificial sequence
<220> FEATURE:
<223> OTHER INFORMATION: sequence is synthesized

<400> SEQUENCE: 32

Thr Ile Ile Pro His Gly Gly Tyr Tyr
 1               5

<210> SEQ ID NO 33
<211> LENGTH: 9
<212> TYPE: PRT
<213> ORGANISM: Artificial sequence
<220> FEATURE:
<223> OTHER INFORMATION: sequence is synthesized

<400> SEQUENCE: 33

Trp Ile Ser Pro Leu Asn Gly Tyr Tyr
 1               5

<210> SEQ ID NO 34
```

```
<211> LENGTH: 8
<212> TYPE: PRT
<213> ORGANISM: Artificial sequence
<220> FEATURE:
<223> OTHER INFORMATION: sequence is synthesized

<400> SEQUENCE: 34

Ser Ile Phe Ser Gly Gly Tyr Tyr
  1               5

<210> SEQ ID NO 35
<211> LENGTH: 9
<212> TYPE: PRT
<213> ORGANISM: Artificial sequence
<220> FEATURE:
<223> OTHER INFORMATION: sequence is synthesized

<400> SEQUENCE: 35

Ser Ile Ser Arg Gly Asp Gly Tyr Tyr
  1               5

<210> SEQ ID NO 36
<211> LENGTH: 9
<212> TYPE: PRT
<213> ORGANISM: Artificial sequence
<220> FEATURE:
<223> OTHER INFORMATION: sequence is synthesized

<400> SEQUENCE: 36

Thr Ile Tyr Pro Phe Gly Gly Tyr Tyr
  1               5

<210> SEQ ID NO 37
<211> LENGTH: 8
<212> TYPE: PRT
<213> ORGANISM: Artificial sequence
<220> FEATURE:
<223> OTHER INFORMATION: sequence is synthesized

<400> SEQUENCE: 37

Ser Ile Ser Ser Gly Gly Tyr Tyr
  1               5

<210> SEQ ID NO 38
<211> LENGTH: 9
<212> TYPE: PRT
<213> ORGANISM: Artificial sequence
<220> FEATURE:
<223> OTHER INFORMATION: sequence is synthesized

<400> SEQUENCE: 38

Ser Ile Tyr Ser Thr Gly Gly Tyr Tyr
  1               5

<210> SEQ ID NO 39
<211> LENGTH: 9
<212> TYPE: PRT
<213> ORGANISM: Artificial sequence
<220> FEATURE:
<223> OTHER INFORMATION: sequence is synthesized

<400> SEQUENCE: 39

Gln Ile Ser Pro Ala Gly Gly Tyr Asn
  1               5

<210> SEQ ID NO 40
<211> LENGTH: 10
```

```
<212> TYPE: PRT
<213> ORGANISM: Artificial sequence
<220> FEATURE:
<223> OTHER INFORMATION: sequence is synthesized

<400> SEQUENCE: 40

Trp Gly Lys Lys Val Tyr Gly Met Asp Val
 1               5                  10

<210> SEQ ID NO 41
<211> LENGTH: 11
<212> TYPE: PRT
<213> ORGANISM: Artificial sequence
<220> FEATURE:
<223> OTHER INFORMATION: sequence is synthesized

<400> SEQUENCE: 41

Trp Gly Gly Ser Asn Gly Ser Gly Phe Asp Tyr
 1               5                  10

<210> SEQ ID NO 42
<211> LENGTH: 10
<212> TYPE: PRT
<213> ORGANISM: Artificial sequence
<220> FEATURE:
<223> OTHER INFORMATION: sequence is synthesized

<400> SEQUENCE: 42

Trp Gly Ser Arg Ser Pro Gly Met Asp Val
 1               5                  10

<210> SEQ ID NO 43
<211> LENGTH: 10
<212> TYPE: PRT
<213> ORGANISM: Artificial sequence
<220> FEATURE:
<223> OTHER INFORMATION: sequence is synthesized

<400> SEQUENCE: 43

Trp Ala Lys Arg Ser Tyr Gly Met Asp Val
 1               5                  10

<210> SEQ ID NO 44
<211> LENGTH: 10
<212> TYPE: PRT
<213> ORGANISM: Artificial sequence
<220> FEATURE:
<223> OTHER INFORMATION: sequence is synthesized

<400> SEQUENCE: 44

Trp Gly Arg Arg Tyr Ile Gly Met Asp Val
 1               5                  10

<210> SEQ ID NO 45
<211> LENGTH: 8
<212> TYPE: PRT
<213> ORGANISM: Artificial sequence
<220> FEATURE:
<223> OTHER INFORMATION: sequence is synthesized

<400> SEQUENCE: 45

Tyr Gly Asn His Val Met Asp Val
 1               5

<210> SEQ ID NO 46
<211> LENGTH: 9
<212> TYPE: PRT
```

<213> ORGANISM: Artificial sequence
<220> FEATURE:
<223> OTHER INFORMATION: sequence is synthesized

<400> SEQUENCE: 46

Trp Ala Gly Gly Ser Ala Met Asp Val
 1               5

<210> SEQ ID NO 47
<211> LENGTH: 14
<212> TYPE: PRT
<213> ORGANISM: Artificial sequence
<220> FEATURE:
<223> OTHER INFORMATION: sequence is synthesized

<400> SEQUENCE: 47

Phe Gly Gln Ser Tyr Tyr Gly Gly Ser Tyr Ala Met Asp Val
 1               5                  10

<210> SEQ ID NO 48
<211> LENGTH: 9
<212> TYPE: PRT
<213> ORGANISM: Artificial sequence
<220> FEATURE:
<223> OTHER INFORMATION: sequence is synthesized

<400> SEQUENCE: 48

Trp Glu Ser Tyr Tyr Gly Met Asp Val
 1               5

<210> SEQ ID NO 49
<211> LENGTH: 8
<212> TYPE: PRT
<213> ORGANISM: Artificial sequence
<220> FEATURE:
<223> OTHER INFORMATION: sequence is synthesized

<400> SEQUENCE: 49

Trp Gly Tyr Pro Gly Met Asp Val
 1               5

<210> SEQ ID NO 50
<211> LENGTH: 13
<212> TYPE: PRT
<213> ORGANISM: Artificial sequence
<220> FEATURE:
<223> OTHER INFORMATION: sequence is synthesized

<400> SEQUENCE: 50

Glu Leu Pro Tyr Tyr Arg Met Ser Lys Val Met Asp Val
 1               5                  10

<210> SEQ ID NO 51
<211> LENGTH: 5
<212> TYPE: PRT
<213> ORGANISM: Artificial sequence
<220> FEATURE:
<223> OTHER INFORMATION: sequence is synthesized

<400> SEQUENCE: 51

Ser Ile Ser Ser Tyr
 1               5

<210> SEQ ID NO 52
<211> LENGTH: 5
<212> TYPE: PRT
<213> ORGANISM: Artificial sequence
<220> FEATURE:
<223> OTHER INFORMATION: sequence is synthesized

<400> SEQUENCE: 52

Tyr Ile Ser Ser Tyr
 1               5

<210> SEQ ID NO 53
<211> LENGTH: 5
<212> TYPE: PRT
<213> ORGANISM: Artificial sequence
<220> FEATURE:
<223> OTHER INFORMATION: sequence is synthesized

<400> SEQUENCE: 53

Tyr Ile Ser Ser Tyr
 1               5

<210> SEQ ID NO 54
<211> LENGTH: 5
<212> TYPE: PRT
<213> ORGANISM: Artificial sequence
<220> FEATURE:
<223> OTHER INFORMATION: sequence is synthesized

<400> SEQUENCE: 54

Tyr Ile Ser Ser Tyr
 1               5

<210> SEQ ID NO 55
<211> LENGTH: 5
<212> TYPE: PRT
<213> ORGANISM: Artificial sequence
<220> FEATURE:
<223> OTHER INFORMATION: sequence is synthesized

<400> SEQUENCE: 55

Tyr Ile Ser Ser Tyr
 1               5

<210> SEQ ID NO 56
<211> LENGTH: 5
<212> TYPE: PRT
<213> ORGANISM: Artificial sequence
<220> FEATURE:
<223> OTHER INFORMATION: sequence is synthesized

<400> SEQUENCE: 56

Tyr Ile Ser Ser Tyr
 1               5

<210> SEQ ID NO 57
<211> LENGTH: 5
<212> TYPE: PRT
<213> ORGANISM: Artificial sequence
<220> FEATURE:
<223> OTHER INFORMATION: sequence is synthesized

<400> SEQUENCE: 57

Tyr Ile Ser Ser Tyr
 1               5

<210> SEQ ID NO 58
<211> LENGTH: 5
<212> TYPE: PRT
<213> ORGANISM: Artificial sequence
<220> FEATURE:

<223> OTHER INFORMATION: sequence is synthesized

<400> SEQUENCE: 58

Arg Ile Ser Ser Tyr
1               5

<210> SEQ ID NO 59
<211> LENGTH: 5
<212> TYPE: PRT
<213> ORGANISM: Artificial sequence
<220> FEATURE:
<223> OTHER INFORMATION: sequence is synthesized

<400> SEQUENCE: 59

Tyr Ile Ser Ser Tyr
1               5

<210> SEQ ID NO 60
<211> LENGTH: 5
<212> TYPE: PRT
<213> ORGANISM: Artificial sequence
<220> FEATURE:
<223> OTHER INFORMATION: sequence is synthesized

<400> SEQUENCE: 60

Trp Ile His Ser Tyr
1               5

<210> SEQ ID NO 61
<211> LENGTH: 5
<212> TYPE: PRT
<213> ORGANISM: Artificial sequence
<220> FEATURE:
<223> OTHER INFORMATION: sequence is synthesized

<400> SEQUENCE: 61

Arg Ile His Ser Tyr
1               5

<210> SEQ ID NO 62
<211> LENGTH: 5
<212> TYPE: PRT
<213> ORGANISM: Artificial sequence
<220> FEATURE:
<223> OTHER INFORMATION: sequence is synthesized

<400> SEQUENCE: 62

Tyr Ile His Ser Tyr
1               5

<210> SEQ ID NO 63
<211> LENGTH: 5
<212> TYPE: PRT
<213> ORGANISM: Artificial sequence
<220> FEATURE:
<223> OTHER INFORMATION: sequence is synthesized

<400> SEQUENCE: 63

Pro Leu His Ser Tyr
1               5

<210> SEQ ID NO 64
<211> LENGTH: 5
<212> TYPE: PRT
<213> ORGANISM: Artificial sequence
<220> FEATURE:
<223> OTHER INFORMATION: sequence is synthesized

<400> SEQUENCE: 64

Tyr Leu Ser Ser Tyr
 1               5

<210> SEQ ID NO 65
<211> LENGTH: 5
<212> TYPE: PRT
<213> ORGANISM: Artificial sequence
<220> FEATURE:
<223> OTHER INFORMATION: sequence is synthesized

<400> SEQUENCE: 65

Tyr Leu Ser Ser Tyr
 1               5

<210> SEQ ID NO 66
<211> LENGTH: 5
<212> TYPE: PRT
<213> ORGANISM: Artificial sequence
<220> FEATURE:
<223> OTHER INFORMATION: sequence is synthesized

<400> SEQUENCE: 66

Tyr Phe Ser Ser Tyr
 1               5

<210> SEQ ID NO 67
<211> LENGTH: 5
<212> TYPE: PRT
<213> ORGANISM: Artificial sequence
<220> FEATURE:
<223> OTHER INFORMATION: sequence is synthesized

<400> SEQUENCE: 67

Tyr Phe Ser Ser Tyr
 1               5

<210> SEQ ID NO 68
<211> LENGTH: 5
<212> TYPE: PRT
<213> ORGANISM: Artificial sequence
<220> FEATURE:
<223> OTHER INFORMATION: sequence is synthesized

<400> SEQUENCE: 68

Tyr Phe Ser Ser Tyr
 1               5

<210> SEQ ID NO 69
<211> LENGTH: 5
<212> TYPE: PRT
<213> ORGANISM: Artificial sequence
<220> FEATURE:
<223> OTHER INFORMATION: sequence is synthesized

<400> SEQUENCE: 69

Leu Thr His Ser Tyr
 1               5

<210> SEQ ID NO 70
<211> LENGTH: 5
<212> TYPE: PRT
<213> ORGANISM: Artificial sequence
<220> FEATURE:
<223> OTHER INFORMATION: sequence is synthesized

<400> SEQUENCE: 70

Arg Thr His Ser Tyr
 1               5

<210> SEQ ID NO 71
<211> LENGTH: 5
<212> TYPE: PRT
<213> ORGANISM: Artificial sequence
<220> FEATURE:
<223> OTHER INFORMATION: sequence is synthesized

<400> SEQUENCE: 71

Tyr Thr His Ser Tyr
 1               5

<210> SEQ ID NO 72
<211> LENGTH: 5
<212> TYPE: PRT
<213> ORGANISM: Artificial sequence
<220> FEATURE:
<223> OTHER INFORMATION: sequence is synthesized

<400> SEQUENCE: 72

Tyr Thr His Ser Tyr
 1               5

<210> SEQ ID NO 73
<211> LENGTH: 5
<212> TYPE: PRT
<213> ORGANISM: Artificial sequence
<220> FEATURE:
<223> OTHER INFORMATION: sequence is synthesized

<400> SEQUENCE: 73

Trp Thr His Ser Tyr
 1               5

<210> SEQ ID NO 74
<211> LENGTH: 5
<212> TYPE: PRT
<213> ORGANISM: Artificial sequence
<220> FEATURE:
<223> OTHER INFORMATION: sequence is synthesized

<400> SEQUENCE: 74

Trp Val His Ser Tyr
 1               5

<210> SEQ ID NO 75
<211> LENGTH: 6
<212> TYPE: PRT
<213> ORGANISM: Artificial sequence
<220> FEATURE:
<223> OTHER INFORMATION: sequence is synthesized

<400> SEQUENCE: 75

Gly Ala Ser Ser Arg Ala
 1               5

<210> SEQ ID NO 76
<211> LENGTH: 6
<212> TYPE: PRT
<213> ORGANISM: Artificial sequence
<220> FEATURE:
<223> OTHER INFORMATION: sequence is synthesized

<400> SEQUENCE: 76

Gly Ala Ser Arg Arg Ala
1               5

<210> SEQ ID NO 77
<211> LENGTH: 6
<212> TYPE: PRT
<213> ORGANISM: Artificial sequence
<220> FEATURE:
<223> OTHER INFORMATION: sequence is synthesized

<400> SEQUENCE: 77

Gly Ala Ser Arg Arg Glu
1               5

<210> SEQ ID NO 78
<211> LENGTH: 6
<212> TYPE: PRT
<213> ORGANISM: Artificial sequence
<220> FEATURE:
<223> OTHER INFORMATION: sequence is synthesized

<400> SEQUENCE: 78

Gly Ala Ser Ser Arg Ala
1               5

<210> SEQ ID NO 79
<211> LENGTH: 6
<212> TYPE: PRT
<213> ORGANISM: Artificial sequence
<220> FEATURE:
<223> OTHER INFORMATION: sequence is synthesized

<400> SEQUENCE: 79

Gly Ala Ser Arg Arg Ala
1               5

<210> SEQ ID NO 80
<211> LENGTH: 6
<212> TYPE: PRT
<213> ORGANISM: Artificial sequence
<220> FEATURE:
<223> OTHER INFORMATION: sequence is synthesized

<400> SEQUENCE: 80

Gly Ala Ser Ser Arg Glu
1               5

<210> SEQ ID NO 81
<211> LENGTH: 6
<212> TYPE: PRT
<213> ORGANISM: Artificial sequence
<220> FEATURE:
<223> OTHER INFORMATION: sequence is synthesized

<400> SEQUENCE: 81

Gly Ala Ser Ser Gly Glu
1               5

<210> SEQ ID NO 82
<211> LENGTH: 6
<212> TYPE: PRT
<213> ORGANISM: Artificial sequence
<220> FEATURE:
<223> OTHER INFORMATION: sequence is synthesized

<400> SEQUENCE: 82

Gly Ala Ser Arg Arg Glu
1               5

<210> SEQ ID NO 83
<211> LENGTH: 6
<212> TYPE: PRT
<213> ORGANISM: Artificial sequence
<220> FEATURE:
<223> OTHER INFORMATION: sequence is synthesized

<400> SEQUENCE: 83

Gly Ala Ser Ser Arg Ala
1               5

<210> SEQ ID NO 84
<211> LENGTH: 6
<212> TYPE: PRT
<213> ORGANISM: Artificial sequence
<220> FEATURE:
<223> OTHER INFORMATION: sequence is synthesized

<400> SEQUENCE: 84

Gly Ala Ser Ser Ser Ala
1               5

<210> SEQ ID NO 85
<211> LENGTH: 6
<212> TYPE: PRT
<213> ORGANISM: Artificial sequence
<220> FEATURE:
<223> OTHER INFORMATION: sequence is synthesized

<400> SEQUENCE: 85

Gly Ala Ser Ser Arg Ala
1               5

<210> SEQ ID NO 86
<211> LENGTH: 6
<212> TYPE: PRT
<213> ORGANISM: Artificial sequence
<220> FEATURE:
<223> OTHER INFORMATION: sequence is synthesized

<400> SEQUENCE: 86

Gly Ala Ser Arg Arg Ala
1               5

<210> SEQ ID NO 87
<211> LENGTH: 6
<212> TYPE: PRT
<213> ORGANISM: Artificial sequence
<220> FEATURE:
<223> OTHER INFORMATION: sequence is synthesized

<400> SEQUENCE: 87

Gly Ala Ser Ser Arg Ala
1               5

<210> SEQ ID NO 88
<211> LENGTH: 6
<212> TYPE: PRT
<213> ORGANISM: Artificial sequence
<220> FEATURE:
<223> OTHER INFORMATION: sequence is synthesized

<400> SEQUENCE: 88

Gly Ala Ser Ser Ser Glu

```
<210> SEQ ID NO 89
<211> LENGTH: 6
<212> TYPE: PRT
<213> ORGANISM: Artificial sequence
<220> FEATURE:
<223> OTHER INFORMATION: sequence is synthesized

<400> SEQUENCE: 89

Gly Ala Ser Ser Arg Ala
 1               5

<210> SEQ ID NO 90
<211> LENGTH: 6
<212> TYPE: PRT
<213> ORGANISM: Artificial sequence
<220> FEATURE:
<223> OTHER INFORMATION: sequence is synthesized

<400> SEQUENCE: 90

Gly Ala Ser Thr His Glu
 1               5

<210> SEQ ID NO 91
<211> LENGTH: 6
<212> TYPE: PRT
<213> ORGANISM: Artificial sequence
<220> FEATURE:
<223> OTHER INFORMATION: sequence is synthesized

<400> SEQUENCE: 91

Gly Ala Ser Thr Leu Ala
 1               5

<210> SEQ ID NO 92
<211> LENGTH: 6
<212> TYPE: PRT
<213> ORGANISM: Artificial sequence
<220> FEATURE:
<223> OTHER INFORMATION: sequence is synthesized

<400> SEQUENCE: 92

Gly Ala Ser Ser Arg Ala
 1               5

<210> SEQ ID NO 93
<211> LENGTH: 6
<212> TYPE: PRT
<213> ORGANISM: Artificial sequence
<220> FEATURE:
<223> OTHER INFORMATION: sequence is synthesized

<400> SEQUENCE: 93

Gly Ala Ser Ser Arg Ala
 1               5

<210> SEQ ID NO 94
<211> LENGTH: 6
<212> TYPE: PRT
<213> ORGANISM: Artificial sequence
<220> FEATURE:
<223> OTHER INFORMATION: sequence is synthesized

<400> SEQUENCE: 94

Gly Ala Ser Ser Arg Ala
 1               5
```

```
<210> SEQ ID NO 95
<211> LENGTH: 6
<212> TYPE: PRT
<213> ORGANISM: Artificial sequence
<220> FEATURE:
<223> OTHER INFORMATION: sequence is synthesized

<400> SEQUENCE: 95

Gly Ala Ser Ser Arg Ala
 1               5

<210> SEQ ID NO 96
<211> LENGTH: 6
<212> TYPE: PRT
<213> ORGANISM: Artificial sequence
<220> FEATURE:
<223> OTHER INFORMATION: sequence is synthesized

<400> SEQUENCE: 96

Gly Ala Ser Ser Arg Ala
 1               5

<210> SEQ ID NO 97
<211> LENGTH: 6
<212> TYPE: PRT
<213> ORGANISM: Artificial sequence
<220> FEATURE:
<223> OTHER INFORMATION: sequence is synthesized

<400> SEQUENCE: 97

Gly Ala Ser Arg Leu Glu
 1               5

<210> SEQ ID NO 98
<211> LENGTH: 6
<212> TYPE: PRT
<213> ORGANISM: Artificial sequence
<220> FEATURE:
<223> OTHER INFORMATION: sequence is synthesized

<400> SEQUENCE: 98

Gly Ala Ser Ser Arg Ala
 1               5

<210> SEQ ID NO 99
<211> LENGTH: 5
<212> TYPE: PRT
<213> ORGANISM: Artificial sequence
<220> FEATURE:
<223> OTHER INFORMATION: sequence is synthesized

<400> SEQUENCE: 99

Tyr Ser Ser Pro Leu
 1               5

<210> SEQ ID NO 100
<211> LENGTH: 5
<212> TYPE: PRT
<213> ORGANISM: Artificial sequence
<220> FEATURE:
<223> OTHER INFORMATION: sequence is synthesized

<400> SEQUENCE: 100

Ile Gly Ser Pro Ile
 1               5
```

```
<210> SEQ ID NO 101
<211> LENGTH: 5
<212> TYPE: PRT
<213> ORGANISM: Artificial sequence
<220> FEATURE:
<223> OTHER INFORMATION: sequence is synthesized

<400> SEQUENCE: 101

Leu Asn Ser Pro Leu
 1               5

<210> SEQ ID NO 102
<211> LENGTH: 5
<212> TYPE: PRT
<213> ORGANISM: Artificial sequence
<220> FEATURE:
<223> OTHER INFORMATION: sequence is synthesized

<400> SEQUENCE: 102

Ile Val Ser Pro Leu
 1               5

<210> SEQ ID NO 103
<211> LENGTH: 5
<212> TYPE: PRT
<213> ORGANISM: Artificial sequence
<220> FEATURE:
<223> OTHER INFORMATION: sequence is synthesized

<400> SEQUENCE: 103

Leu Arg Ser Pro His
 1               5

<210> SEQ ID NO 104
<211> LENGTH: 5
<212> TYPE: PRT
<213> ORGANISM: Artificial sequence
<220> FEATURE:
<223> OTHER INFORMATION: sequence is synthesized

<400> SEQUENCE: 104

Leu Ser Ser Pro Ile
 1               5

<210> SEQ ID NO 105
<211> LENGTH: 5
<212> TYPE: PRT
<213> ORGANISM: Artificial sequence
<220> FEATURE:
<223> OTHER INFORMATION: sequence is synthesized

<400> SEQUENCE: 105

Ile Ile Ser Pro Ile
 1               5

<210> SEQ ID NO 106
<211> LENGTH: 5
<212> TYPE: PRT
<213> ORGANISM: Artificial sequence
<220> FEATURE:
<223> OTHER INFORMATION: sequence is synthesized

<400> SEQUENCE: 106

Lys Leu Ser Pro Leu
 1               5
```

```
<210> SEQ ID NO 107
<211> LENGTH: 5
<212> TYPE: PRT
<213> ORGANISM: Artificial sequence
<220> FEATURE:
<223> OTHER INFORMATION: sequence is synthesized

<400> SEQUENCE: 107

Lys Ser Ser Pro Arg
 1               5

<210> SEQ ID NO 108
<211> LENGTH: 5
<212> TYPE: PRT
<213> ORGANISM: Artificial sequence
<220> FEATURE:
<223> OTHER INFORMATION: sequence is synthesized

<400> SEQUENCE: 108

Tyr Ser Ser Pro Leu
 1               5

<210> SEQ ID NO 109
<211> LENGTH: 5
<212> TYPE: PRT
<213> ORGANISM: Artificial sequence
<220> FEATURE:
<223> OTHER INFORMATION: sequence is synthesized

<400> SEQUENCE: 109

Tyr Ile Ser Pro Leu
 1               5

<210> SEQ ID NO 110
<211> LENGTH: 5
<212> TYPE: PRT
<213> ORGANISM: Artificial sequence
<220> FEATURE:
<223> OTHER INFORMATION: sequence is synthesized

<400> SEQUENCE: 110

Tyr Gly Thr Pro His
 1               5

<210> SEQ ID NO 111
<211> LENGTH: 5
<212> TYPE: PRT
<213> ORGANISM: Artificial sequence
<220> FEATURE:
<223> OTHER INFORMATION: sequence is synthesized

<400> SEQUENCE: 111

Tyr Arg Ser Pro Leu
 1               5

<210> SEQ ID NO 112
<211> LENGTH: 5
<212> TYPE: PRT
<213> ORGANISM: Artificial sequence
<220> FEATURE:
<223> OTHER INFORMATION: sequence is synthesized

<400> SEQUENCE: 112

Ile Ser Val Pro Leu
 1               5

<210> SEQ ID NO 113
```

```
<211> LENGTH: 5
<212> TYPE: PRT
<213> ORGANISM: Artificial sequence
<220> FEATURE:
<223> OTHER INFORMATION: sequence is synthesized

<400> SEQUENCE: 113

Leu Arg Ser Pro Ile
 1               5

<210> SEQ ID NO 114
<211> LENGTH: 5
<212> TYPE: PRT
<213> ORGANISM: Artificial sequence
<220> FEATURE:
<223> OTHER INFORMATION: sequence is synthesized

<400> SEQUENCE: 114

Ile Arg Ser Pro Leu
 1               5

<210> SEQ ID NO 115
<211> LENGTH: 5
<212> TYPE: PRT
<213> ORGANISM: Artificial sequence
<220> FEATURE:
<223> OTHER INFORMATION: sequence is synthesized

<400> SEQUENCE: 115

Ile Arg Ser Pro Leu
 1               5

<210> SEQ ID NO 116
<211> LENGTH: 5
<212> TYPE: PRT
<213> ORGANISM: Artificial sequence
<220> FEATURE:
<223> OTHER INFORMATION: sequence is synthesized

<400> SEQUENCE: 116

Leu Gly Ser Pro Pro
 1               5

<210> SEQ ID NO 117
<211> LENGTH: 5
<212> TYPE: PRT
<213> ORGANISM: Artificial sequence
<220> FEATURE:
<223> OTHER INFORMATION: sequence is synthesized

<400> SEQUENCE: 117

Tyr Ser Ser Pro Leu
 1               5

<210> SEQ ID NO 118
<211> LENGTH: 5
<212> TYPE: PRT
<213> ORGANISM: Artificial sequence
<220> FEATURE:
<223> OTHER INFORMATION: sequence is synthesized

<400> SEQUENCE: 118

Tyr Gly Ser Pro His
 1               5

<210> SEQ ID NO 119
<211> LENGTH: 5
```

```
<212> TYPE: PRT
<213> ORGANISM: Artificial sequence
<220> FEATURE:
<223> OTHER INFORMATION: sequence is synthesized

<400> SEQUENCE: 119

Tyr Ser Ser Pro Ile
 1               5

<210> SEQ ID NO 120
<211> LENGTH: 5
<212> TYPE: PRT
<213> ORGANISM: Artificial sequence
<220> FEATURE:
<223> OTHER INFORMATION: sequence is synthesized

<400> SEQUENCE: 120

Tyr Ser Ser Pro Val
 1               5

<210> SEQ ID NO 121
<211> LENGTH: 5
<212> TYPE: PRT
<213> ORGANISM: Artificial sequence
<220> FEATURE:
<223> OTHER INFORMATION: sequence is synthesized

<400> SEQUENCE: 121

Phe Ile Ser Pro His
 1               5

<210> SEQ ID NO 122
<211> LENGTH: 5
<212> TYPE: PRT
<213> ORGANISM: Artificial sequence
<220> FEATURE:
<223> OTHER INFORMATION: sequence is synthesized

<400> SEQUENCE: 122

Tyr Gly Thr Pro Ile
 1               5

<210> SEQ ID NO 123
<211> LENGTH: 11
<212> TYPE: PRT
<213> ORGANISM: Artificial sequence
<220> FEATURE:
<223> OTHER INFORMATION: sequence is synthesized

<400> SEQUENCE: 123

Arg Ala Ser Gln Ser Ile Ser Ser Tyr Leu Ala
 1               5                  10

<210> SEQ ID NO 124
<211> LENGTH: 7
<212> TYPE: PRT
<213> ORGANISM: Artificial sequence
<220> FEATURE:
<223> OTHER INFORMATION: sequence is synthesized

<400> SEQUENCE: 124

Gly Ala Ser Ser Arg Ala Ser
 1               5

<210> SEQ ID NO 125
<211> LENGTH: 9
<212> TYPE: PRT
```

```
<213> ORGANISM: Artificial sequence
<220> FEATURE:
<223> OTHER INFORMATION: sequence is synthesized

<400> SEQUENCE: 125

Gln Gln Tyr Met Ser Val Pro Ile Thr
 1               5

<210> SEQ ID NO 126
<211> LENGTH: 10
<212> TYPE: PRT
<213> ORGANISM: Artificial sequence
<220> FEATURE:
<223> OTHER INFORMATION: sequence is synthesized

<400> SEQUENCE: 126

Gly Phe Ser Phe Ser Ser Glu Pro Ile Ser
 1               5                  10

<210> SEQ ID NO 127
<211> LENGTH: 18
<212> TYPE: PRT
<213> ORGANISM: Artificial sequence
<220> FEATURE:
<223> OTHER INFORMATION: sequence is synthesized

<400> SEQUENCE: 127

Ser Ser Ile Thr Gly Lys Asn Gly Tyr Thr Tyr Tyr Ala Asp Ser
 1               5                  10                  15

Val Lys Gly

<210> SEQ ID NO 128
<211> LENGTH: 10
<212> TYPE: PRT
<213> ORGANISM: Artificial sequence
<220> FEATURE:
<223> OTHER INFORMATION: sequence is synthesized

<400> SEQUENCE: 128

Trp Gly Lys Lys Val Tyr Gly Met Asp Val
 1               5                  10

<210> SEQ ID NO 129
<211> LENGTH: 11
<212> TYPE: PRT
<213> ORGANISM: Artificial sequence
<220> FEATURE:
<223> OTHER INFORMATION: sequence is synthesized

<400> SEQUENCE: 129

Arg Ala Ser Gln Tyr Phe Ser Ser Tyr Leu Ala
 1               5                  10

<210> SEQ ID NO 130
<211> LENGTH: 7
<212> TYPE: PRT
<213> ORGANISM: Artificial sequence
<220> FEATURE:
<223> OTHER INFORMATION: sequence is synthesized

<400> SEQUENCE: 130

Gly Ala Ser Ser Arg Ala Ser
 1               5

<210> SEQ ID NO 131
<211> LENGTH: 9
```

```
<212> TYPE: PRT
<213> ORGANISM: Artificial sequence
<220> FEATURE:
<223> OTHER INFORMATION: sequence is synthesized

<400> SEQUENCE: 131

Gln Gln Tyr Leu Gly Ser Pro Pro Thr
 1               5

<210> SEQ ID NO 132
<211> LENGTH: 10
<212> TYPE: PRT
<213> ORGANISM: Artificial sequence
<220> FEATURE:
<223> OTHER INFORMATION: sequence is synthesized

<400> SEQUENCE: 132

Gly Phe Thr Phe Ser Ser Tyr Ala Met Ser
 1               5                  10

<210> SEQ ID NO 133
<211> LENGTH: 18
<212> TYPE: PRT
<213> ORGANISM: Artificial sequence
<220> FEATURE:
<223> OTHER INFORMATION: sequence is synthesized

<400> SEQUENCE: 133

Ser Gln Ile Ser Pro Ala Gly Gly Tyr Thr Asn Tyr Ala Asp Ser
 1               5                  10                  15

Val Lys Gly

<210> SEQ ID NO 134
<211> LENGTH: 13
<212> TYPE: PRT
<213> ORGANISM: Artificial sequence
<220> FEATURE:
<223> OTHER INFORMATION: sequence is synthesized

<400> SEQUENCE: 134

Glu Leu Pro Tyr Tyr Arg Met Ser Lys Val Met Asp Val
 1               5                  10

<210> SEQ ID NO 135
<211> LENGTH: 123
<212> TYPE: PRT
<213> ORGANISM: Artificial sequence
<220> FEATURE:
<223> OTHER INFORMATION: sequence is synthesized

<400> SEQUENCE: 135

Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Thr Phe Ser
                20                  25                  30

Ser Tyr Ala Met Ser Trp Val Arg Gln Ala Pro Gly Lys Gly Leu
                35                  40                  45

Glu Trp Val Ser Gln Ile Ser Pro Ala Gly Gly Tyr Thr Asn Tyr
                50                  55                  60

Ala Asp Ser Val Lys Gly Arg Phe Thr Ile Ser Ala Asp Thr Ser
                65                  70                  75

Lys Asn Thr Ala Tyr Leu Gln Met Asn Ser Leu Arg Ala Glu Asp
                80                  85                  90
```

```
Thr Ala Val Tyr Tyr Cys Ala Arg Gly Glu Leu Pro Tyr Tyr Arg
                95                  100                 105

Met Ser Lys Val Met Asp Val Trp Gly Gln Gly Thr Leu Val Thr
            110                 115                 120

Val Ser Ser
```

NEUROPILIN ANTAGONISTS

CROSS REFERENCE TO RELATED APPLICATIONS

This application is a divisional application of U.S. application Ser. No. 13/489,299, filed Jun. 5, 2012, which is a divisional application of U.S. application Ser. No. 13/173,890, now U.S. Pat. No. 8,211,429, filed Jun. 30, 2011, which is a divisional application of U.S. application Ser. No. 12/107,544, now U.S. Pat. No. 7,994,286, filed Apr. 22, 2008, which is a continuation application of PCT Application No. PCT/US2006/043516 filed Nov. 8, 2006, which claims the benefit of priority under 35 USC 119(e) to U.S. provisional application Nos. 60/734,798 filed Nov. 8, 2005 and 60/820,561, filed Jul. 27, 2006, the entire contents of which are incorporated herein by reference.

SEQUENCE LISTING

The instant application contains a Sequence Listing which has been submitted via EFS-Web and is hereby incorporated by reference in its entirety. Said ASCII copy, created on Dec. 14, 2012, is named P2291R1C1D3SeqList.txt, and is 29,848 bytes in size.

FIELD OF THE INVENTION

The present invention relates generally to compositions and methods associated with neuropilin (NRP) activities. More particularly, the invention pertains to compositions and methods for modulating vacscular formation and maintenance mediated by neuropilin-1 (NRP1) receptor. This invention further relates to methods for the screening of substances therapeutically useful for preventing or treating conditions and diseases associated with angiogenesis.

BACKGROUND OF THE INVENTION

Development of a vascular system is a fundamental requirement for many physiological and pathological processes. Actively growing tissues such as embryos and tumors require adequate blood supply. They satisfy this need by producing pro-angiogenic factors, which promote new blood vessel formation and maintenance via a process generally referred to as angiogenesis. Vascular formation is a complex but orderly biological event involving all or many of the following steps: a) Endothelial cells (ECs) proliferate from existing ECs or differentiate from progenitor cells; b) ECs migrate and coalesce to form cord-like structures; c) vascular cords then undergo tubulogenesis to form vessels with a central lumen d) existing cords or vessels send out sprouts to form secondary vessels; e) primitive vascular plexus undergo further remodeling and reshaping; and f) peri-endothelial cells are recruited to encase the endothelial tubes, providing maintenance and modulatory functions to the vessels; such cells including pericytes for small capillaries, smooth muscle cells for larger vessels, and myocardial cells in the heart. Hanahan, D. Science 277:48-50 (1997); Hogan, B. L. & Kolodziej, P. A. *Nature Reviews Genetics.* 3:513-23 (2002); Lubarsky, B. & Krasnow, M. A. *Cell.* 112:19-28 (2003).

It is now well established that angiogenesis is implicated in the pathogenesis of a variety of disorders. These include solid tumors and metastasis, atherosclerosis, retrolental fibroplasia, hemangiomas, chronic inflammation, intraocular neovascular diseases such as proliferative retinopathies, e.g., diabetic retinopathy, age-related macular degeneration (AMD), neovascular glaucoma, immune rejection of transplanted corneal tissue and other tissues, rheumatoid arthritis, and psoriasis. Folkman et al., *J. Biol. Chem.*, 267:10931-10934 (1992); Klagsbrun et al., *Annu. Rev. Physiol.* 53:217-239 (1991); and Garner A., "Vascular diseases", In: Pathobiology of Ocular Disease. A Dynamic Approach, Garner A., Klintworth G K, eds., 2nd Edition (Marcel Dekker, NY, 1994), pp 1625-1710.

In the case of tumor growth, angiogenesis appears to be crucial for the transition from hyperplasia to neoplasia, and for providing nourishment for the growth and metastasis of the tumor. Folkman et al., *Nature* 339:58 (1989). The neovascularization allows the tumor cells to acquire a growth advantage and proliferative autonomy compared to the normal cells. A tumor usually begins as a single aberrant cell which can proliferate only to a size of a few cubic millimeters due to the distance from available capillary beds, and it can stay 'dormant' without further growth and dissemination for a long period of time. Some tumor cells then switch to the angiogenic phenotype to activate endothelial cells, which proliferate and mature into new capillary blood vessels. These newly formed blood vessels not only allow for continued growth of the primary tumor, but also for the dissemination and recolonization of metastatic tumor cells. Accordingly, a correlation has been observed between density of microvessels in tumor sections and patient survival in breast cancer as well as in several other tumors. Weidner et al., *N. Engl. J. Med* 324:1-6 (1991); Horak et al., *Lancet* 340:1120-1124 (1992); Macchiarini et al., *Lancet* 340:145-146 (1992). The precise mechanisms that control the angiogenic switch is not well understood, but it is believed that neovascularization of tumor mass results from the net balance of a multitude of angiogenesis stimulators and inhibitors (Folkman, 1995, *Nat Med* 1(1): 27-31).

The process of vascular development is tightly regulated. To date, a significant number of molecules, mostly secreted factors produced by surrounding cells, have been shown to regulate EC differentiation, proliferation, migration and coalescence into cord-like structures. For example, vascular endothelial growth factor (VEGF) has been identified as the key factor involved in stimulating angiogenesis and in inducing vascular permeability. Ferrara et al., *Endocr. Rev.* 18:4-25 (1997). The finding that the loss of even a single VEGF allele results in embryonic lethality points to an irreplaceable role played by this factor in the development and differentiation of the vascular system. Furthermore, VEGF has been shown to be a key mediator of neovascularization associated with tumors and intraocular disorders. Ferrara et al., *Endocr. Rev.* supra. The VEGF mRNA is overexpressed by the majority of human tumors examined Berkman et al., *J. Clin. Invest.* 91:153-159 (1993); Brown et al., *Human Pathol.* 26:86-91 (1995); Brown et al., *Cancer Res.* 53:4727-4735 (1993); Mattern et al., *Brit. J. Cancer* 73:931-934 (1996); Dvorak et al., *Am. J. Pathol.* 146:1029-1039 (1995).

Also, the concentration levels of VEGF in eye fluids are highly correlated to the presence of active proliferation of blood vessels in patients with diabetic and other ischemia-related retinopathies. Aiello et al., *N. Engl. J. Med.* 331:1480-1487 (1994). Furthermore, studies have demonstrated the localization of VEGF in choroidal neovascular membranes in patients affected by AMD. Lopez et al., *Invest. Ophthalmol. Vis. Sci.* 37:855-868 (1996).

Anti-VEGF neutralizing antibodies suppress the growth of a variety of human tumor cell lines in nude mice (Kim et al., *Nature* 362:841-844 (1993); Warren et al., *J. Clin. Invest.* 95:1789-1797 (1995); Borgström et al., *Cancer Res.* 56:4032-4039 (1996); Melnyk et al., *Cancer Res.* 56:921-924 (1996)) and also inhibit intraocular angiogenesis in models of ischemic retinal disorders. Adamis et al., *Arch. Ophthalmol.* 114:66-71 (1996). Therefore, anti-VEGF monoclonal antibodies or other inhibitors of VEGF action are promising candidates for the treatment of tumors and various intraocular neovascular disorders. Such antibodies are described, for example, in EP 817,648 published Jan. 14, 1998; and in WO98/45331 and WO98/45332, both published Oct. 15, 1998. One of the anti-VEGF antibodies, bevacizumab, has been approved by the FDA for use in combination with a chemotherapy regimen to treat metastatic colorectal cancer (CRC) and non-samll cell lung cancer (NSCLC). And bevacizumab is being investigated in many ongoing clinical trials for treating various cancer indications.

During development of the nervous system, neurons send out cable-like axons that migrate over long distances in order to reach their targets. See review by Carmeliet and Tessier-Lavigne (2005) *Nature* 436:193-200. At the leading tip of a growing axon is a highly motile, sensory structure called growth cone. Through dynamic cycles of extension and retraction of filopodial extensions, the growth cone continually senses and asseses from a myriad of guidance cues in its spatial environment, and accurately selects a correct track for extension towards its final target.

Over the past decade, considerable progress has been made in understanding axon guidance mechanisms. See review by Dickson (2002) *Science* 298:1959-64. Guidance cues come in four varieties: attractants and repellents; which may act either at short range (i.e., cell- or matrix-associated) or at longer range (i.e., diffusible). So far, four major families of axon guidance molecules have been identified: the netrins, semaphorins, ephrins and slits. See review by Huber et al (2003) *Annu Rev Neurosci* 26:509-63.

The semaphorins (Sema), also called collapsins, belong to a large family of phylogenetically conserved secreted and membrane-associated proteins. Members of the semaphorin family are capable of mediating both repulsive and attractive axon guidance events during neural development. Raper (2000) *Curr Opin Neurobiol* 10:88-94. The more than thirty semaphorins identified to date all share a conserved N-terminal Sema domain of about 500 amino acids. Semaphorin members are classified into eight subfamilies depending on their structural similarities and species of origin. For more details on unified nomenclature for semaphorins, see Semaphorin Nomenclature Committee (1999) *Cell* 97:551-552.

The neuropilin (NRP) family is comprised of two homologous proteins, neuropilin-1 (NRP1) and neuropilin-2 (NRP2). NRP1 was first identified as a type 1 130-kDa transmembrane glycoprotein expressed in growth cones of growing axons. NRP2 was subsequently identified by expression cloning. Fujisawa and Kitsukawa (1998) *Curr Opin Neurobiol* 8:587-592. NRPs are found to be receptors for a subset of semaphorins, the class 3 semaphorins. It was suggested that NRPs function as non-signaling co-receptors along with another semaphorin receptor family, plexins.

Although initially described as a mediator of axon guidance, NRPs have also been found to play critical roles in vascular development. Carmeliet and Tessier-Lavigne (2005). It is identified as an isoform-specific VEGF receptor expressed on tumor and endothelial cells, prompting considerable efforts to understand the role of NRPs in vascular and tumor biology. Soker et al (1998) *Cell* 92:735-745; Klagsbrun et al (2002) *Adv Exp Med Biol* 515:33-48. Genetic studies have provided strong evidence that Nrp1 is required for vascular morphogenesis. Loss of Nrp1 function results in vascular remodeling and branching defects, a phenotype that can be further enhanced by the loss of Nrp2 function. Kawasaki et al. (1999) Development 126:4895-4902; Takashima et al. (2002) *Proc Natl Acad Sci USA* 99:3657-3662. These results suggest that early in development Nrp1 and Nrp2 may have overlapping functions. However, the expression of each Nrp is partitioned later in development, with Nrp1 being expressed primarily in arteries, and Nrp2 in veins and lymphatic vessels. Yuan et al (2002) *Development* 129:4797-4806; Herzog et al. (2001) *Mech Dev* 109:115-119. Notably, loss of Nrp2 function alone specifically impairs lymphatic development.

As Nrp1 is expressed in many other cell types during development, the role of vascular Nrp1 was addressed through the generation of an EC-specific knock-out, which resulted in similar vascular defects to those seen in the null allele. Gu et al. (2003) *Dev Cell* 5:45-57. Interestingly, this study also showed that Sema3A binding to NRP1 is not required for vascular development. In another study, defects were observed in the guidance of endothelial tip cells in the developing hindbrain in Nrp1 KO embryos. Gerhardt et al. (2004) *Dev Dyn* 231:503-509.

Despite the extensive studies in NRP1's role in vascular development, it remains unclear as to whether NRP1 exerts its vascular function exclusively via the VEGF-VEGF Receptor 2 (VEGFR2) pathway, as an enhancer for VEGF binding to VEGFR2 and thereby for VEGFR2 signaling, or via a signaling pathway independent of VEGFR2, or a combination of both.

Monoclonal antibodies can be manufactured using recombinant DNA technology. Widespread use has been made of monoclonal antibodies, particularly those derived from rodents, however nonhuman antibodies are frequently antigenic in humans. The art has attempted to overcome this problem by constructing "chimeric" antibodies in which a nonhuman antigen-binding domain is coupled to a human constant domain (Cabilly et al., U.S. Pat. No. 4,816,567). The isotype of the human constant domain may be selected to tailor the chimeric antibody for participation in antibody-dependent cellular cytotoxicity (ADCC) and complement-dependent cytotoxicity. In a further effort to resolve the antigen binding functions of antibodies and to minimize the use of heterologous sequences in human antibodies, humanized antibodies have been generated for various antigens in which substantially less than an intact human variable domain has been substituted at regions by the corresponding sequence from a non-human species. For example, rodent residues have been substituted for the corresponding segments of a human antibody. In practice, humanized antibodies are typically human antibodies in which some complementarity determining region (CDR) residues and possibly some framework region (FR) residues are substituted by residues from analogous sites in rodent antibodies. Jones et al. (1986) *Nature* 321:522-525; Riechmann et al. (1988) *Nature* 332:323-327; Verhoeyen et al. (1988) *Science* 239:1534-1536.

Prior to administering a therapeutic antibody to human, preclinical studies in nonhuman mammals are generally desired to evaluate the efficacy and/or toxicity of the antibody. Ideally, the antibodies subject to these studies are capable of recognizing and reacting with high potency to a target antigen endogenous to the host animal such as mouse or nonhuman primate.

Phage display technology has provided a powerful tool for generating and selecting novel proteins that bind to a ligand, such as an antigen. Using the technique of phage display, large libraries of protein variants can be generated and rapidly sorted for those sequences that bind to a target antigen with high affinity. Nucleic acids encoding variant polypeptides are fused to a nucleic acid sequence encoding a viral coat protein, such as the gene III protein or the gene VIII protein. Monovalent phage display systems where the nucleic acid sequence encoding the protein or polypeptide is fused to a nucleic acid sequence encoding a portion of the gene III protein have been developed. (Bass, S. (1990) *Proteins* 8:309; Lowman and Wells (1991) *Methods: A Companion to Methods in Enzymology* 3:205). In a monovalent phage display system, the gene fusion is expressed at low levels and wild type gene III proteins are also expressed so that infectivity of the particles is retained. Methods of generating peptide libraries and screening those libraries have been disclosed in many patents (e.g., U.S. Pat. No. 5,723,286, U.S. Pat. No. 5,432,018, U.S. Pat. No. 5,580,717, U.S. Pat. No. 5,427,908 and U.S. Pat. No. 5,498,530).

The demonstration of expression of peptides on the surface of filamentous phage and the expression of functional antibody fragments in the periplasm of *E. coli* was important in the development of antibody phage display libraries. (Smith et al. (1985) *Science* 228:1315; Skerra and Pluckthun (1988) *Science* 240:1038). Libraries of antibodies or antigen binding polypeptides have been prepared in a number of ways including by altering a single gene by inserting random DNA sequences or by cloning a family of related genes. Methods for displaying antibodies or antigen binding fragments using phage display have been described in U.S. Pat. Nos. 5,750,373, 5,733,743, 5,837,242, 5,969,108, 6,172,197, 5,580,717, and 5,658,727. The library is then screened for expression of antibodies or antigen binding proteins with desired characteristics.

Phage display technology has several advantages over conventional hybridoma and recombinant methods for preparing antibodies with the desired characteristics. This technology allows the development of large libraries of antibodies with diverse sequences in less time and without the use of animals. Preparation of hybridomas or preparation of humanized antibodies can easily require several months of preparation. In addition, since no immunization is required, phage antibody libraries can be generated for antigens which are toxic or have low antigenicity (Hogenboom (1988) *Immunotechniques* 4:1-20). Phage antibody libraries can also be used to generate and identify novel therapeutic antibodies.

Phage display libraries have been used to generate human antibodies from immunized, non-immunized humans, germ line sequences, or naïve B cell Ig repertoires (Barbas & Burton (1996) *Trends Biotech* 14:230; Griffiths et al. (1994) *EMBO J.* 13:3245; Vaughan et al. (1996) *Nat. Biotech.* 14:309; Winter EP 0368 684 B1). Naïve, or nonimmune, antigen binding libraries have been generated using a variety of lymphoidal tissues. Some of these libraries are commercially available, such as those developed by Cambridge Antibody Technology and Morphosys (Vaughan et al. (1996) *Nature Biotech* 14:309; Knappik et al. (1999) *J. Mol. Biol.* 296:57). However, many of these libraries have limited diversity.

The ability to identify and isolate high affinity antibodies from a phage display library is important in isolating novel antibodies for therapeutic use. Isolation of high affinity antibodies from a library is dependent on the size of the library, the efficiency of production in bacterial cells and the diversity of the library. See, for e.g., Knappik et al. (1999) *J. Mol. Biol.* 296:57. The size of the library is decreased by inefficiency of production due to improper folding of the antibody or antigen binding protein and the presence of stop codons. Expression in bacterial cells can be inhibited if the antibody or antigen binding domain is not properly folded. Expression can be improved by mutating residues in turns at the surface of the variable/constant interface, or at selected CDR residues. (Deng et al. (1994) *J. Biol. Chem.* 269:9533, Ulrich et al. (1995) *PNAS*, 92:11907-11911; Forsberg et al. (1997) *J. Biol. Chem.* 272:12430). The sequence of the framework region is a factor in providing for proper folding when antibody phage libraries are produced in bacterial cells.

Generating a diverse library of antibodies or antigen binding proteins is also important to isolation of high affinity antibodies. Libraries with diversification in limited CDRs have been generated using a variety of approaches. See, e.g., Tomlinson (2000) *Nature Biotech.* 18:989-994. CDR3 regions are of interest in part because they often are found to participate in antigen binding. CDR3 regions on the heavy chain vary greatly in size, sequence and structural conformation.

Others have also generated diversity by randomizing CDR regions of the variable heavy and light chains using all 20 amino acids at each position. It was thought that using all 20 amino acids would result in a large diversity of sequences of variant antibodies and increase the chance of identifying novel antibodies. (Barbas (1994) *PNAS* 91:3809; Yelton, D E (1995) *J. Immunology* 155:1994; Jackson, J. R. (1995) *J. Immunology* 154:3310 and Hawkins, R E (1992) *J. Mol. Biology.* 226:889).

SUMMARY OF THE INVENTION

The present invention provides novel anti-NRP1 antibodies capable of modulating at least one neuropilin mediated biological activity. Preferably, the anti-NRP1 antibodies are antagonist antibodies capable of inhibiting at least one neuropilin mediated biological activity. More specifically, the present invention provides methods of generating anti-NRP1 antibodies from a designed human synthetic antibody phage library, and novel function blocking anti-NRP1 antibodies generated thereof. The anti-NRP1 antibodies of the invention fall into two classes, depending on where they bind to on NRP1: anti-NRP1$^A$ antibodies (including YW64.3 and variants thereof) are those that bind to the CUB domains (a1a2) of NRP1; and anti-NRP1$^B$ antibodies (including YW107.4 and variants thereof) are those that bind to the coagulation factor V/VIII domains (b1b2) of NRP1.

In one aspect, the anti-NRP1$^A$ antibodies of the invention can be selected from the "YW64" antibody clones as shown in Table III, having the identified partial CDR sequences and binding affinities to murine and human NRP1 s. The anti-NRP1$^A$ antibody of the invention preferably comprises a light chain variable domain comprising the following CDR amino acid sequences: CDRL1 (RASQSISSYLA; SEQ ID NO:123), CDRL2 (GASSRAS; SEQ ID NO:124) and CDRL3 (QQYMSVPIT; SEQ ID NO:125). For example, the anti-NRP1$^A$ antibody comprises a light chain variable domain sequence of SEQ ID NO:3. The anti-NRP1$^A$ antibody of the invention preferably comprises a heavy chain variable domain comprising the following CDR amino acid sequences: CDRH1 (GFSFSSEPIS; SEQ ID NO:126), CDRH2 (SSITGKNGYTYYADSVKG; SEQ ID NO:127) and CDRH3 (WGKKVYGMDV; SEQ ID NO:128). For example, the anti-NRP1$^A$ antibody comprises a heavy chain variable domain sequence of SEQ ID NO:4. More preferably, the anti-NRP1$^A$ antibody of the invention is the YW64.3 antibody comprising a light chain variable domain sequence of SEQ ID NO:3 and a heavy chain variable domain sequence of SEQ ID NO:4.

In another aspect, the anti-NRP1$^B$ antibodies of the invention can be selected from the "YW107.4" antibody clones as shown in Table IV, having the identified partial CDR sequences and binding affinities to murine and human NRP1 s. The anti-NRP1$^B$ antibody of the invention preferably comprises a light chain variable domain comprising the following CDR amino acid sequences: CDRL1 (RASQYFSSYLA; SEQ ID NO:129), CDRL2 (GASSRAS; SEQ ID NO:130) and CDRL3 (QQYLGSPPT; SEQ ID NO:131). For example, the anti-NRP1$^B$ antibody comprises a light chain variable domain sequence of SEQ ID NO:5. The anti-NRP1$^B$ antibody of the invention preferably comprises a heavy chain variable domain comprising the following CDR amino acid sequences: CDRH1 (GFTFSSYAMS; SEQ ID NO:132), CDRH2 (SQISPAGGYTNYADSVKG; SEQ ID NO:133) and CDRH3 (ELPYYRMSKVMDV; SEQ ID NO:134). For example, the anti-NRP1$^B$ antibody comprises a heavy chain variable domain sequence of SEQ ID NO:6. More preferably, the anti-NRP1$^B$ antibody of the invention is the YW107.4.87 antibody comprising a light chain variable domain sequence of SEQ ID NO:5 and a heavy chain variable domain sequence of SEQ ID NO:6.

Also provided by the present invention are uses of the anti-NRP1 antibodies for treating angiogenesis associated disorders such as cancer. In one preferred embodiment, the anti-NRP1 antibodies of invention are used in combination with an anti-VEGF antibody. Preferably, the anti-VEGF antibody is capable of binding to the same VEGF epitope as the antibody A4.6.1. More preferably, the anti-VEGF antibody is bevacizumab or ranibizumab.

BRIEF DESCRIPTION OF THE DRAWINGS

FIG. 3 shows the variable region sequences of YW 64.3 (anti-NRP1$^A$) and YW107.4.87 (anti-NRP1$^B$), with the sequences of h4D5 listed as reference. The numbering is based on Kabat database. The CDR sequences are in box region. (3A) Light chain variable region sequences for h4D5 (SEQ ID NO:1), YW 64.3 (SEQ ID NO:3) and YW107.4.87 (SEQ ID NO:5). (3B) Heavy chain variable region sequences for h4D5 (SEQ ID NO:2), YW 64.3 (SEQ ID NO:4) and YW107.4.87 (SEQ ID NO:6).

DETAILED DESCRIPTION OF THE INVENTION

Figure 1A:
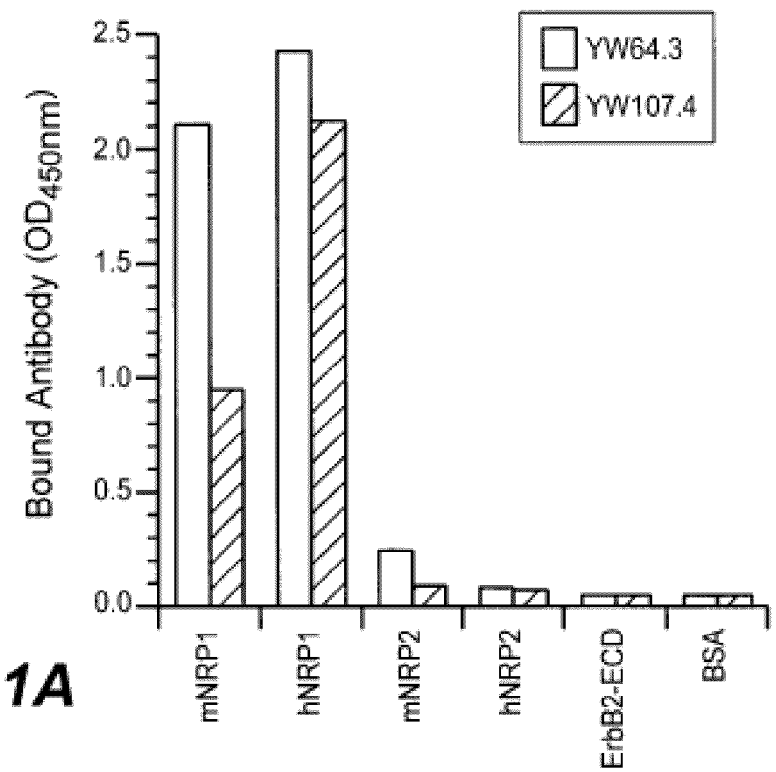
FIG. 1 illustrates binding specificities of anti-NRP1 antibodies. (1A) Anti-NRP1 antibodies bind specifically to human and murine NRP1. Binding specificities of anti-NRP1 antibodies YW64.3 and YW107.4 IgGs (10 ug/ml) were evaluated by testing binding to hNRP1-, mNRP1-, hNRP2-, mNRP2-, ErbB2-ECD-, or BSA-coated wells, and bound IgGs were detected by anti-human IgG HRP conjugates. (1B) FACS analysis of anti-NRP1 antibodies YW64.3 and YW107.4 IgGs showing antibody binding capability to cell surface NRP1 protein (HUVECs).

The present invention relates to novel compositions and methods for modulating NRP mediated biological activities.

DEFINITIONS

"Neuropilin" or NRP refers collectively to neuropilin-1 (NRP1), neuropilin-2 (NRP2) and their isoforms and variants, as described in Rossignol et al. (2000) *Genomics* 70:211-222. Neuropilins are 120 to 130 kDa non-tyrosine kinase receptors. There are multiple NRP-1 and NRP-2 splice variants and soluble isoforms. The basic structure of neuropilins comprises five domains: three extracellular domains (a1a2, b1b2 and c), a transmembrane domain, and a cytoplasmic domain. The a1a2 domain is homologous to complement components C1r and C1s (CUB), which generally contains four cysteine residues that form two disculfid bridges. The b1b2 domain is homologous to coagulation factors V and VIII. The central portion of the c domain is designated as MAM due to its homology to meprin, A5 and receptor tyrosine phosphotase µ proteins. The a1a2 and b1b2 domains are responsible for ligand binding, whereas the c domain is critical for homodimerization or heterodimerization. Gu et al. (2002) *J. Biol. Chem.* 277:18069-76; He and Tessier-Lavigne (1997) *Cell* 90:739-51.

"Neuropilin mediated biological activity" refers in general to physiological or pathological events in which neuropilin-1 and/or neuropilin-2 plays a substantial role. Non-limiting examples of such activities are axon guidance during embryonic nervous system development or neuron-regeneration, angiogenesis (including vascular modeling), tumorgenesis and tumor metastasis.

The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) *Nature* 256: 495, or may be made by recombinant DNA methods (see, e.g., U.S. Pat. No. 4,816,567). The "monoclonal antibodies" may also be isolated from phage antibody libraries using the techniques described in Clackson et al. (1991) *Nature* 352:624-628 and Marks et al. (1991) *J. Mol. Biol.* 222:581-597, for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al. (1984) *Proc. Natl. Acad. Sci. USA* 81:6851-6855).

"Humanized" forms of non-human (e.g., murine) antibodies are chimeric antibodies which contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al. (1986) *Nature* 321:522-525; Riechmann et al. (1988) *Nature* 332:323-329; and Presta (1992) *Curr. Op. Struct. Biol.* 2:593-596.

A "species-dependent antibody" is one which has a stronger binding affinity for an antigen from a first mammalian species than it has for a homologue of that antigen from a second mammalian species. Normally, the species-dependent antibody "binds specifically" to a human antigen (i.e. has a binding affinity ($K_d$) value of no more than about $1 \times 10^{-7}$ M, preferably no more than about $1 \times 10^{-8}$ M and most preferably no more than about $1 \times 10^{-9}$ M) but has a binding affinity for a homologue of the antigen from a second nonhuman mammalian species which is at least about 50 fold, or at least about 500 fold, or at least about 1000 fold, weaker than its binding affinity for the human antigen. The species-dependent antibody can be any of the various types of antibodies as defined above, but preferably is a humanized or human antibody.

As used herein, "antibody mutant" or "antibody variant" refers to an amino acid sequence variant of the species-dependent antibody wherein one or more of the amino acid residues of the species-dependent antibody have been modified. Such mutants necessarily have less than 100% sequence identity or similarity with the species-dependent antibody. In a preferred embodiment, the antibody mutant will have an amino acid sequence having at least 75% amino acid sequence identity or similarity with the amino acid sequence of either the heavy or light chain variable domain of the species-dependent antibody, more preferably at least 80%, more preferably at least 85%, more preferably at least 90%, and most preferably at least 95%. Identity or similarity with respect to this sequence is defined herein as the percentage of amino acid residues in the candidate sequence that are identical (i.e same residue) or similar (i.e. amino acid residue from the same group based on common side-chain properties, see below) with the species-dependent antibody residues, after aligning the sequences and introducing gaps, if necessary, to achieve the maximum percent sequence identity. None of N-terminal, C-terminal, or internal extensions, deletions, or insertions into the antibody sequence outside of the variable domain shall be construed as affecting sequence identity or similarity.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

As used herein, "antibody variable domain" refers to the portions of the light and heavy chains of antibody molecules that include amino acid sequences of Complementarity Determining Regions (CDRs; ie., CDR1, CDR2, and CDR3), and Framework Regions (FRs). $V_H$ refers to the variable domain of the heavy chain. $V_L$ refers to the variable domain of the light chain. According to the methods used in this invention, the amino acid positions assigned to CDRs and FRs may be defined according to Kabat (Sequences of Proteins of Immunological Interest (National Institutes of Health, Bethesda, Md., 1987 and 1991)) Amino acid numbering of antibodies or antigen binding fragments is also according to that of Kabat.

As used herein, the term "Complementarity Determining Regions (CDRs; ie., CDR1, CDR2, and CDR3) refers to the amino acid residues of an antibody variable domain the presence of which are necessary for antigen binding. Each variable domain typically has three CDR regions identified as CDR1, CDR2 and CDR3. Each complementarity determining region may comprise amino acid residues from a "complementarity determining region" as defined by Kabat (i.e. about residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest*, 5th Ed. Public Health Service, National Institutes of Health, Bethesda, Md. (1991)) and/or those residues from a "hypervariable loop" (i.e. about residues 26-32 (L1), 50-52 (L2) and 91-96 (L3) in the light chain variable domain and 26-32 (H1), 53-55 (H2) and 96-101 (H3) in the heavy chain variable domain; Chothia and Lesk (1987) *J. Mol. Biol.* 196:901-917). In some instances, a complementarity determining region can include amino acids from both a CDR region defined according to Kabat and a hypervariable loop. For example, the CDRH1 of the heavy chain of antibody 4D5 includes amino acids 26 to 35.

"Framework regions" (hereinafter FR) are those variable domain residues other than the CDR residues. Each variable domain typically has four FRs identified as FR1, FR2, FR3 and FR4. If the CDRs are defined according to Kabat, the light chain FR residues are positioned at about residues 1-23 (LCFR1), 35-49 (LCFR2), 57-88 (LCFR3), and 98-107 (LCFR4) and the heavy chain FR residues are positioned about at residues 1-30 (HCFR1), 36-49 (HCFR2), 66-94 (HCFR3), and 103-113 (HCFR4) in the heavy chain residues. If the CDRs comprise amino acid residues from hypervariable loops, the light chain FR residues are positioned about at residues 1-25 (LCFR1), 33-49 (LCFR2), 53-90 (LCFR3), and 97-107 (LCFR4) in the light chain and the heavy chain FR residues are positioned about at residues 1-25 (HCFR1), 33-52 (HCFR2), 56-95 (HCFR3), and 102-113 (HCFR4) in the heavy chain residues. In some instances, when the CDR comprises amino acids from both a CDR as defined by Kabat and those of a hypervariable loop, the FR residues will be adjusted accordingly. For example, when CDRH1 includes amino acids H26-H35, the heavy chain FR1 residues are at positions 1-25 and the FR2 residues are at positions 36-49.

As used herein, "codon set" refers to a set of different nucleotide triplet sequences used to encode desired variant amino acids. A set of oligonucleotides can be synthesized, for example, by solid phase synthesis, including sequences that represent all possible combinations of nucleotide triplets provided by the codon set and that will encode the desired group of amino acids. A standard form of codon designation is that of the IUB code, which is known in the art and described herein. A codon set typically is represented by 3 capital letters in italics, eg. NNK, NNS, XYZ, DVK and the like. A "non-random codon set", as used herein, thus refers to a codon set that encodes select amino acids that fulfill partially, preferably completely, the criteria for amino acid selection as described herein. Synthesis of oligonucleotides with selected nucleotide "degeneracy" at certain positions is well known in that art, for example the TRIM approach (Knappek et al. (1999) *J. Mol. Biol.* 296:57-86); Garrard & Henner (1993) *Gene* 128:103). Such sets of oligonucleotides having certain codon sets can be synthesized using commercial nucleic acid synthesizers (available from, for example, Applied Biosystems, Foster City, Calif.), or can be obtained commercially (for example, from Life Technologies, Rockville, Md.). Therefore, a set of oligonucleotides synthesized having a particular codon set will typically include a plurality of oligonucleotides with different sequences, the differences established by the codon set within the overall sequence. Oligonucleotides, as used according to the invention, have sequences that allow for hybridization to a variable domain nucleic acid template and also can, but does not necessarily, include restriction enzyme sites useful for, for example, cloning purposes.

An "Fv" fragment is an antibody fragment which contains a complete antigen recognition and binding site. This region consists of a dimer of one heavy and one light chain variable domain in tight association, which can be covalent in nature, for example in scFv. It is in this configuration that the three CDRs of each variable domain interact to define an antigen binding site on the surface of the $V_H$-$V_L$ dimer. Collectively, the six CDRs or a subset thereof confer antigen binding specificity to the antibody. However, even a single variable domain (or half of an Fv comprising only three CDRs specific for an antigen) has the ability to recognize and bind antigen, although usually at a lower affinity than the entire binding site.

The "Fab" fragment contains a variable and constant domain of the light chain and a variable domain and the first constant domain (CH1) of the heavy chain. F(ab')$_2$ antibody fragments comprise a pair of Fab fragments which are generally covalently linked near their carboxy termini by hinge cysteines between them. Other chemical couplings of antibody fragments are also known in the art.

"Single-chain Fv" or "scFv" antibody fragments comprise the $V_H$ and $V_L$ domains of antibody, wherein these domains are present in a single polypeptide chain. Generally the Fv polypeptide further comprises a polypeptide linker between the $V_H$ and $V_L$ domains, which enables the scFv to form the desired structure for antigen binding. For a review of scFv, see Pluckthun in *The Pharmacology of Monoclonal Antibodies*, Vol 113, Rosenburg and Moore eds. Springer-Verlag, New York, pp. 269-315 (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$ and $V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al. (1993) *Proc. Natl. Acad. Sci. USA* 90:6444-6448.

The expression "linear antibodies" refers to the antibodies described in Zapata et al. (1995 *Protein Eng*, 8(10):1057-1062). Briefly, these antibodies comprise a pair of tandem Fd segments ($V_H$-$C_H$1-$V_H$-$C_H$1) which, together with complementary light chain polypeptides, form a pair of antigen binding regions. Linear antibodies can be bispecific or monospecific.

As used herein, "library" refers to a plurality of antibody or antibody fragment sequences (for example, polypeptides of the invention), or the nucleic acids that encode these sequences, the sequences being different in the combination of variant amino acids that are introduced into these sequences according to the methods of the invention.

"Phage display" is a technique by which variant polypeptides are displayed as fusion proteins to at least a portion of coat protein on the surface of phage, e.g., filamentous phage, particles. A utility of phage display lies in the fact that large libraries of randomized protein variants can be rapidly and efficiently sorted for those sequences that bind to a target antigen with high affinity. Display of peptide and protein libraries on phage has been used for screening millions of polypeptides for ones with specific binding properties. Polyvalent phage display methods have been used for displaying small random peptides and small proteins through fusions to either gene III or gene VIII of filamentous phage. Wells and Lowman (1992) *Curr. Opin. Struct. Biol.* 3:355-362, and references cited therein. In a monovalent phage display, a protein or peptide library is fused to a gene III or a portion thereof, and expressed at low levels in the presence of wild type gene III protein so that phage particles display one copy or none of the fusion proteins. Avidity effects are reduced relative to polyvalent phage so that sorting is on the basis of intrinsic ligand affinity, and phagemid vectors are used, which simplify DNA manipulations. Lowman and Wells (1991) *Methods: A companion to Methods in Enzymology* 3:205-0216.

A "phagemid" is a plasmid vector having a bacterial origin of replication, e.g., Co1E1, and a copy of an intergenic region of a bacteriophage. The phagemid may be used on any known bacteriophage, including filamentous bacteriophage and lambdoid bacteriophage. The plasmid will also generally contain a selectable marker for antibiotic resistance. Segments of DNA cloned into these vectors can be propagated as plasmids. When cells harboring these vectors are provided with all genes necessary for the production of phage particles, the mode of replication of the plasmid changes to rolling circle replication to generate copies of one strand of the plasmid DNA and package phage particles. The phagemid may form infectious or non-infectious phage particles. This term includes phagemids which contain a phage coat protein gene or fragment thereof linked to a heterologous polypeptide gene as a gene fusion such that the heterologous polypeptide is displayed on the surface of the phage particle.

The term "phage vector" means a double stranded replicative form of a bacteriophage containing a heterologous gene and capable of replication. The phage vector has a phage origin of replication allowing phage replication and phage particle formation. The phage is preferably a filamentous bacteriophage, such as an M13, fl, fd, Pf3 phage or a derivative thereof, or a lambdoid phage, such as lambda, 21, phi80, phi81, 82, 424, 434, etc., or a derivative thereof.

As used herein, "solvent accessible position" refers to a position of an amino acid residue in the variable regions of the heavy and light chains of a source antibody or antigen binding fragment that is determined, based on structure, ensemble of structures and/or modeled structure of the antibody or antigen binding fragment, as potentially available for solvent access and/or contact with a molecule, such as an antibody-specific antigen. These positions are typically found in the CDRs and on the exterior of the protein. The solvent accessible positions of an antibody or antigen binding fragment, as defined herein, can be determined using any of a number of algorithms known in the art. Preferably, solvent accessible positions are determined using coordinates from a 3-dimensional model of an antibody, preferably using a computer program such as the InsightII program (Accelrys, San Diego, Calif.). Solvent accessible positions can also be determined using algorithms known in the art (e.g., Lee and Richards (1971) *J. Mol. Biol.* 55, 379 and Connolly (1983) *J. Appl. Cryst.* 16, 548). Determination of solvent accessible positions can be performed using software suitable for protein modeling and 3-dimensional structural information obtained from an antibody. Software that can be utilized for these purposes includes SYBYL Biopolymer Module software (Tripos Associates). Generally and preferably, where an algorithm (program) requires a user input size parameter, the "size" of a probe which is used in the calculation is set at about 1.4 Angstrom or smaller in radius. In addition, determination of solvent accessible regions and area methods using software for personal computers has been described by Pacios (1994) *Comput. Chem.* 18(4): 377-386.

An "angiogenic factor or agent" is a growth factor which stimulates the development of blood vessels, e.g., promote angiogenesis, endothelial cell growth, stabiliy of blood vessels, and/or vasculogenesis, etc. For example, angiogenic factors, include, but are not limited to, e.g., VEGF and members of the VEGF family, PlGF, PDGF family, fibroblast growth factor family (FGFs), TIE ligands (Angiopoietins), ephrins, Del-1, fibroblast growth factors: acidic (aFGF) and basic (bFGF), Follistatin, Granulocyte colony-stimulating factor (G-CSF), Hepatocyte growth factor (HGF)/scatter factor (SF), Interleukin-8 (IL-8), Leptin, Midkine, neuropilins, Placental growth factor, Platelet-derived endothelial cell growth factor (PD-ECGF), Platelet-derived growth factor, especially PDGF-BB or PDGFR-beta, Pleiotrophin (PTN), Progranulin, Proliferin, Transforming growth factor-alpha (TGF-alpha), Transforming growth factor-beta (TGF-beta), Tumor necrosis factor-alpha (TNF-alpha), etc. It would also include factors that accelerate wound healing, such as growth hormone, insulin-like growth factor-I (IGF-I), VIGF, epidermal growth factor (EGF), CTGF and members of its family, and TGF-alpha and TGF-beta. See, e.g., Klagsbrun and D'Amore (1991) *Annu. Rev. Physiol.* 53:217-39; Streit and Detmar (2003) *Oncogene* 22:3172-3179; Ferrara & Alitalo (1999) *Nature Medicine* 5(12):1359-1364; Tonini et al. (2003) *Oncogene* 22:6549-6556 (e.g., Table 1 listing known angiogenic factors); and, Sato (2003) *Int. J. Clin. Oncol.* 8:200-206.

An "anti-angiogenesis agent" or "angiogenesis inhibitor" refers to a small molecular weight substance, an polynucleotide, an polypeptide, an isolated protein, a recombinant protein, an antibody, or conjugates or fusion proteins thereof, that inhibits angiogenesis, vasculogenesis, or undesirable vascular permeability, either directly or indirectly. It should be understood that theanti-angiogenesis agent includes those agents that bind and block the angiogenic activity of the angiogenic factor or its receptor. For example, an anti-angiogenesis agent is an antibody or other antagonist to an angiogenic agent as defined above, e.g., antibodies to VEGF-A or to the VEGF-A receptor (e.g., KDR receptor or Flt-1 receptor), anti-PDGFR inhibitors such as Gleevec™ (Imatinib Mesylate). Anti-angiogensis agents also include native angiogenesis inhibitors, e.g., angiostatin, endostatin, etc. See, e.g., Klagsbrun and D'Amore (1991) *Annu. Rev. Physiol.* 53:217-39; Streit and Detmar (2003) *Oncogene* 22:3172-3179 (e.g., Table 3 listing anti-angiogenic therapy in malignant melanoma); Ferrara & Alitalo (1999) *Nature Medicine* 5(12): 1359-1364; Tonini et al. (2003) *Oncogene* 22:6549-6556 (e.g., Table 2 listing known antiangiogenic factors); and, Sato (2003) *Int. J. Clin. Oncol.* 8:200-206 (e.g., Table 1 listing anti-angiogenic agents used in clinical trials).

The term "VEGF" or "VEGF-A" as used herein refers to the 165-amino acid human vascular endothelial cell growth factor and related 121-, 189-, and 206-amino acid human vascular endothelial cell growth factors, as described by Leung et al. (1989) *Science* 246:1306, and Houck et al. (1991) *Mol. Endocrin,* 5:1806, together with the naturally occurring allelic and processed forms thereof. The term "VEGF" also refers to VEGFs from non-human species such as mouse, rat or primate. Sometimes the VEGF from a specific species are indicated by terms such as hVEGF for human VEGF, mVEGF for murine VEGF, and etc. The term "VEGF" is also used to refer to truncated forms of the polypeptide comprising amino acids 8 to 109 or 1 to 109 of the 165-amino acid human vascular endothelial cell growth factor. Reference to any such forms of VEGF may be identified in the present application, e.g., by "VEGF (8-109)," "VEGF (1-109)" or "VEGF$_{165}$." The amino acid positions for a "truncated" native VEGF are numbered as indicated in the native VEGF sequence. For example, amino acid position 17 (methionine) in truncated native VEGF is also position 17 (methionine) in native VEGF. The truncated native VEGF has binding affinity for the KDR and Flt-1 receptors comparable to native VEGF.

An "anti-VEGF antibody" is an antibody that binds to VEGF with sufficient affinity and specificity. Preferably, the anti-VEGF antibody of the invention can be used as a therapeutic agent in targeting and interfering with diseases or conditions wherein the VEGF activity is involved. An anti-VEGF antibody will usually not bind to other VEGF homologues such as VEGF-B or VEGF-C, nor other growth factors such as PlGF, PDGF or bFGF. A preferred anti-VEGF antibody is a monoclonal antibody that binds to the same epitope as the monoclonal anti-VEGF antibody A4.6.1 produced by hybridoma ATCC HB 10709. More preferably the anti-VEGF antibody is a recombinant humanized anti-VEGF monoclonal antibody generated according to Presta et al. (1997) *Cancer Res.* 57:4593-4599, including but not limited to the antibody known as bevacizumab (BV; Avastin™).

The anti-VEGF antibody "Bevacizumab (BV)", also known as "rhuMAb VEGF" or "Avastin®, is a recombinant humanized anti-VEGF monoclonal antibody generated according to Presta et al. (1997) *Cancer Res.* 57:4593-4599. It comprises mutated human IgG1 framework regions and antigen-binding complementarity-determining regions from the murine anti-hVEGF monoclonal antibody A.4.6.1 that blocks binding of human VEGF to its receptors. Approximately 93% of the amino acid sequence of Bevacizumab, including most of the framework regions, is derived from human IgG1, and about 7% of the sequence is derived from the murine antibody A4.6.1. Bevacizumab has a molecular mass of about 149,000 daltons and is glycosylated.

A "VEGF antagonist" refers to a molecule capable of neutralizing, blocking, inhibiting, abrogating, reducing or interfering with VEGF activities including its binding to one or more VEGF receptors. VEGF antagonists include anti-VEGF antibodies and antigen-binding fragments thereof, receptor molecules and derivatives which bind specifically to VEGF thereby sequestering its binding to one or more receptors, anti-VEGF receptor antibodies and VEGF receptor antagonists such as small molecule inhibitors of the VEGFR tyrosine kinases.

"Treatment" refers to both therapeutic treatment and prophylactic or preventative measures. Those in need of treatment include those already with the disorder as well as those in which the disorder is to be prevented.

A "disorder" is any condition that would benefit from treatment with the antibody. For example, mammals who suffer from or need prophylaxis against abnormal angiogenesis (excessive, inappropriate or uncontrolled angiogenesis) or vascular permeability. This includes chronic and acute disorders or diseases including those pathological conditions which predispose the mammal to the disorder in question. Non-limiting examples of disorders to be treated herein include malignant and benign tumors; non-leukemias and lymphoid malignancies; neuronal, glial, astrocytal, hypothalamic and other glandular, macrophagal, epithelial, stromal and blastocoelic disorders; and inflammatory, angiogenic and immunologic disorders.

Abnormal angiogenesis occurs when new blood vessels either grow excessively, insufficiently or inappropriately (e.g., the location, timing or onset of the angiogenesis being undesired from a medical standpoint) in a diseased state or such that it causes a diseased state. Excessive, inappropriate or uncontrolled angiogenesis occurs when there is new blood vessel growth that contributes to the worsening of the diseased state or causes a diseased state, such as in cancer, especially vascularized solid tumors and metastatic tumors (including colon, lung cancer (especially small-cell lung cancer), or prostate cancer), diseases caused by ocular neovascularisation, especially diabetic blindness, retinopathies, primarily diabetic retinopathy or age-related macular degeneration (AMD), psoriasis, psoriatic arthritis, haemangioblastoma such as haemangioma; inflammatory renal diseases, such as glomerulonephritis, especially mesangioproliferative glomerulonephritis, haemolytic uremic syndrome, diabetic nephropathy or hypertensive nephrosclerosis; various imflammatory diseases, such as arthritis, especially rheumatoid arthritis, inflammatory bowel disease, psorsasis, sarcoidosis, arterial arteriosclerosis and diseases occurring after transplants, endometriosis or chronic asthma and more than 70 other conditions. The new blood vessels can feed the diseased tissues, destroy normal tissues, and in the case of cancer, the new vessels can allow tumor cells to escape into the circulation and lodge in other organs (tumor metastases). Insufficient angiogenesis occurs when there is inadequate blood vessels growth that contributes to the worsening of a diseased state, e.g., in diseases such as coronary artery disease, stroke, and delayed wound healing. Further, ulcers, strokes, and heart attacks can result from the absence of angiogenesis that normally required for natural healing. The present invention contemplates treating those patients that are at risk of developing the above-mentioned illnesses.

Other patients that are candidates for receiving the antibodies or polypeptides of this invention have, or are at risk for developing, abnormal proliferation of fibrovascular tissue, acne rosacea, acquired immune deficiency syndrome, artery occlusion, atopic keratitis, bacterial ulcers, Bechets disease, blood borne tumors, carotid obstructive disease, choroidal neovascularization, chronic inflammation, chronic retinal detachment, chronic uveitis, chronic vitritis, contact lens overwear, corneal graft rejection, corneal neovascularization, corneal graft neovascularization, Crohn's disease, Eales disease, epidemic keratoconjunctivitis, fungal ulcers, Herpes simplex infections, Herpes zoster infections, hyperviscosity syndromes, Kaposi's sarcoma, leukemia, lipid degeneration, Lyme's disease, marginal keratolysis, Mooren ulcer, Mycobacteria infections other than leprosy, myopia, ocular neovascular disease, optic pits, Osler-Weber syndrome (Osler-Weber-Rendu, osteoarthritis, Pagets disease, pars planitis, pemphigoid, phylectenulosis, polyarteritis, post-laser complications, protozoan infections, pseudoxanthoma elasticum, pterygium keratitis sicca, radial keratotomy, retinal neovascularization, retinopathy of prematurity, retrolental fibroplasias, sarcoid, scleritis, sickle cell anemia, Sogrens syndrome, solid tumors, Stargarts disease, Steven's Johnson disease, superior limbic keratitis, syphilis, systemic lupus, Terrien's marginal degeneration, toxoplasmosis, trauma, tumors of Ewing sarcoma, tumors of neuroblastoma, tumors of osteosarcoma, tumors of retinoblastoma, tumors of rhabdomyosarcoma, ulcerative colitis, vein occlusion, Vitamin A deficiency and Wegeners sarcoidosis, undesired angiogenesis associated with diabetes, parasitic diseases, abnormal wound healing, hypertrophy following surgery, injury or trauma, inhibition of hair growth, inhibition of ovulation and corpus luteum formation, inhibition of implantation and inhibition of embryo development in the uterus.

Anti-angiogenesis therapies are useful in the general treatment of graft rejection, lung inflammation, nephrotic syndrome, preeclampsia, pericardial effusion, such as that associated with pericarditis, and pleural effusion, diseases and disorders characterized by undesirable vascular permeability, e.g., edema associated with brain tumors, ascites associated with malignancies, Meigs' syndrome, lung inflammation, nephrotic syndrome, pericardial effusion, pleural effusion, permeability associated with cardiovascular diseases such as the condtion following myocardial infarctions and strokes and the like.

Other angiogenesis-dependent diseases according to this invention include angiofibroma (abnormal blood of vessels which are prone to bleeding), neovascular glaucoma (growth of blood vessels in the eye), arteriovenous malformations (abnormal communication between arteries and veins), nonunion fractures (fractures that will not heal), atherosclerotic plaques (hardening of the arteries), pyogenic granuloma (common skin lesion composed of blood vessels), scleroderma (a form of connective tissue disease), hemangioma (tumor composed of blood vessels), trachoma (leading cause of blindness in the third world), hemophilic joints, vascular adhesions and hypertrophic scars (abnormal scar formation).

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

The term "anti-neoplastic composition" refers to a composition useful in treating cancer comprising at least one active therapeutic agent, e.g., "anti-cancer agent." Examples of therapeutic agents (anti-cancer agents) include, but are limited to, e.g., chemotherapeutic agents, growth inhibitory agents, cytotoxic agents, agents used in radiation therapy, anti-angiogenesis agents, apoptotic agents, anti-tubulin agents, and other-agents to treat cancer, such as anti-HER-2 antibodies, anti-CD20 antibodies, an epidermal growth factor receptor (EGFR) antagonist (e.g., a tyrosine kinase inhibitor), HER1/EGFR inhibitor (e.g., erlotinib (Tarceva™), platelet derived growth factor inhibitors (e.g., Gleevec™ (Imatinib Mesylate)), a COX-2 inhibitor (e.g., celecoxib), interferons, cytokines, antagonists (e.g., neutralizing antibodies) that bind to one or more of the following targets ErbB2, ErbB3, ErbB4, PDGFR-beta, BlyS, APRIL, BCMA or VEGF receptor(s), TRAIL/Apo2, and other bioactive and organic chemical agents, etc. Combinations thereof are also included in the invention.

The term "cytotoxic agent" as used herein refers to a substance that inhibits or prevents the function of cells and/or causes destruction of cells. The term is intended to include radioactive isotopes (e.g., $I^{131}$, $I^{125}$, $Y^{90}$ and $Re^{186}$), chemotherapeutic agents, and toxins such as enzymatically active toxins of bacterial, fungal, plant or animal origin, or fragments thereof.

A "chemotherapeutic agent" is a chemical compound useful in the treatment of cancer. Examples of chemotherapeutic agents include is a chemical compound useful in the treatment of cancer. Examples of chemotherapeutic agents include alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew (1994) Chem. Intl. Ed. Engl. 33:183-186); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; NAVELBINE™ vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); inhibitors of PKC-alpha, Raf, H-Ras, EGFR (e.g., erlotinib (Tarceva™)) and VEGF-A that reduce cell proliferation and pharmaceutically acceptable salts, acids or derivatives of any of the above.

Also included in this definition are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON•toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Raf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; Vinorelbine and Esperamicins (see U.S. Pat. No. 4,675,187), and pharmaceutically acceptable salts, acids or derivatives of any of the above.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman (1986) "Prodrugs in Cancer Chemotherapy" *Biochemical Society Transactions,* 14, pp. 375-382, 615th Meeting Belfast and Stella et al. (1985). "Prodrugs: A Chemical Approach to Targeted Drug Delivery," *Directed Drug Delivery*, Borchardt et al, (ed.), pp. 247-267, Humana Press. The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

An "isolated" nucleic acid molecule is a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

Modes for Carrying Out the Invention
Production of Anti-NRP1 Antibodies

The invention herein provides novel anti-NRP1 antibodies. Exemplary methods for generating antibodies are described in more detail in the following sections.

The novel anti-NRP1 antibodies are selected using the NRP1 antigen derived from a mammalian species. Preferably the antigen is human NRP1 (hNRP1). However, NRPs from other species such as murine NRP1 (mNRP1) can also be used as the target antigen. The NRP antigens from various mammalian species may be isolated from natural sources. In other embodiments, the antigen is produced recombinantly or made using other synthetic methods known in the art.

The antibody selected will normally have a sufficiently strong binding affinity for the NRP1 antigen. For example, the antibody may bind hNRP1 with a $K_d$ value of no more than about 5 nM, preferably no more than about 2 nM, and more preferably no more than about 500 pM. Antibody affinities may be determined by a surface plasmon resonance based assay (such as the BIAcore assay as described in Examples); enzyme-linked immunoabsorbent assay (ELISA); and competition assays (e.g. RIA's), for example.

Also, the antibody may be subject to other biological activity assays, e.g., in order to evaluate its effectiveness as a therapeutic. Such assays are known in the art and depend on the target antigen and intended use for the antibody. Examples include the HUVEC inhibition assay (as described in the Examples below); tumor cell growth inhibition assays (as described in WO 89/06692, for example); antibody-dependent cellular cytotoxicity (ADCC) and complement-mediated cytotoxicity (CDC) assays (U.S. Pat. No. 5,500,362); and agonistic activity or hematopoiesis assays (see WO 95/27062).

To screen for antibodies which bind to a particular epitope on the antigen of interest, a routine cross-blocking assay such as that described in *Antibodies, A Laboratory Manual*, Cold Spring Harbor Laboratory, Ed Harlow and David Lane (1988), can be performed. Alternatively, epitope mapping, e.g. as described in Champe et al. (1995) *J. Biol. Chem.* 270:1388-1394, can be performed to determine whether the antibody binds an epitope of interest.

Generation of Novel Anti-NRP1 Antibodies From Synthetic Antibody Phage Libraries In a preferred embodiment, the invention provides a method for generating and selecting novel anti-NRP1 antibodies using a unique phage display approach. The approach involves generation of synthetic antibody phage libraries based on single framework template, design of sufficient diversities within variable domains, display of polypeptides having the diversified variable domains, selection of candidate antibodies with high affinity to target NRP1 antigen, and isolation of the selected antibodies.

Details of the phage display methods can be found, for example, in WO03/102157 published Dec. 11, 2003.

In one aspect, the antibody libraries used in the invention can be generated by mutating the solvent accessible and/or highly diverse positions in at least one CDR of an antibody variable domain. Some or all of the CDRs can be mutated using the methods provided herein. In some embodiments, it may be preferable to generate diverse antibody libraries by mutating positions in CDRH1, CDRH2 and CDRH3 to form a single library or by mutating positions in CDRL3 and CDRH3 to form a single library or by mutating positions in CDRL3 and CDRH1, CDRH2 and CDRH3 to form a single library.

A library of antibody variable domains can be generated, for example, having mutations in the solvent accessible and/or highly diverse positions of CDRH1, CDRH2 and CDRH3. Another library can be generated having mutations in CDRL1, CDRL2 and CDRL3. These libraries can also be used in conjunction with each other to generate binders of desired affinities. For example, after one or more rounds of selection of heavy chain libraries for binding to a target antigen, a light chain library can be replaced into the population of heavy chain binders for further rounds of selection to increase the affinity of the binders.

Preferably, a library is created by substitution of original amino acids with variant amino acids in the CDRH3 region of the variable region of the heavy chain sequence. The resulting library can contain a plurality of antibody sequences, wherein the sequence diversity is primarily in the CDRH3 region of the heavy chain sequence.

In one aspect, the library is created in the context of the humanized antibody 4D5 sequence, or the sequence of the framework amino acids of the humanized antibody 4D5 sequence. Preferably, the library is created by substitution of at least residues 95-100a of the heavy chain with amino acids encoded by the DVK codon set, wherein the DVK codon set is used to encode a set of variant amino acids for every one of these positions. An example of an oligonucleotide set that is useful for creating these substitutions comprises the sequence $(DVK)_7$. In some embodiments, a library is created by substitution of residues 95-100a with amino acids encoded by both DVK and NNK codon sets. An example of an oligonucleotide set that is useful for creating these substitutions comprises the sequence $(DVK)_6(NNK)$. In another embodiment, a library is created by substitution of at least residues 95-100a with amino acids encoded by both DVK and NNK codon sets. An example of an oligonucleotide set that is useful for creating these substitutions comprises the sequence $(DVK)_5(NNK)$. Another example of an oligonucleotide set that is useful for creating these substitutions comprises the sequence $(NNK)_6$. Other examples of suitable oligonucleotide sequences can be determined by one skilled in the art according to the criteria described herein.

In another embodiment, different CDRH3 designs are utilized to isolate high affinity binders and to isolate binders for a variety of epitopes. The range of lengths of CDRH3 generated in this library is 11 to 13 amino acids, although lengths different from this can also be generated. H3 diversity can be expanded by using NNK, DVK and NVK codon sets, as well as more limited diversity at N and/or C-terminal.

Diversity can also be generated in CDRH1 and CDRH2. The designs of CDR-H1 and H2 diversities follow the strategy of targeting to mimic natural antibodies repertoire as described with modification that focus the diversity more closely matched to the natural diversity than previous design.

For diversity in CDRH3, multiple libraries can be constructed separately with different lengths of H3 and then combined to select for binders to target antigens. The multiple libraries can be pooled and sorted using solid support selection and solution sorting methods as described previously and herein below. Multiple sorting strategies may be employed. For example, one variation involves sorting on target bound to a solid, followed by sorting for a tag that may be present on the fusion polypeptide (eg. anti-gD tag) and followed by another sort on target bound to solid. Alternatively, the libraries can be sorted first on target bound to a solid surface, the eluted binders are then sorted using solution phase binding with decreasing concentrations of target antigen. Utilizing combinations of different sorting methods provides for minimization of selection of only highly expressed sequences and provides for selection of a number of different high affinity clones.

High affinity binders for the target NRP1 antigen can be isolated from the libraries. Limiting diversity in the H1/H2 region decreases degeneracy about $10^4$ to $10^5$ fold and allowing more H3 diversity provides for more high affinity binders. Utilizing libraries with different types of diversity in CDRH3 (eg. utilizing DVK or NVT) provides for isolation of binders that may bind to different epitopes of a target antigen.

Of the binders isolated from the pooled libraries as described above, it has been discovered that affinity may be further improved by providing limited diversity in the light chain. Light chain diversity is generated in this embodiment as follows in CDRL1: amino acid position 28 is encoded by RDT; amino acid position 29 is encoded by RKT; amino acid position 30 is encoded by RVW; amino acid position 31 is encoded by ANW; amino acid position 32 is encoded by THT; optionally, amino acid position 33 is encoded by CTG; in CDRL2; amino acid position 50 is encoded by KBG; amino acid position 53 is encoded by AVC; and optionally, amino acid position 55 is encoded by GMA; in CDRL3: amino acid position 91 is encoded by TMT or SRT or both; amino acid position 92 is encoded by DMC; amino acid position 93 is encoded by RVT; amino acid position 94 is encoded by NHT; and amino acid position 96 is encoded by TWT or YKG or both.

In another embodiment, a library or libraries with diversity in CDRH1, CDRH2 and CDRH3 regions is generated. In this embodiment, diversity in CDRH3 is generated using a variety of lengths of H3 regions and using primarily codon sets XYZ and NNK or NNS. Libraries can be formed using individual oligonucleotides and pooled or oligonucleotides can be pooled to form a subset of libraries. The libraries of this embodiment can be sorted against target bound to solid. Clones isolated from multiple sorts can be screened for specificity and affinity using ELISA assays. For specificity, the clones can be screened against the desired target antigens as well as other nontarget antigens. Those binders to the target NRP1 antigen can then be screened for affinity in solution binding competition ELISA assay or spot competition assay. High affinity binders can be isolated from the library utilizing XYZ codon sets prepared as described above. These binders can be readily produced as antibodies or antigen binding fragments in high yield in cell culture.

In some embodiments, it may be desirable to generate libraries with a greater diversity in lengths of CDRH3 region. For example, it may be desirable to generate libraries with CDRH3 regions ranging from about 7 to 19 amino acids.

High affinity binders isolated from the libraries of these embodiments are readily produced in bacterial and eukaryotic cell culture in high yield. The vectors can be designed to readily remove sequences such as gD tags, viral coat protein component sequence, and/or to add in constant region sequences to provide for production of full length antibodies or antigen binding fragments in high yield.

A library with mutations in CDRH3 can be combined with a library containing variant versions of other CDRs, for example CDRL1, CDRL2, CDRL3, CDRH1 and/or CDRH2. Thus, for example, in one embodiment, a CDRH3 library is combined with a CDRL3 library created in the context of the humanized 4D5 antibody sequence with variant amino acids at positions 28, 29, 30, 31, and/or 32 using predetermined codon sets. In another embodiment, a library with mutations to the CDRH3 can be combined with a library comprising variant CDRH1 and/or CDRH2 heavy chain variable domains. In one embodiment, the CDRH1 library is created with the humanized antibody 4D5 sequence with variant amino acids at positions 28, 30, 31, 32 and 33. A CDRH2 library may be created with the sequence of humanized antibody 4D5 with variant amino acids at positions 50, 52, 53, 54, 56 and 58 using the predetermined codon sets.

Anti-NRP1 Antibody Mutants

The novel anti-NRP1 antibody generated from phage libraries can be further modified to generate antibody mutants with improved physical, chemical and or biological properties over the parent antibody. Where the assay used is a biological activity assay, the antibody mutant preferably has a biological activity in the assay of choice which is at least about 10 fold better, preferably at least about 20 fold better, more preferably at least about 50 fold better, and sometimes at least about 100 fold or 200 fold better, than the biological activity of the parent antibody in that assay. For example, an anti-NRP1 antibody mutant preferably has a binding affinity for NRP1 which is at least about 10 fold stronger, preferably at least about 20 fold stronger, more preferably at least about 50 fold stronger, and sometimes at least about 100 fold or 200 fold stronger, than the binding affinity of the parent anti-NRP1 antibody.

To generate the antibody mutant, one or more amino acid alterations (e.g. substitutions) are introduced in one or more of the hypervariable regions of the parent antibody. Alternatively, or in addition, one or more alterations (e.g. substitutions) of framework region residues may be introduced in the parent antibody where these result in an improvement in the binding affinity of the antibody mutant for the antigen from the second mammalian species. Examples of framework region residues to modify include those which non-covalently bind antigen directly (Amit et al. (1986) *Science* 233:747-753); interact with/effect the conformation of a CDR (Chothia et al. (1987) *J. Mol. Biol.* 196:901-917); and/or participate in the $V_L$-$V_H$ interface (EP 239 400B1). In certain embodiments, modification of one or more of such framework region residues results in an enhancement of the binding affinity of the antibody for the antigen from the second mammalian species. For example, from about one to about five framework residues may be altered in this embodiment of the invention. Sometimes, this may be sufficient to yield an antibody mutant suitable for use in preclinical trials, even where none of the hypervariable region residues have been altered. Normally, however, the antibody mutant will comprise additional hypervariable region alteration(s).

The hypervariable region residues which are altered may be changed randomly, especially where the starting binding affinity of the parent antibody is such that such randomly produced antibody mutants can be readily screened.

One useful procedure for generating such antibody mutants is called "alanine scanning mutagenesis" (Cunningham and Wells (1989) *Science* 244:1081-1085). Here, one or more of the hypervariable region residue(s) are replaced by alanine or polyalanine residue(s) to affect the interaction of the amino acids with the antigen from the second mammalian species. Those hypervariable region residue(s) demonstrating functional sensitivity to the substitutions then are refined by introducing further or other mutations at or for the sites of substitution. Thus, while the site for introducing an amino acid sequence variation is predetermined, the nature of the mutation per se need not be predetermined. The ala-mutants produced this way are screened for their biological activity as described herein.

Normally one would start with a conservative substitution such as those shown below under the heading of "preferred substitutions". If such substitutions result in a change in biological activity (e.g. binding affinity), then more substantial changes, denominated "exemplary substitutions" in the following table, or as further described below in reference to amino acid classes, are introduced and the products screened. Preferred Substitutions:

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Even more substantial modifications in the antibodies biological properties are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr, asn, gln;
(3) acidic: asp, glu;
(4) basic: his, lys, arg;
(5) residues that influence chain orientation: gly, pro; and
(6) aromatic: trp, tyr, phe.

Non-conservative substitutions will entail exchanging a member of one of these classes for another class.

In another embodiment, the sites selected for modification are affinity matured using phage display (see above).

Nucleic acid molecules encoding amino acid sequence mutants are prepared by a variety of methods known in the art. These methods include, but are not limited to, oligonucleotide-mediated (or site-directed) mutagenesis, PCR mutagenesis, and cassette mutagenesis of an earlier prepared mutant or a non-mutant version of the parent antibody. The preferred method for making mutants is site directed mutagenesis (see, e.g., Kunkel (1985) *Proc. Natl. Acad. Sci. USA* 82:488).

In certain embodiments, the antibody mutant will only have a single hypervariable region residue substituted. In other embodiments, two or more of the hypervariable region residues of the parent antibody will have been substituted, e.g. from about two to about ten hypervariable region substitutions.

Ordinarily, the antibody mutant with improved biological properties will have an amino acid sequence having at least 75% amino acid sequence identity or similarity with the amino acid sequence of either the heavy or light chain variable domain of the parent antibody, more preferably at least 80%, more preferably at least 85%, more preferably at least 90%, and most preferably at least 95%. Identity or similarity with respect to this sequence is defined herein as the percentage of amino acid residues in the candidate sequence that are identical (i.e same residue) or similar (i.e. amino acid residue from the same group based on common side-chain properties, see above) with the parent antibody residues, after aligning the sequences and introducing gaps, if necessary, to achieve the maximum percent sequence identity. None of N-terminal, C-terminal, or internal extensions, deletions, or insertions into the antibody sequence outside of the variable domain shall be construed as affecting sequence identity or similarity.

Following production of the antibody mutant, the biological activity of that molecule relative to the parent antibody is determined. As noted above, this may involve determining the binding affinity and/or other biological activities of the antibody. In a preferred embodiment of the invention, a panel of antibody mutants is prepared and screened for binding affinity for the antigen such as NRP1 or a fragment thereof. One or more of the antibody mutants selected from this initial screen are optionally subjected to one or more further biological activity assays to confirm that the antibody mutant(s) with enhanced binding affinity are indeed useful, e.g. for preclinical studies.

The antibody mutant(s) so selected may be subjected to further modifications, oftentimes depending on the intended use of the antibody. Such modifications may involve further alteration of the amino acid sequence, fusion to heterologous polypeptide(s) and/or covalent modifications such as those elaborated below. With respect to amino acid sequence alterations, exemplary modifications are elaborated above. For example, any cysteine residue not involved in maintaining the proper conformation of the antibody mutant also may be substituted, generally with serine, to improve the oxidative stability of the molecule and prevent aberrant cross linking. Conversely, cysteine bond(s) may be added to the antibody to improve its stability (particularly where the antibody is an antibody fragment such as an Fv fragment). Another type of amino acid mutant has an altered glycosylation pattern. This may be achieved by deleting one or more carbohydrate moieties found in the antibody, and/or adding one or more glycosylation sites that are not present in the antibody. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Vectors, Host Cells and Recombinant Methods

The anti-NRP1 antibody of the invention can be produced recombinantly, using techniques and materials readily obtainable.

For recombinant production of an anti-NRP1 antibody, the nucleic acid encoding it is isolated and inserted into a replicable vector for further cloning (amplification of the DNA) or for expression. DNA encoding the antibody is readily isolated or synthethized using conventional procedures (e.g., by using oligonucleotide probes that are capable of binding specifically to DNAs encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

(i) Signal Sequence Component

The antibody of this invention may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells that do not recognize and process the native antibody signal sequence, the signal sequence is substituted by a prokaryotic signal sequence selected, for example, from the group of the alkaline phosphatase, penicillinase, 1 pp, or heat-stable enterotoxin II leaders. For yeast secretion the native signal sequence may be substituted by, e.g., the yeast invertase leader, a factor leader (including *Saccharomyces* and *Kluyveromyces* α-factor leaders), or acid phosphatase leader, the *C. albicans* glucoamylase leader, or the signal described in WO 90/13646. In mammalian cell expression, mammalian signal sequences as well as viral secretory leaders, for example, the herpes simplex gD signal, are available.

The DNA for such precursor region is ligated in reading frame to DNA encoding the antibody.

(ii) Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

(iii) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the antibody nucleic acid, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity.

Alternatively, host cells (particularly wild-type hosts that contain endogenous DHFR) transformed or co-transformed with DNA sequences encoding antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al. (1979) *Nature* 282:39). The trp1 gene provides a selection marker for a mutant strain of yeast lacking the ability to grow in tryptophan, for example, ATCC No. 44076 or PEP4-1. Jones (1977) *Genetics* 85:12. The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 μm circular plasmid pKD1 can be used for transformation of *Kluyveromyces* yeasts. Alternatively, an expression system for large-scale production of recombinant calf chymosin was reported for *K. lactis*. Van den Berg (1990) *Bio/Technology* 8:135. Stable multi-copy expression vectors for secretion of mature recombinant human serum albumin by industrial strains of *Kluyveromyces* have also been disclosed. Fleer et al. (1991) *Bio/Technology* 9:968-975.

(iv) Promoter Component

Expression and cloning vectors usually contain a promoter that is recognized by the host organism and is operably linked to the antibody nucleic acid. Promoters suitable for use with prokaryotic hosts include the phoA promoter, β-lactamase and lactose promoter systems, alkaline phosphatase, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the antibody.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Antibody transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419, 446. A modification of this system is described in U.S. Pat. No. 4,601,978. See also Reyes et al. (1982) *Nature* 297:598-601 on expression of human β-interferon cDNA in mouse cells under the control of a thymidine kinase promoter from herpes simplex virus. Alternatively, the rous sarcoma virus long terminal repeat can be used as the promoter.

(v) Enhancer Element Component

Transcription of a DNA encoding the antibody of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv (1982) *Nature* 297:17-18 on enhancing elements for activation of eukaryotic promoters. The enhancer may be spliced into the vector at a position 5' or 3' to the antibody-encoding sequence, but is preferably located at a site 5' from the promoter.

(vi) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the antibody. One useful transcription termination component is the bovine growth hormone polyadenylation region. See WO94/11026 and the expression vector disclosed therein.

(vii) Selection and Transformation of Host Cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183, 070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al. (1977) *J. Gen Virol.* 36:59); baby hamster kidney cells (BHK, ATCC CCL 10); Chinese hamster ovary cells/-DHFR(CHO, Urlaub et al. (1980) *Proc. Natl. Acad. Sci. USA* 77:4216); mouse sertoli cells (TM4, Mather (1980) *Biol. Reprod.* 23:243-251); monkey kidney cells (CV1

ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al. (1982) *Annals N.Y. Acad. Sci.* 383:44-68); MRC 5 cells; FS4 cells; and a human hepatoma line (Hep G2).

Host cells are transformed with the above-described expression or cloning vectors for antibody production and cultured in conventional nutrient media modified as appropriate for inducing promoters, selecting transformants, or amplifying the genes encoding the desired sequences.

(viii) Culturing the Host Cells

The host cells used to produce the antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al. (1979) *Meth. Enz.* 58:44, Barnes et al. (1980) *Anal. Biochem.* 102:255, U.S. Pat. Nos. 4,767,704; 4,657,866; 4,927,762; 4,560,655; or 5,122,469; WO 90/03430; WO 87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(ix) Antibody Purification

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al. (1992) *Bio/Technology* 10:163-167 describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al. (1983) *J. Immunol. Meth.* 62:1-13). Protein G is recommended for all mouse isotypes and for human γ3 (Guss et al. (1986) *EMBO J.* 5:15671575). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Pharmaceutical Formulations

Therapeutic formulations of the antibody are prepared for storage by mixing the antibody having the desired degree of purity with optional physiologically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other. For example, it may be desirable to further provide an immunosuppressive agent. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Therapeutic Uses

It is contemplated that the antibody of the present invention may be used to treat a mammal. In one embodiment, the antibody is administered to a nonhuman mammal for the purposes of obtaining preclinical data, for example. Exemplary nonhuman mammals to be treated include nonhuman primates, dogs, cats, rodents and other mammals in which preclinical studies are performed. Such mammals may be established animal models for a disease to be treated with the antibody or may be used to study toxicity of the antibody of interest. In each of these embodiments, dose escalation studies may be performed in the mammal. Where the antibody is an anti-NRP1 antibody, it may be administered to a host rodent in a solid tumor model, for example.

In addition, or in the alternative, the antibody is used to treat a human, e.g. a patient suffering from a disease or disorder who could benefit from administration of the antibody.

The present invention encompasses antiangiogenic cancer therapy, a novel cancer treatment strategy aimed at inhibiting the development of tumor blood vessels required for providing nutrients to support tumor growth. Because angiogenesis is involved in both primary tumor growth and metastasis, the antiangiogenic treatment provided by the invention is capable of inhibiting the neoplastic growth of tumor at the primary site as well as preventing metastasis of tumors at the secondary sites, therefore allowing attack of the tumors by other therapeutics. Examples of cancer to be treated herein include, but are not limited to, carcinoma, lymphoma, blastoma, sarcoma, and leukemia. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome. More particularly, cancers that are amenable to treatment by the antibodies of the invention include breast cancer, colorectal cancer, rectal cancer, non-small cell lung cancer, non-Hodgkins lymphoma (NHL), renal cell cancer, prostate cancer, liver cancer, pancreatic cancer, soft-tissue sarcoma, kaposi's sarcoma, carcinoid carcinoma, head and neck cancer, melanoma, ovarian cancer, mesothelioma, and multiple myeloma. More preferably, the methods of the invention are used to treat colorectal cancer in a human patient.

It is contemplated that when used to treat various diseases such as tumors, the antibodies of the invention can be combined with other therapeutic agents suitable for the same or similar diseases. When used for treating cancer, antibodies of the present invention may be used in combination with conventional cancer therapies, such as surgery, radiotherapy, chemotherapy or combinations thereof.

In certain aspects, other therapeutic agents useful for combination cancer therapy with the antibody of the invention include other anti-angiogenic agents. Many anti-angiogenic agents have been identified and are known in the arts, including those listed by Carmeliet and Jain (2000).

In one aspect, the antibody of the invention is used in combination with a VEGF antagonist or a VEGF receptor antagonist such as anti-VEGF antibodies, VEGF variants, soluble VEGF receptor fragments, aptamers capable of blocking VEGF or VEGFR, neutralizing anti-VEGFR antibodies, inhibitors of VEGFR tyrosine kinases and any combinations thereof. Alternatively, or in addition, two or more anti-NRP1 antibodies may be co-administered to the patient. In a more preferred embodiment, the anti-NRP1$^A$ or anti-NRP$^B$ antibody of the invention is used in combination with an anti-VEGF antibody to generate additive or synergistic effects. Preferred anti-VEGF antibodies include those that bind to the same epitope as the anti-hVEGF antibody A4.6.1. More preferably the anti-VEGF antibody is bevacizumab or ranibizumab.

In some other aspects, other therapeutic agents useful for combination tumor therapy with the antibody of the invention include antagonist of other factors that are involved in tumor growth, such as EGFR, ErbB2 (also known as Her2) ErbB3, ErbB4, or TNF. Preferably, the anti-NRP1 antibody of the invention can be used in combination with small molecule receptor tyrosine kinase inhibitors (RTKIs) that target one or more tyrosine kinase receptors such as VEGF receptors, FGF receptors, EGF receptors and PDGF receptors. Many therapeutic small molecule RTKIs are known in the art, including, but are not limited to, vatalanib (PTK787), erlotinib (TARCEVA®), OSI-7904, ZD6474 (ZACTIMA®), ZD6126

(ANG453), ZD1839, sunitinib (SUTENT®), semaxanib (SU5416), AMG706, AG013736, Imatinib (GLEEVEC®), MLN-518, CEP-701, PKC-412, Lapatinib (GSK572016), bortezomib (VELCADE®), AZD2171, sorafenib (NEXAVAR®), XL880, and CHIR-265.

The anti-NRP1 antibody of the invention, either alone or in combination with a second therpateutic agent (such as an anti-VEGF antibody) can be further used in combination with one or more chemotherapeutic agents. A variety of chemotherapeutic agents may be used in the combined treatment methods of the invention. An exemplary and non-limiting list of chemotherapeutic agents contemplated is provided herein under "Definition".

When the anti-NRP1 antibody is co-administered with a second therapeutic agent, the second therapeutic agent may be administered first, followed by the anti-NRP1 antibody. However, simultaneous administration or administration of the anti-NRP1 antibody first is also contemplated. Suitable dosages for the second therapeutic agent are those presently used and may be lowered due to the combined action (synergy) of the agent and anti-NRP1 antibody.

For the prevention or treatment of disease, the appropriate dosage of antibody will depend on the type of disease to be treated, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

Depending on the type and severity of the disease, about 1 µg/kg to 50 mg/kg (e.g. 0.1-20 mg/kg) of antibody is an initial candidate dosage for administration to the patient, whether, for example, by one or more separate administrations, or by continuous infusion. A typical daily dosage might range from about 1 µg/kg to about 100 mg/kg or more, depending on the factors mentioned above. For repeated administrations over several days or longer, depending on the condition, the treatment is sustained until a desired suppression of disease symptoms occurs. However, other dosage regimens may be useful. In a preferred aspect, the antibody of the invention is administered every two to three weeks, at a dose ranged from about 5 mg/kg to about 15 mg/kg. More preferably, such dosing regimen is used in combination with a chemotherapy regimen as the first line therapy for treating metastatic colorectal cancer. In some aspects, the chemotherapy regimen involves the traditional high-dose intermittent administration. In some other aspects, the chemotherapeutic agents are administered using smaller and more frequent doses without scheduled breaks ("metronomic chemotherapy"). The progress of the therapy of the invention is easily monitored by conventional techniques and assays.

The antibody composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the antibody to be administered will be governed by such considerations, and is the minimum amount necessary to prevent, ameliorate, or treat a disease or disorder. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as used hereinbefore or about from 1 to 99% of the heretofore employed dosages. Generally, alleviation or treatment of a disease or disorder involves the lessening of one or more symptoms or medical problems associated with the disease or disorder. In the case of cancer, the therapeutically effective amount of the drug can accomplish one or a combination of the following: reduce the number of cancer cells; reduce the tumor size; inhibit (i.e., to decrease to some extent and/or stop) cancer cell infiltration into peripheral organs; inhibit tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. In some embodiments, a composition of this invention can be used to prevent the onset or reoccurrence of the disease or disorder in a subject or mammal.

Non-Therapeutic Uses

The antibodies of the invention may be used as affinity purification agents. In this process, the antibodies are immobilized on a solid phase such a Sephadex resin or filter paper, using methods well known in the art. The immobilized antibody is contacted with a sample containing the antigen to be purified, and thereafter the support is washed with a suitable solvent that will remove substantially all the material in the sample except the antigen to be purified, which is bound to the immobilized antibody. Finally, the support is washed with another suitable solvent, such as glycine buffer, pH 5.0, that will release the antigen from the antibody.

The antibodies of this invention may also be useful in diagnostic assays, e.g., for detecting expression of an antigen of interest in specific cells, tissues, or serum.

For diagnostic applications, the antibody typically will be labeled with a detectable moiety. Numerous labels are available which can be generally grouped into the following categories:

(a) Radioisotopes, such as $^{35}S$, $^{14}C$, $^{125}I$, $^{3}H$, and $^{131}I$. The antibody can be labeled with the radioisotope using the techniques described in *Current Protocols in Immunology*, Volumes 1 and 2, Coligen et al. (1991) Ed. Wiley-Interscience, New York, N.Y., Pubs. for example and radioactivity can be measured using scintillation counting.

(b) Fluorescent labels such as rare earth chelates (europium chelates) or fluorescein and its derivatives, rhodamine and its derivatives, dansyl, Lissamine, phycoerythrin and Texas Red are available. The fluorescent labels can be conjugated to the antibody using the techniques disclosed in *Current Protocols in Immunology*, supra, for example. Fluorescence can be quantified using a fluorimeter.

(c) Various enzyme-substrate labels are available and U.S. Pat. No. 4,275,149 provides a review of some of these. The enzyme generally catalyzes a chemical alteration of the chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al. (1981) Methods for the Preparation of Enzyme-Antibody Conjugates for use in Enzyme Immunoassay, in *Methods in Enzym.* (ed J. Langone & H. Van Vunakis), Academic press, New York 73:147-166.

Examples of enzyme-substrate combinations include, for example:

(i) Horseradish peroxidase (HRPO) with hydrogen peroxidase as a substrate, wherein the hydrogen peroxidase oxidizes a dye precursor (e.g., orthophenylene diamine (OPD) or 3,3', 5,5'-tetramethyl benzidine hydrochloride (TMB));

(ii) alkaline phosphatase (AP) with para-Nitrophenyl phosphate as chromogenic substrate; and (iii) β-D-galactosidase (β-D-Gal) with a chromogenic substrate (e.g., p-nitrophenyl-β-D-galactosidase) or fluorogenic substrate 4-methylumbelliferyl-β-D-galactosidase.

Numerous other enzyme-substrate combinations are available to those skilled in the art. For a general review of these, see U.S. Pat. Nos. 4,275,149 and 4,318,980.

Sometimes, the label is indirectly conjugated with the antibody. The skilled artisan will be aware of various techniques for achieving this. For example, the antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody is conjugated with a small hapten (e.g., digoxin) and one of the different types of labels mentioned above is conjugated with an anti-hapten antibody (e.g., anti-digoxin antibody). Thus, indirect conjugation of the label with the antibody can be achieved.

In another embodiment of the invention, the antibody need not be labeled, and the presence thereof can be detected using a labeled antibody which binds to the antibody.

The antibodies of the present invention may be employed in any known assay method, such as competitive binding assays, direct and indirect sandwich assays, and immunoprecipitation assays. Zola, *Monoclonal Antibodies: A Manual of Techniques*, pp. 147-158 (CRC Press, Inc. 1987).

Competitive binding assays rely on the ability of a labeled standard to compete with the test sample analyze for binding with a limited amount of antibody. The amount of antigen in the test sample is inversely proportional to the amount of standard that becomes bound to the antibodies. To facilitate determining the amount of standard that becomes bound, the antibodies generally are insolubilized before or after the competition, so that the standard and analyze that are bound to the antibodies may conveniently be separated from the standard and analyze which remain unbound.

Sandwich assays involve the use of two antibodies, each capable of binding to a different immunogenic portion, or epitope, of the protein to be detected. In a sandwich assay, the test sample analyze is bound by a first antibody which is immobilized on a solid support, and thereafter a second antibody binds to the analyze, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

For immunohistochemistry, the tumor sample may be fresh or frozen or may be embedded in paraffin and fixed with a preservative such as formalin, for example.

The antibodies may also be used for in vivo diagnostic assays. Generally, the antibody is labeled with a radionuclide (such as $^{111}$In, $^{99}$Tc, $^{14}$C, $^{131}$I, $^{125}$I, $^{3}$H, $^{32}$P or $^{35}$S) or a dye so that the tumor can be localized using immunoscintiography.

In one embodiment, a method of detecting NRP1 in a biological sample (e.g., tissue, blood, sera, spinal fluid) or a prepared biological sample can comprise the step of contacting an antibody of this invention with the sample and observing the anti-NRP1 antibody bound to the NRP1 in the sample or determining the amount of the anti-NRP1 antibody bound to NRP1 in the sample. In another embodiment, a method of detecting NRP1 in a subject comprises the step of administering an antibody of this invention to the subject and observing the anti-NRP1 antibody bound to the NRP1 in the subject or determining the amount of the anti-NRP1 antibody bound to NRP1 in the subject (e.g., human, mouse, rabbit, rat, etc).

Diagnostic Kits

As a matter of convenience, the antibody of the present invention can be provided in a kit, i.e., a packaged combination of reagents in predetermined amounts with instructions for performing the diagnostic assay. Where the antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

Articles of Manufacture

In another embodiment of the invention, an article of manufacture containing materials useful for the treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The active agent in the composition is the antibody. The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

The following examples are intended merely to illustrate the practice of the present invention and are not provided by way of limitation. The disclosures of all patent and scientific literatures cited herein are expressly incorporated in their entirety by reference.

EXAMPLES

Example 1

Generation of Anti-NRP1 Antibodies

A. Generation of Antibody Phage Libraries

A variety of methods are known in the art for generating antibody libraries displayed on phage or displayed using other technologies. One of the advantages of these libraries, as compared to conventional hybridoma technologies, is that they are well suited for generating cross-species functional antibodies, because they allow in vitro selection and screening without the introduction of immune tolerance. Smith (1985) *Science* 228:1315-1317; Bradbury and Marks (2004) *J Immunol Methods* 290:29-49.

In general, two types of combinatorial antibody libraries have been developed, distinguished by the source of repertoires. Most libraries to date are "natural" antibody libraries which use the natural repertoires as the source for its diversity, where the genes as message RNA of immune cells from naïve or immunized animals or human are amplified and cloned into vector for phage display or other display technology, such as ribosome or yeast display. The natural antibodies usually have multiple frameworks, which together with variable CDRs sequences and the recombination of light chain and heavy chain made up the diversity of the library. The size of the library determines the performance of the libraries since the repertoires are in general larger than the library size. The synthetic library, on the other hand, is a new branch of library where the diversity is designed and built into the library with synthetic DNA. Single or multiple frameworks have been used. For single framework library, the source of the diversity solely depends on the degeneracy of synthetic DNA designed to create the diverse CDR loops. Both the diversity design and the size of the libraries are critical for the library performance, which can be measured by the affinity of the antibodies found from the libraries. Knappik et al. (2000) *J Mol Biol* 296:57-86; Sheets et al. (1998) *Proc Natl Acad Sci USA* 95: 6157-6162; de Haard et al. (1999) *J Biol Chem* 274:18218-18230.

By introducing synthetic diversity at solvent-exposed positions within the variable heavy chain complementarity-determining regions (CDRs), Lee et al. developed a phage-displayed synthetic antibody library built on a single human framework ($VL_{kappa\ I}$, $VH_{subgroup\ III}$). Sidhu et al. (2004) *J Mol Biol* 338:299-310; Lee et al. (2004) *J Mol Biol* 340:1073-1093; Carter et al. (1992) *Proc Natl Acad Sci USA* 89:4285-4289. This "VH library" was displayed as a bivalent antigen-binding fragment (Fab'2) and used tailored codons to mimic the natural diversity observed in human immunoglobulin. Lee et al. (2004) *J Immunol Methods* 284:119-132. While the VH library has performed well as measured by the affinity and function of derived antibodies, further modifications in library design can be desirable in generating functional antibodies of certain antigen targets of interest. The recent availability of trinucleotides for oligonucleotide synthesis enabled the ability to increase amino acid diversity without increasing DNA diversity. A new "VH/VL library" was thus generated as described herein, wherein the highly variable positions in CDR-L3 were further diversified, since CDR-H3 and CDR-L3 form the inner sphere of the antigen-binding site. Mian et al. (1991) *J Mol Biol* 217:133-151.

Materials and Methods

The VH/VL naïve library template with consensus CDR-L1, -L2, -L3, -H1 and -H2 was generated using oligonucleotide-directed mutagenesis on phagemid pV0350-4 with stop codons on CDR-H3 and displaying bivalently on the surfaces of M13 bacteriophage particles. Lee et al. (2004) *J Mol Biol* 340:1073-1093. Phage-displayed libraries were constructed using Kunkel mutagenesis method as described (Kunkel et al. (1991) *Methods Enzymol* 204:125-139), with a mixture of mutagenic oligonucleotides designed to introduce mutations at the designed sites in CDR-L3, H1, H2 and H3 and repair CDR-H3 stop codons. The mutagenesis reactions (~10 µg DNA) were electroporated into *E. coli* SS320 cells (~$10^{11}$ cells), as described (Sidhu et al. (2004)).

Results

The VH/VL library described here utilized the trastuzumab (HERCEPTIN®) derived $VL_{kappa\ I}$ and $VH_{subgroup\ III}$ framework as used for the VH library, which has been shown to display well on bacteriophage, express well in *E. coli*, and which can rapidly be converted to a full length IgG that expresses well in mammalian cells. Lee et al. (2004) *J Mol Biol* 340:1073-1093; Carter et al. (1992) *Proc Natl Acad Sci USA* 89:4285-4289. The libraries were displayed on the phage surface as a bivalent Fab (Fab'$_2$) by being fused to the phage coat protein P3. This bivalent display was intended to increase the apparent binding affinities to immobilized antigens and help to improve the recovery of rare or low-affinity phage antibody clones.

To avoid potential biases inherited from the Herceptin®-derived CDR sequences maintained in the light chain of the VH library, consensus kappa I CDR sequences were introduced into the template for the VH/VL library. Consensus CDR residues are determined by selecting the most prevalent amino acids existing in natural human antibodies. The stop codons, previously employed in the heavy chain of the VH library to ensure mutagenesis in all 3 CDRs, were similarly replaced with consensus subgroup III sequences for CDR-H1 and CDR-H2. The consensus CDR sequences represent the most prevalent amino acid in each position. CDR-H3 plays a dominant role in antigen recognition, thus several stop codons were placed in H3 to ensure functional antibody clones from the libraries were different from each other. Xu et al. (2000) *Immunity* 13: 37-45. The presence of human consensus CDR sequences was expected to allow partially mutated variants (not all targeted CDRs are changed) to be displayed and to remain potentially functional in binding. In this way the VH/VL design has the advantage of increasing the ratio of functional phage antibody clones in the library. The CDR sequences used were SISSYL for CDR-L1 (positions 28-33), GASSRA for CDR-L2 (positions 50-55), YYSSPL for CDR-L3 (positions 91-96), FTFSSYAMS for CDR-H1 (positions 27-35), and RISPSGGSTY for CDR-H2 (positions 50-58), and WXXXRPXXMDY for CDR-H3 (positions 95-102, X is a stop codon) as shown in Table I. The prevalence of each position in human antibodies is also shown in Table I.

Diversity in the VH/VL library was introduced into a subset of CDR positions based on their high solvent exposure and/or especially high variability among natural antibody sequences. Positions chosen for mutagenesis and the diversity that was introduced are shown in Table II. For example, in CDR-H1, position 27, 28, 30, 31, 32, 33 and 34 were chosen to diversify. For the VH/VL library design, degenerate oligo codons or trinucletides were used to guide the diversity in each position so that the most prevalent amino acids would be represented. For example in CDR-H1 (position 30), serine represents about 50% of natural diversity, so a mixture of trinucletides (X1) that have ca. 52% serine and 2.5% of other amino acids except cysteine was used.

CDR-H3 and CDR-L3 form the center of the antigen-binding site and therefore show the highest frequency of antigen contacts in structurally known antibody-antigen complexes. Chothia et al. (1989) *Nature* 342:877-883. Five residues in CDR-L3 (Table II) with the highest variability were randomized. Overall CDR-H3 is the most diverse in terms of length, sequence, and structure and is a key component of the diversity in natural antibodies. Xu and Davis (2000) *Immunity*

13:37-45; Wu et al. (1993) *Proteins* 16:1-7. Thus 12 sub-libraries were constructed with different CDR-H3 lengths varying from 9 to 20 amino acids. Combined, these sub-libraries cover approximately 90% of CDR-H3 length variation in natural antibodies. Oligonucleotides encoding CDR-H3 were synthesized using trinucleotide codons. This enabled us to easily delete cysteine (rare in CDR-H3), and to boost levels of glycine, tyrosine and serine, the most abundant residues in CDR-H3. Mian et al. (1991) *J Mol Biol* 217:133-151. Codon X7, a trinucleotide mixture of about 15.6% each serine, tyrosine, and glycine, with 3.1% each of the remaining amino acids except cysteine, was used for each position in CDR-H3 (theoretical calculations for all trinucleotides mixture). Different combinations of trinucleotides were also used in selected positions of CDR-H1, H2, H3, and L3. As shown in Table II and Supplemental Table I, Codons X1 to X6 have a high percentage of serine, tyrosine, or glycine. X1 has 52.5% of serine, X2 has 52.5% tyrosine, X3 has 10% tyrosine, glycine or serine, X4 has 28.8% glycine, X5 has 19.2% tyrosine, glycine or serine, and X6 has 20% tyrosine or serine. The VH/VL antibody phage library was estimated to have approximately $10^{10}$ variants displayed.

TABLE I

Consensus sequence of CDR-L1, CDR-L2, CDR-L3, CDR-H1 and CDR-H2 in the template of VH/VL library. Consensus CDR residues are determined by selecting the most prevalent amino acids existing in natural human antibodies. The prevalence (%) of each residue in human antibodies at a given position is shown, which is calculated from the alignment of approximately 1600 human light chain sequences and 3500 human heavy chain sequences in the Kabat database (Kabat et al. (1977) *J Biol Chem* 252: 6609-6616).

| CDRs | Positions | Residues | Prevalence in natural human antibodies (%) |
|---|---|---|---|
| CDR-L1 | 28 | S | 33 |
|  | 29 | I | 40 |
|  | 30 | S | 55 |
|  | 31 | S | 44 |
|  | 32 | Y | 67 |
|  | 33 | L | 94 |

TABLE I-continued

Consensus sequence of CDR-L1, CDR-L2, CDR-L3, CDR-H1 and CDR-H2 in the template of VH/VL library. Consensus CDR residues are determined by selecting the most prevalent amino acids existing in natural human antibodies. The prevalence (%) of each residue in human antibodies at a given position is shown, which is calculated from the alignment of approximately 1600 human light chain sequences and 3500 human heavy chain sequences in the Kabat database (Kabat et al. (1977) *J Biol Chem* 252: 6609-6616).

| CDRs | Positions | Residues | Prevalence in natural human antibodies (%) |
|---|---|---|---|
| CDR-L2 | 50 | G | 25 |
|  | 51 | A | 79 |
|  | 52 | S | 95 |
|  | 53 | S | 36 |
|  | 54 | R | 60 |
|  | 55 | A | 45 |
| CDR-L3 | 91 | Y | 54 |
|  | 92 | Y | 23 |
|  | 93 | S | 46 |
|  | 94 | S | 24 |
|  | 95 | P | 80 |
|  | 96 | L | 22 |
| CDR-H1 | 27 | F | 45 |
|  | 28 | T | 54 |
|  | 29 | F | 73 |
|  | 30 | S | 68 |
|  | 31 | S | 50 |
|  | 32 | Y | 64 |
|  | 33 | A | 22 |
|  | 34 | M | 46 |
|  | 35 | S | 34 |
| CDR-H2 | 50 | R | 17 |
|  | 51 | I | 84 |
|  | 52 | S | 26 |
|  | 52a | P | 29 |
|  | 53 | S | 24 |
|  | 54 | G | 37 |
|  | 55 | G | 53 |
|  | 56 | S | 28 |
|  | 57 | T | 56 |
|  | 58 | Y | 32 |

TABLE II

Designed diversity of CDR-L3, CDR-H1, CDR-H2 and CDR-H3 for VH/VL library. CDR positions chosen for randomization in CDR-L3, CDR-H1, CDR-H2 and CDR-H3 are listed with consensus residues in the library template. Designed diversity is either a group of residues encoded by a tailored degenerate codon (italics) or 19 amino acids without cysteine encoded by mixtures of trinucleotides codon (bold text) so that the percentage of amino acid types encoded at each position was close to or higher than 50% of amino acid types found in the database. For particular positions, all 19 amino acids without cysteine are introduced using trinucleotides codon mixtures with different bias toward Tyr (Y), Gly (G) and Ser (S).

| CDRs | Positions | Codon | Design diversity | | | | Natural diversity coverage (%) |
|---|---|---|---|---|---|---|---|
|  |  |  | Residues encoded (%) | | | | |
|  |  |  | Y | G | S | others (-Cys) |  |
| CDR-L3 | Y91 | *TAC* | 100 | — | — | — | 77 |
|  |  | *MGC* | — | — | — | R/S(50) |  |
|  | Y92 | X5 | 19.2 | 19.2 | 19.2 | 2.5 | 100 |
|  | S93 | X1 | 2.5 | 2.5 | 52.5 | 2.5 | 100 |
|  | S94 | X6 | 20 | 3.3 | 20 | 3.3 | 100 |
|  | L96 | *NTC* | — | — | — | F/I/L/V(25) | 45 |
| CDR-H1 | F27 | *TWC* | 50 | — | — | F(50) | 65 |
|  | T28 | *ASC* | — | — | 50 | T(50) | 90 |
|  | S30 | *ASC* | — | — | 50 | T(50) | 86 |
|  | S31 | X1 | 2.5 | 2.5 | 52.5 | 2.5 | 100 |
|  | Y32 | X2 | 52.5 | 2.5 | 2.5 | 2.5 | 100 |
|  | A33 | X7 | 15.6 | 15.6 | 15.6 | 3.1 | 100 |
|  | M34 | *ATS* | — | — | — | M/I(50) | 67 |

TABLE II-continued

Designed diversity of CDR-L3, CDR-H1, CDR-H2 and CDR-H3 for VH/VL library. CDR positions chosen for randomization in CDR-L3, CDR-H1, CDR-H2 and CDR-H3 are listed with consensus residues in the library template. Designed diversity is either a group of residues encoded by a tailored degenerate codon (italics) or 19 amino acids without cysteine encoded by mixtures of trinucleotides codon (bold text) so that the percentage of amino acid types encoded at each position was close to or higher than 50% of amino acid types found in the database. For particular positions, all 19 amino acids without cysteine are introduced using trinucleotides codon mixtures with different bias toward Tyr (Y), Gly (G) and Ser (S).

| CDRs | Positions | Codon | Design diversity Residues encoded (%) | | | | Natural diversity coverage (%) |
|------|-----------|-------|------|------|------|------|------|
|      |           |       | Y    | G    | S    | others (-Cys) |       |
| CDR-H2 | R50 | X3 | 5 | 5 | 5 | 5 | 100 |
|      | S52 | X6 | 20 | 3.3 | 20 | 3.3 | 100 |
|      | P52a | *CCT* | — | — | — | P(100) | 100 |
|      |      | X7 | 15.6 | 15.6 | 15.6 | 3.1 | 100 |
|      | S53 | X7 | 15.6 | 15.6 | 15.6 | 3.1 | 100 |
|      | G54 | *RRC* | — | — | 25 | D/G/N(25) | 81 |
|      | S56 | *DMT* | 16.6 | — | 16.6 | A/D/N/T(16.6) | 81 |
|      | Y58 | *DAC* | 33.3 | — | — | D/N(33.3) | 70 |
| CDR-H3 | 95 | X4 | 3.8 | 28.8 | 3.8 | 3.8 | 100 |
|      | 96 | X4 | 3.8 | 28.8 | 3.8 | 3.8 | 100 |
|      | 97~100k | (X7)4~15 | 15.6 | 15.6 | 15.6 | 3.1 | >98 |
|      | 100l | X7 | 15.6 | 15.6 | 15.6 | 3.1 | 100 |
|      |      | *GBT* | — | 33.3 | — | A/V(33.3) | 89 |
|      | 100m | *TTC* | — | — | — | F(100) |  |
|      |      | *ATG* | — | — | — | M(100) |  |
|      | 101 | *GAT* | — | — | — | D(100) | 92 |
|      | 102 | *TAC* | 100 | — | — | — | 67 |
|      |      | *GTC* | — | — | — | V(100) |  |

B. Generation of Phage-Derived Monoclonal Anti-NRP1 Antibodies

Materials and Methods

Library Sorting and Screening to Identify Anti NRP1 Antibodies—

Human and murine NRP1 constructs (1-641aa) were cloned into mammalian expression vector, and expressed in CHO cells. Truncated form of NRP-1, a1a2 and b1b2 domains, were expressed in baculovirus. NUNC 96 well Maxisorp immunoplates were coated overnight at 4° with target antigen (10 ug/ml) and were blocked for 1 hr at room temperature with phage blocking buffer PBST (PBS and 1% BSA and 0.05% Tween 20). The antibody phage libraries were added to antigen plates and incubated overnight at RT. The following day antigen-coated plates were washed 10 times with PBT (PBS with 0.05% T-20), and bound phage were eluted with 50 mM HCl and 500 mM NaCl for 30 minutes and neutralized with equal volume of 1M Tris base pH7.5. Recovered phage was amplified in *E. coli* XL-1 Blue cells. During the subsequent selection rounds, incubation of antibody phage with the antigen-coated plates was reduced to 2-3 hours, and the stringency of plate washing was gradually increased.

Anti-NRP1 Antibodies Binding Affinities, Specificity and Flow Cytometry Analysis—

Phage antibody $IC_{50}$ values were determined using competitive phage-binding ELISA as described. Lee et al. (2004) *J Mol Biol* 340:1073-1093. Competition curves were fit with a four-parameter non-linear regression curve-fitting program (Kaleidagraph, Synergy Software) to determine the $IC_{50}$ values which were calculated as the concentration of antigen in solution binding stage that inhibited 50% of the phage-displayed antibody from binding to immobilized antigen.

Clones of interest were then reformatted into IgGs by cloning $V_L$ and $V_H$ region of individual clones into LPG3 and LPG4 vector respectively (Carter et al. (1992) *Proc Natl Acad Sci USA* 89:4285-4289), transiently expressed in mammalian cells, and purified with protein A columns. For binding affinity determinations of anti-NRP1 IgGs, Surface Plasmon Resonance (SPR) measurement with a BIAcore™-3000 instrument was used. Anti-NRP1 IgGs were coupled to activated CM5 biosensor chips to achieve approximately 500 response units (RU), followed by blocking un-reacted groups with 1M ethanolamine. For kinetic measurements, two-fold serial dilutions of Neuropilin (0.7 to 500 nM) were injected in PBST buffer at 25° C. with a flow rate of 30 μl/min. Association rates ($k_{on}$) and dissociation rates ($k_{off}$) were calculated using a simple one-to-one Langmuir binding model (BIAcore Evaluation Software version 3.2). The equilibrium dissociation constant (Kd) was calculated as the ratio $k_{off}/k_{on}$.

For binding specificity tests, 10 μg/ml of IgGs in PBST buffer was incubated with 2 μg/ml antigen-coated 96-well Maxisorp plates for at least 1 hr, and the plates were washed with PBT buffer. Bound antibodies were detected with anti-human antibody HRP conjugates, developed with TMB substrate for approximately 5 minutes, quenched with 1M $H_3PO_4$, and read spectrophotometrically at 450 nm.

For flow cytometry analysis, HUVEC cells were detached from the tissue culture flasks with cell dissociation buffer. Dissociated cells were washed in PBS and re-suspended in PBS containing 2% Fetal Bovine Serum (FACS buffer). Cells were incubated with 10 ug/ml anti-NRP1 antibodies or control antibody (anti-IgE) in FACS buffer on ice for 30 minutes. Cells were then washed twice in PBS, and stained in FACS buffer with PE-Fab'$_2$ goat anti-human IgG, Fc specific antibody on ice for 30 minutes. Following two PBS washes, the cells were re-suspended in 200 μl FACS buffer and analyzed by flow cytometry (FACS caliber, Benton Dickenson, Mountain View, Calif.) using Cell-Quest software.

Results

The 12 VH/VL sub-libraries were individually panned against immobilized CHO cell expressed hNRP1 (a1a2b1b2)-Fc protein for the first round of selection. Eluted phages from each sub-library were amplified and then combined for second round of selection. Since hNRP1-Fc was used as the antigen, the pooled phage was pre-absorbed with excess irrelevant Fc fusion protein after the first round of panning to minimize the recovery of anti-Fc phage antibodies. After the fourth round of panning, 95 randomly picked phage clones were evaluated for the ability to specifically bind to NRP1. Ninety percent of clones were positive for hNRP1 binding and 40% of positive clones bound both human and murine NRP1.

These phage clones were sequenced, and 10 unique clones were chosen for further characterization. All bound to both human and murine NRP1 with an $IC_{50}$ below 70 nM in the phage ELISA. Clone YW64.3 bound human and murine NRP1 with an $IC_{50}$ of 0.5 and 3.4 nM, respectively (Table III). Sequences from the 10 clones reflect the VH/VL library design with variable CDR-H3 lengths and varied changes distributed throughout CDR-H1, H2 and L3 yet some consensus CDR sequences from the library template are retained. Clones 64.3 and 64.29 have changes in all 4 CDRs and also have the best binding affinities to both human and murine NRP1 (Table III).

TABLE III

Partial CDR sequences and binding affinity (phage IC50) for anti-NRP1 antibodies. Only CDR amino acid sequences at randomized positions of 11 different phage clones initially identified from VH/VL library are shown. The affinities as $IC_{50}$ values to hNRP1 and mNRP1 were measured with competitive phage ELISA.

| Clone | Partial CDR-L3 (91-96) | SEQ ID NO: | Partial CDR-H1 (27-34) | SEQ ID NO: | Partial CDR-H2 (50-58) | SEQ ID NO: | Partial CDR-H3 (95-102) | SEQ ID NO: |
|---|---|---|---|---|---|---|---|---|
| YW64.3 | YMSVPI | 7 | FSFSSEPI | 18 | SITGKNGYY | 29 | WGKKVYG----MDV | 40 |
| YW 64.4 | YYSSPL | 8 | FTFSSYAM | 19 | SIAGSGGYY | 30 | WGGSNGSG---FDY | 41 |
| YW 64.14 | YYSSPL | 9 | YSFSSHMM | 20 | SIYPPGGYY | 31 | WGSRSPG----MDV | 42 |
| YW 64.23 | YYSSPL | 10 | FTFSSYAM | 21 | TIIPHGGYY | 32 | WAKRSYG----MDV | 43 |
| YW 64.28 | YYSSPL | 11 | FTFSSYAM | 22 | WISPLNGYY | 33 | WGRRYIG----MDV | 44 |
| YW 64.29 | RYSVPI | 12 | FTFSSYQL | 23 | SIF-SGGYY | 34 | YGNHV------MDV | 45 |
| YW 64.30 | YYSSPL | 13 | FTFSSYAM | 24 | SISRGDGYY | 35 | WAGGSA-----MDV | 46 |
| YW 64.47 | YYSSPL | 14 | FTFSQYSI | 25 | TIYPFGGYY | 36 | FGQSYYGGSYAMDV | 47 |
| YW 64.53 | YYSSPL | 15 | FTFTSRTM | 26 | SIS-SGGYY | 37 | WESYYG-----MDV | 48 |
| YW 64.55 | YYSSPL | 16 | FTFSSYAM | 27 | SIYSTGGYY | 38 | WGYPG------MDV | 49 |
| YW 107.4 | YYSSPL | 17 | FTFSSYAM | 28 | QISPAGGYN | 39 | ELPYYRMSKV-MDV | 50 |

| Clone | IC50 (nM) mNRP 1 | IC50 (nM) hNRP 1 |
|---|---|---|
| YW64.3 | 3.4 ± 0.9 | 0.48 ± 0.02 |
| YW 64.4 | 35 ± 9.6 | 24 ± 7.4 |
| YW 64.14 | 11 ± 3.4 | 5.2 ± 0.9 |
| YW 64.23 | 46 ± 21 | 47 ± 14 |
| YW 64.28 | 7.9 ± 1 | 1.2 ± 0.2 |
| YW 64.29 | 9.9 ± 4.2 | 2.7 ± 0.1 |
| YW 64.30 | 60 ± 11 | 50 ± 19 |
| YW 64.47 | 67 ± 25 | 21 ± 6 |
| YW 64.53 | 16 ± 2.9 | 4 ± 0.6 |
| YW 64.55 | 17 ± 5.8 | 3.9 ± 1 |
| YW 107.4 | 38 ± 20 | 6.1 ± 1 |

Domain-truncated variants of hNRP1 were used to identify the binding epitope for these clones and all were mapped to the a1a2 domain of hNRP1. To select phage antibodies that bound to the b1b2 domain of NRP1 and potentially block the binding of VEGF, we initiated a new panning process using baculovirus expressed hNRP1 (b1b2)-His as an immobilized antigen. Following 4 rounds of selection, only one unique clone, YW107.4 was identified that bound both human and murine NRP1. YW107.4 bound to human and murine NRP1 with an $IC_{50}$ of 6 and 38 nM in the Phage ELISA (Table III).

Characterization of Selected Anti-NRP1 IgG—

Figure 1B:
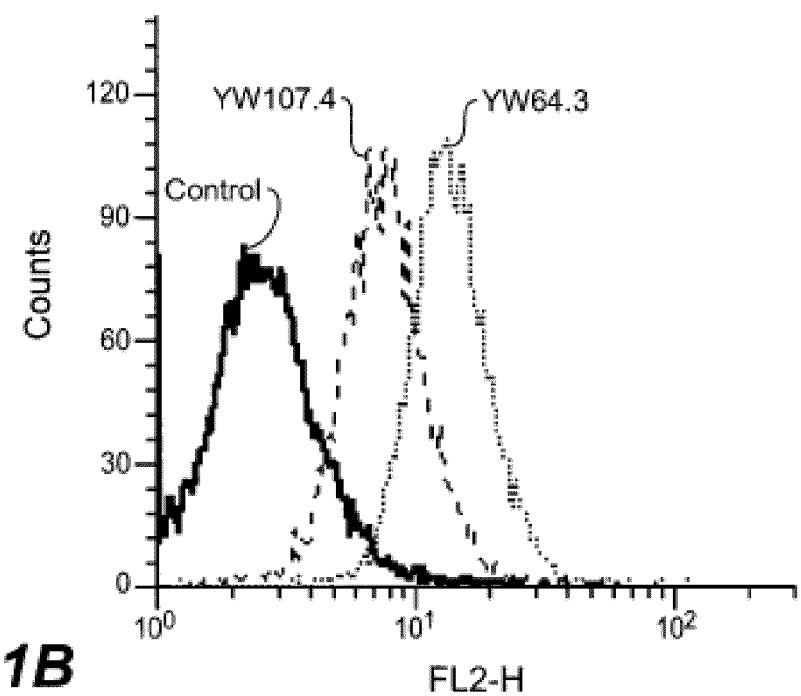

Selected anti-NRP1 clones from Table III were reformatted into full length human IgG1, expressed in CHO cells and purified for further characterization. The anti-NRP1 phage antibodies YW64.3 and YW107.4 bound specifically to human and murine NRP1 and did not bind to human or murine NRP-2, ErbB2-ECD or BSA. FIG. 1A. Each of the other eight-phage antibodies showed similar specificity. By surface plasmon resonance, immobilized YW64.3 and YW107.4 IgG did not interact with these antigens at concentrations up to 500 nM. However, both YW64.3 and YW107.4 bound human NRP1 with a Kd of 0.9 and 5 nM as well as murine NRP1 with a Kd of 7.8 and 11 nM, respectively. Although these antibodies were selected using plate-immobilized antigen, FACS analysis demonstrated all purified IgGs also bound to HUVEC cells which express hNRP1 endogenously (e.g. YW64.3 and YW107.4 shown in FIG. 1B).

C. Affinity Maturation of Anti-NRP1 Antibodies

YW107.4 bound to the b1b2 domain of both human and murine NRP1 with a phage $IC_{50}$ of 6 and 38 nM, respectively (Table III). To improve potency in vivo, this clone was affinity-matured using human NRP1-His.

Materials and Methods

To generate the library template for affinity maturation of clone YW107.4, the GCN4 leucine zipper of the parental phagemid was first removed using Kunkel mutagenesis to provide a monovalent display Fab format. A stop codon was incorporated in CDR-L3. A soft randomization strategy was used for affinity maturation, which introduced the mutation rate of approximately 50% at the selected positions by the mutagenic DNA synthesizing with 70-10-10-10 mixtures of bases favoring the wild type nucleotides. Gallop et al. (1994) *J Med Chem* 37:1233-1251. Three different libraries with combinations of CDR loops, L1/L2/L3, L3/H1/H2 and L3/H3 randomization, were generated through soft randomizing selected residues at positions 28-32 of CDR-L1, 50 and 53-55 of CDR-L2, 91, 92, 93, 94 and 96 of CDR-L3, 28-35 of CDR-H1, 50-58 of CDR-H2, and 95-100 of CDR-H3.

For selecting affinity-matured clones, phage libraries were subjected to plate sorting for the first round and followed by four rounds of solution phase sorting as described. Lee et al. (2004) *J Mol Biol* 340:1073-1093. At the first round of plate sorting, three libraries were added to hNRP1-coated plate separately for 1 hr at 37° C. After that, four rounds of solution phase sorting were performed to enhance the efficiency of affinity-based selection with increasing stringency as follow: round 2 (5 nM biotinylated hNRP1), round 3 (1 nM biotinylated hNRP1), round 4 (0.5 nM biotinylated hNRP1 and 250 nM non-biotinylated hNRP1 competitor at 37° C. for 1 hr) and round 5 (0.5 nM biotinylated hNRP1 and 500 nM non-biotinylated hNRP1 competitor at 37° C. for 3 hr). During the selection process, the reaction without biotinylated hNRP1 was included and served as background phage binding for calculating the enrichment of each round of panning.

After five rounds of panning, a high-throughput single-point competitive phage ELISA was used to rapidly screen for high-affinity clones as described. Sidhu et al. (2004) *J Mol Biol* 338:299-310. Clones with low ratio of the absorbance at 450 nm in the presence of 5 nM hNRP1 to that in the absence of hNRP1 were chosen for further characterization.

Results

Three different CDR combinations, L1/L2/L3, L3/H1/H2 and L3/H3, were targeted for randomization using a 'soft randomization' strategy that maintains a wild-type sequence bias such that selected positions are mutated only 50 percent of the time. Gallop et al. (1994) *J Med Chem* 37:1233-1251. For affinity maturation, the monovalent Fab was displayed on phage rather than bi-valent Fab to reduce potential avidity during selection. Stop codons were introduced at CDR-L3 in each sub-library. Off-rate selection strategies (see Methods) were employed to improve the affinity of YW107.4, since it already possessed a relatively high association rate constant ($2.2\times10^5$), but the dissociation rate constant ($1.1\times10^{-3}$) was relatively fast (Table V).

In the first round of selection, all 3 CDR soft-randomized libraries were panned against immobilized hNRP1 followed by subsequent rounds with a solution-phase sorting strategy to limit target concentration and enhance affinity-based selection. The concentration of biotinylated-hNRP1 was gradually reduced from 5 to 0.5 nM and a 500-fold excess of non-biotinylated hNRP1 was added to compete for fast off-rate binders. The mixture was also incubated at 37° C. for up to 2 hrs.

The L1/L2/L3 library showed significant enrichment following round 5. Ninety-six clones were randomly picked, sequenced and then affinities ranked. Twenty-three unique phage clones were selected and purified for further characterization. Most clones had improved affinity for hNRP1 as determined by phage competition ELISA. Surprisingly, the affinity for mNRP1 was also improved despite being omitted from the selection process, suggesting that the clones bound to a conserved epitope. Selected clones had 4 to 7 changes in the 3 light chain CDRs; positions 28 and 30 in CDR-L1 tended to be substituted with Tyrosine and Histidine, respectively, whereas positions 92, 93, and 96 in CDR-L3 were more diverse (Table IV).

Figure 2A:
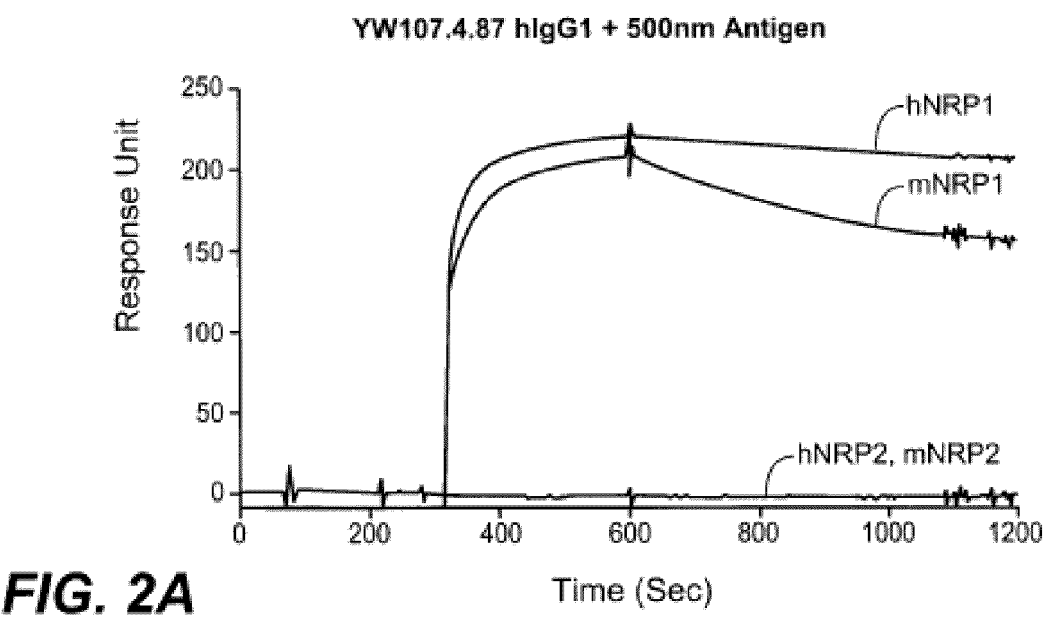
FIG. 2 illustrates binding properties of the anti-NRP1 antibody YW107.4 and its affinity matured variant YW107.4.87 (anti-NRP1$^B$). (2A) BIAcore kinetic analysis of the affinity-matured YW107.4.87 variant. (2B) FACS analysis of YW107.4 and YW107.4.87 IgGs showing improved binding to cell surface NRP1 protein (HUVECs) by the affinity matured variant YW107.4.87.
Figure 2B:
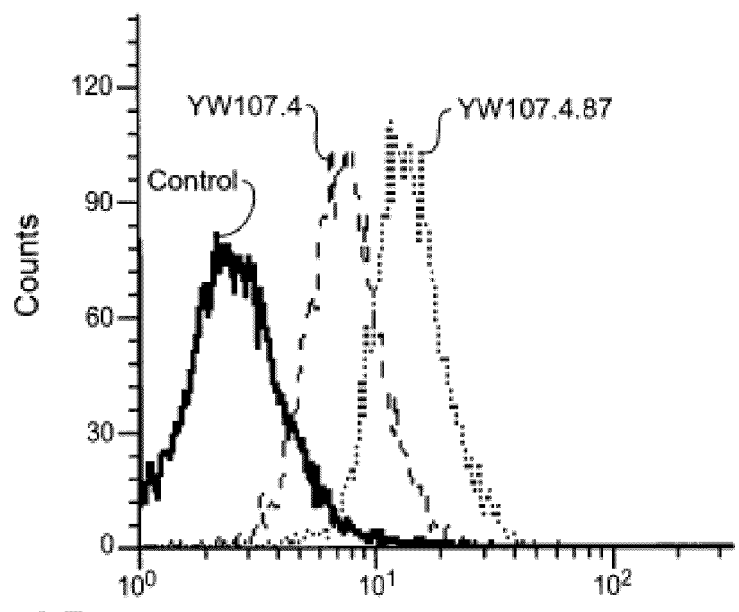

Clones with the highest affinity for both human and murine NRP1 (YW107.4.18, YW107.4.38, YW107.4.52, YW107.4.63, YW107.4.76a and YW107.4.87) were reformatted and expressed as full-length antibodies. All 6 IgGs had improved affinity for hNRP1 and maintained complete blocking of VEGF-A binding. Affinities for human and murine NRP1 ranged from 0.4 to 1.8 nM (Table V). The dissociation rate constant of YW107.4.87 was improved leading to an overall improvement in affinity of about 10-fold for both human and murine NRP1; no binding was observed to human or murine NRP2 (FIG. 2A). YW107.4.87 also showed improved binding to cell surface NRP1 (FIG. 2B).

TABLE IV

CDR sequences and binding affinity (phage IC50) for affinity improved YW107.4 clones. The deduced amino acids sequences of affinity-matured YW107.4 clones at randomized light chain CDR positions are shown. Fab-phage $IC_{50}$ values of individual clone against hNRP1 and mNRP1 from competition phage ELISA were used to compare affinity improvement with the YW107.4.

| Clone | Partial CDR-L1 (28-32) | SEQ ID NO: | Partial CDR-L2 (50-55) | SEQ ID NO: | Partial CDR-L3 (92-95) | SEQ ID NO: | IC50 (nM) mNRP1 | IC50 (nM) hNRP1 |
|---|---|---|---|---|---|---|---|---|
| YW107.4 | SISSY | 51 | GASSRA | 75 | YSSPL | 99 | 38 ± 20 | 6.1 ± 1 |
| YW107.4.33a | YISSY | 52 | GASRRA | 76 | IGSPI | 100 | 1.5 ± 0.4 | 0.31 ± 0.04 |
| YW107.4.53 | YISSY | 53 | GASRRE | 77 | LNSPL | 101 | 1.7 ± 0.1 | 0.30 ± 0.02 |
| YW107.4.66 | YISSY | 54 | GASSRA | 78 | IVSPL | 102 | 2.6 ± 0.6 | 0.45 ± 0.02 |
| YW107.4.76a | YISSY | 55 | GASRRA | 79 | LRSPH | 103 | 0.8 ± 0.4 | 0.23 ± 0.01 |
| YW107.4.78 | YISSY | 56 | GASSRE | 80 | LSSPI | 104 | 1.7 ± 0.2 | 0.30 ± 0.02 |
| YW107.4.85 | YISSY | 57 | GASSGE | 81 | IISPI | 105 | 4 ± 0.7 | 0.44 ± 0.06 |
| YW107.4.51 | RISSY | 58 | GASRRE | 82 | KLSPL | 106 | 12 ± 6 | 2 ± 0.5 |
| YW107.4.58 | YISSY | 59 | GASSRA | 83 | KSSPR | 107 | 3.5 ± 1.5 | 0.73 ± 0.28 |
| YW107.4.42 | WIHSY | 60 | GASSSA | 84 | YSSPL | 108 | 1.2 ± 2.2 | 0.81 ± 0.09 |
| YW107.4.59 | RIHSY | 61 | GASSRA | 85 | YISPL | 109 | 26 ± 14 | 1.8 ± 0.7 |
| YW107.4.33b | YIHSY | 62 | GASRRA | 86 | YGTPH | 110 | 7.8 ± 2 | 0.58 ± 0.07 |
| YW107.4.54 | PLHSY | 63 | GASSRA | 87 | YRSPL | 111 | 2.7 ± 1 | 0.84 ± 0.05 |
| YW107.4.63 | YLSSY | 64 | GASSSE | 88 | ISVPL | 112 | 0.8 ± 0.1 | 0.15 ± 0.01 |
| YW107.4.38 | YLSSY | 65 | GASSRA | 89 | LRSPI | 113 | 1.4 ± 0.3 | 0.28 ± 0.01 |
| YW107.4.18 | YFSSY | 66 | GASTHE | 90 | IRSPL | 114 | 1.1 ± 0.3 | 0.21 ± 0.02 |
| YW107.4.52 | YFSSY | 67 | GASTLA | 91 | IRSPL | 115 | 1.1 ± 0.3 | 0.22 ± 0.04 |
| YW107.4.87 | YFSSY | 68 | GASSRA | 92 | LGSPP | 116 | 1.5 ± 0.2 | 0.21 ± 0.04 |
| YW107.4.55 | LTHSY | 69 | GASSRA | 93 | YSSPL | 117 | 2 ± 2.4 | 0.93 ± 0.05 |
| YW107.4.20 | RTHSY | 70 | GASSRA | 94 | YGSPH | 118 | 33 | 0.45 ± 0.06 |
| YW107.4.12 | YTHSY | 71 | GASSRA | 95 | YSSPI | 119 | 3.4 ± 0.6 | 0.10 ± 0.02 |
| YW107.4.17 | YTHSY | 72 | GASSRA | 96 | YSSPV | 120 | 6 ± 1 | 0.24 ± 0.02 |
| YW107.4.41 | WTHSY | 73 | GASRLE | 97 | FISPH | 121 | 5.5 ± 2.3 | 0.43 ± 0.07 |
| YW107.4.76b | WVHSY | 74 | GASSRA | 98 | YGTPI | 122 | 3.9 ± 0.8 | 0.34 ± 0.01 |

TABLE V

Binding kinetic analysis of anti-NRP1 IgGs at 25° C. The binding affinities of anti-NRP1 IgGs are measured on BIAcore-3000 instrument using IgG-immobilized biosensor chip with dilutions of hNRP1 or mNRP1 flowing through at 25° C. (See Materials and Methods). Each measurement has an error in Kd approximately ±25%.

| Clone | murine NRP1 kon/$10^5$ ($M^{-1}s^{-1}$) | murine NRP1 koff/$10^{-4}$ ($s^{-1}$) | murine NRP1 Kd (nM) | human NRP1 kon/$10^5$ ($M^{-1}s^{-1}$) | human NRP1 koff/$10^{-4}$ ($s^{-1}$) | human NRP1 Kd (nM) |
|---|---|---|---|---|---|---|
| YW64.3 | 0.6 | 4.5 | 7.8 | 1.3 | 1.2 | 0.9 |
| YW107.4 | 1.4 | 15 | 11 | 2.2 | 11 | 5 |
| YW107.4.18 | 1.4 | 2.9 | 2.1 | 1.8 | 1.8 | 1 |
| YW107.4.38 | 0.84 | 2.7 | 3.2 | 0.94 | 1.7 | 1.8 |
| YW107.4.52 | 1.3 | 1.6 | 1.2 | 1.4 | 1.3 | 0.9 |
| YW107.4.63 | 1.6 | 1.3 | 0.8 | 1.8 | 1.5 | 0.8 |

TABLE V-continued

Binding kinetic analysis of anti-NRP1 IgGs at 25° C. The binding affinities of anti-NRP1 IgGs are measured on BIAcore-3000 instrument using IgG-immobilized biosensor chip with dilutions of hNRP1 or mNRP1 flowing through at 25° C. (See Materials and Methods). Each measurement has an error in Kd approximately ±25%.

| | murine NRP1 | | | human NRP1 | | |
|---|---|---|---|---|---|---|
| Clone | kon/$10^5$ ($M^{-1}s^{-1}$) | koff/ $10^{-4}$ ($s^{-1}$) | Kd (nM) | kon/$10^5$ ($M^{-1}s^{-1}$) | koff/ $10^{-4}$ ($s^{-1}$) | Kd (nM) |
| YW107.4.76a | 0.42 | 13 | 31 | 1.2 | 1.7 | 1.4 |
| YW107.4.87 | 1.6 | 2 | 1.3 | 1.9 | 0.77 | 0.4 |

Example 2

Biological Activities of Anti-NRP1 Antibodies

The antibody sequences of YW64.3 and YW107.4.87 are shown in FIG. 3. For the purpose of this application and in the following descriptions of anti-NRP1 antibody activities, "YW64.3" and "anti-NRP$^A$" are used interchangeably; and "YW107.4.87" and "anti-NRP$^B$" are used interchangeably.

Materials and Methods

Cell Cultures

HUVEC, HUAEC, and HMVECs were purchased from Cambrex and cultured in EGM-2 medium (Cambrex). Cells and tissue cultures are maintained at 37° C. in a 5% $CO_2$, 95% humidity incubator.

DRG and Hippocampal Collapse Assays

Collapse assays on axons from mouse E12.5 DRG were performed as described in He and Tessier-Lavigne (1997) Cell 90:739-751. Briefly, DRG explants were plated on laminin coated 8-chamber slides (Nunc) and cultured in N3-F12 medium with 50 ng/ml NGF overnight at 37° C. in a 5% $CO_2$, 95% humidity incubator. Human Semaphorin-3A (Met-1 to Val-771) was cloned into the eukaryotic expression vector pRK5 with a C-terminal hexahistidine fusion tag. The protein was transiently expressed in CHO cells and purified by NiNTA affinity chromatography. N-terminal sequencing was used to confirm the protein visible as a 90 kDa band on a Coomassie stained SDS-PAGE gel. Purified Sema3A was added at ~8 ng/ml in the presence or absence of inhibitors, and explants were incubated at 37° C. for 30 min to induce collapse. For visualization, growth cones were fixed in 4% PFA and 15% sucrose, stained with rhodamin-phalloidin (Molecular Probes) at 1:40 in PBS for 30 min, and then washed and mounted with Fluoromount G (Fisher). To perform the hippocampal collapse assay, E17 mouse brains were dissected in chilled PBS and horizontally sectioned into 250 µm thick slices using a tissue chopper (McIlwain). The dentate gyrus was further subdissected from selected sections of hippocampus using fine tungsten needles. Explants were plated on laminin coated 8-chamber slides (Nunc) and cultured in Neurobasal medium supplemented with B27 (Gibco Life Technologies) overnight at 37° C. To induce collapse, explants were incubated with control or anti-NRP1 antibodies (10 µg/ml) in the presence of mock transfected or Sema3F transfected COS cell conditioned media for 30 minutes at 37° C.

Cell Migration Assay

Cell migration assays were performed using a modified Boyden chamber assay with the 8 µm pore size Falcon 24-multiwell insert system (BD Biosciences). The plates were pre-coated with 8 µg/ml Laminin (Invitrogen) for 16 hrs at 37° C. in both the upper and lower chambers. HUVECs (80-90% confluent) were harvested with trypsin, counted, centrifuged and resuspended in EBM-2 with 0.1% BSA at a concentration of $5 \times 10^5$ cells/ml. 100 µl cells were added into the upper chamber of the transwell system. Inhibitors were added to the upper chamber with the cells immediately before addition of the stimuli to the lower chamber (10 ng/ml of VEGF in most cases), which contained 500 µl EBM-2 with 0.1% BSA. The plates were then placed at 37° C. overnight. To cease the assay, cells on the upper face of the membrane were removed using a sponge swab and cells on the lower face were fixed with methanol and stained with Cytox green (Molecular Probes). The number of migrated cells on the lower face of the membrane was counted using AxiPhot fluorescent microscope and the results were analyzed with the ImageJ program (NIH, http://rsb.info.nih.gov/ij/).

Bead Outgrowth Assay

Dextran-coated Cytodex 3 microcarrier beads (Amersham Pharmacia) were incubated with subconfluent HUVECs at a concentration of 400 cells per bead in 1 ml of EGM-2 medium, for 4 hrs at 37° C. in a 5% CO2 incubator with gentle shake every 20 min. Beads were then transferred to a 25-$cm^2$ tissue culture flask (BD Biosciences) and incubated in 5 ml of EGM-2 for 12-16 hrs at 37° C. HUVEC-coated beads were then washed three times with 1 ml EGM-2 and resuspended in 2.5 m/ml of fibrinogen (Sigma) in PBS at a density of 200 beads/ml. 0.5 ml of fibrinogen/bead solution was transferred into one well of a 24-well tissue culture plate containing 0.625 units thrombin (Sigma) to induce clotting. The fibrinogen/bead solution was incubated for 5 min at room temperature, then for 20 min at 37° C. in a 5% CO2 incubator. After the clotting was complete, 1 ml of EGM-2 was added to each well and the clot was equilibrated for 30 min at 37° C. The medium was removed, and 1 ml of skin fibroblast cells (Detroit 551) at a concentration of 2000/ml in EGM-2 medium were plated on the top of the clot. Different antibodies were then added to each well and the assay was monitored for 8 days with change in medium every 2-3 days. 10× resolution images of the beads were captured by an inverted microscope, and concentric circles spaced at 100, 200, and 300 µm were digitally drawn around the bead in each image. The number of vessels crossing each line was counted and the average was taken at each distance and condition.

FACS Analysis

Confluent HUVECs were incubated with control or anti-NRP1 antibodies at 10 µg/ml for 5 min, 2 hrs or 20 hrs at 37° C. in a 5% CO2 incubator. Cells were harvested with enzyme free cell dissociation buffer (Gibco), neutralized with equal volume of FACS buffer (1×PBS, 2% FBS, 2 mM EDTA, 0.1% sodium azide) and transferred into Pro-bind U-bottom 96-well assay plates (Falcon) at 500,000 cells per well. Cell pellets were collected by centrifuged at 2 k rpm, and resuspended in 25 µl staining buffer (FACS buffer with 5% normal mouse serum, 2% normal rat serum and 10% 10 µg/ml human IgG) containing appropriate biotinylated antibody at 1:100, followed by a 2 hr incubation at 4° C. Antibodies were biotinylated using the FluoReporter mini-biotin-xx protein labeling kit (Molecular Probes). Cells were then washed twice with FACS buffer, and incubated in 25 µl FACS buffer containing 1:1000 streptavidin-PE (BD Biosciences) for 20 min at 4° C. Finally, cells were washed and resuspended in FACS buffer, and analyzed with the FacsCalibur system (BD Biosciences).

Cell Adhesion Assay

Subconfluent HUVECs were pre-incubated in 100 µl Medium 199 with control or anti-NRP1 antibodies for 30 min at 37° C., then plated on NUNC maxisorp flat bottom 96-well plates (eBioscience) coated with 1 µg/ml Fibronectin (Roche)

at 10,000 cells per well. Plates were centrifuged for 1 min at 140 g to synchronize contract of cells with substrate, and incubated at 37° C. for 30 min. Plates were then washed 3 times with PBS, frozen at −80° C. for two hours. Cell density was determined with the CyQuant kit (Molecular Probes).

Mouse Neonatal Retinal Vascular Assay

Neonatal CD1 mice (same litters) were administered via i.p. with different antibodies at a concentration of 10 mg/kg. The injections were performed on postnatal day 1 and 3 for postnatal day 5 (P5) studies, and on day 1, 3 and 5 for P8 studies. Eyes were collected and fixed with 4% PFA in PBS for 16 hrs at 4° C., followed by PBS washes. The dissected retinas were block with 10% mouse serum in PBSt (PBS, 1% Triton X-100) for 3 hrs, then incubated overnight at 4° C. with biotinylated isolectin B4 (Bandeiraea simplicifolia; Sigma) 25 µg/ml in PBLEC (1% Triton X-100, 0.1 mM $CaCl_2$, 0.1 mM $MgCl_2$, 0.1 mM $MnCl_2$, in PBS pH 6.8). Retinas were then washed 4 times in PBSt, and incubated with Alexa 488 streptavidin (1:200; Molecular Probes) overnight at 4° C. After staining was completed, retinas were washed 4 times in PBSt, post fixed with 4% PFA in PBS, followed by another 4 washes in PBS. Images of flat mounted retinas were captured by confocal fluorescence microscopy.

Mouse Skin Vessel Permeability Assay 5-7 week C57BL6J female mice were injected with 150 µl 0.5% Evan's blue solution i.v. The areas of the back and flanks of the animals were shaved to remove hair below the neck and above the hip, and the shaved area was divided into 4 injection zones. One hour after the Evan's blue injection, 20 µl of PBS containing BSA (7.5 µg/ml) or hVEGF (7.5 µg/ml) with or without antibody (0.5 mg/ml) were injected i.d. randomly on any one of four zones, one injection for each zone. One hour after the i.d. injection, the animals were sacrificed and the skin containing the 4 zones was dissected out. A digital image of the skin was taken. A 8 mm skin biopsy punch was used to cut out skin samples of same area on the injection sites, and skin samples were incubated in formamide solution at 55° C. for 48 hrs to extract the Evan's blue dye from the tissues. The absorbance of the solution was then measured with a spectrometer at 605 nm Cell Proliferation Assay Cell proliferation was analyzed with the Cell Proliferation ELISA kit (Roche). Briefly, 90% confluent HUVECs were harvested and resuspended in assay media (DMEM:F12 50:50, 1.5% FBS), and plated at 3,000 cells per well into black 96-well tissue culture plate (ViewPlate-96, Perkin Elmer) pre-coated with 1% gelatin. Cells were incubated at 37° C. for 16 hrs, changed into fresh assay media and incubated for another 8 hrs. VEGF (20 ng/ml) and different antibodies were added to the culture and the cells were incubated for 20 hrs. BrdU labeling solution was added to a final concentration of 10 mM and the cells were incubated for another 24 hrs at 37° C. BrdU incorporation was determined by chemiluminescence immunoassay.

VEGFR2 Phosphorylation Assay

Total VEGFR2 and phospho-VEGFR2 were determined with DuoSet IC ELISA kits (R&D). Briefly, subconfluent HUVECs were rinsed with PBS and lysed in the provided lysis buffer. Cell lysates were centrifuged at 14 kg for 5 min at 4° C., and supernatants were transferred to clean tubes. ELISA assays were then carried out as directed.

Immunoblotting

Confluent HUVECs were starved for 16 hrs in EBM-2 with 0.2% FBS and 0.1% BSA, and then changed into EMB-2 with 0.1% BSA, followed by a 90 min incubation at 37° C. Control and anti-NRP1 antibodies were added at 50 µg/ml, and cells were incubated for 30 min at 37° C. Cells were stimulated with VEGF (20 ng/ml) for 10 min at 37° C., washed twice with ice-cold PBS and lysed in lysis buffer containing 20 mM Tris 7.5, 150 mM NaCl, 1% Triton X-100, phosphatase inhibitor cocktail I and II (Sigma) and complete protease inhibitor tablet (Roche). Aliquots of lysate were subjected to electrophoresis in 4-20% Novex Tris-Glycine SDS gels (Invitrogen), followed by electrotransfer to Invitrolon PVDF membrane (Invitrogen). The primary antibodies used in this study were anti-Erk, anti-phospho-Erk, anti-Akt, anti-phospho-Akt, anti-p38, anti-phospho-p38, anti-Src and anti-phospho-Src (Tyr416), all purchased from Cell Signaling Technology.

Results

Figure 4:
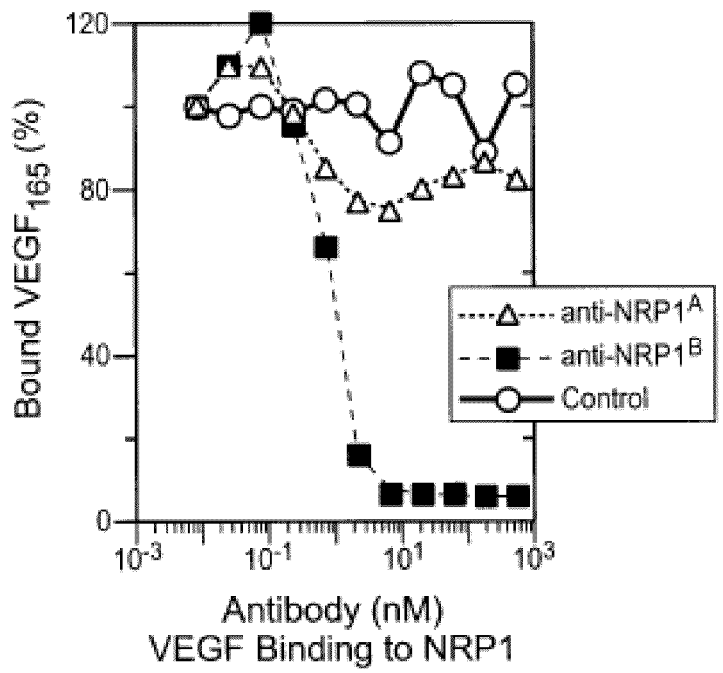
FIG. 4 depicts the blocking of VEGF$_{165}$ binding to NRP1 by anti-NRP1 antibodies.

A. Selective actions of anti-$NRP1^A$ and anti-$NRP1^B$ on Sema3A Function and VEGF Binding, Respectively Anti-NRP1 antibodies were tested for their ability to block binding of $VEGF_{165}$ to NRP1. Anti-$NRP1^B$ strongly blocked VEGF binding to NRP1, whereas anti-$NRP1^A$ did not (FIG. 4). These results suggests that the CUB domains (a1-a2) of NRP1 are not necessary for VEGF binding. Gu et al. (2002) *J Biol Chem* 277:18069-18076.

Figure 5A:
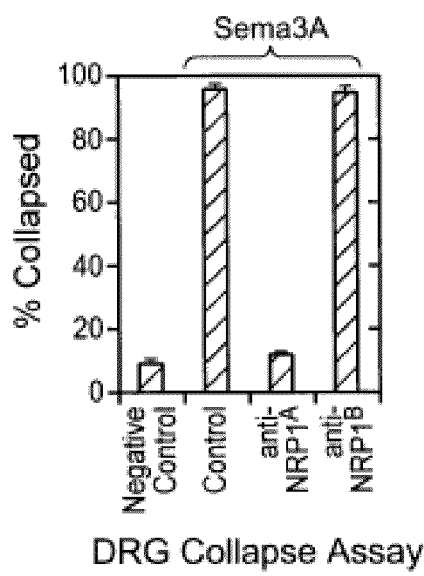
FIG. 5 depicts the quantification of Sema3A-induced DRG collapse (5A) and Sema3F-induced hippocampal collapse assays (5B). Anti-NRP1$^A$ is shown to specifically block Sema3A-induced growth cone collapse of DRG neurons, but not Sema3F-induced growth cone collapse of hippocampal neurons.

Next, anti-NRP1 antibodies were tested for their effects on Sema3A function. It has been previously suggested that Sema3A and $VEGF_{165}$ may share overlapping binding domains in the N-terminal region of the b1 domain, and thus may compete for binding to NRP1. Gu et al. (2002) *J Biol Chem* 277:18069-18076; Miao et al. (1999) *J Cell Biol* 146:233-242. Therefore, it seemed possible that a single anti-NRP1 mAb would block both Sema3A and VEGF binding. Anti-NRP1 mAbs of this invention were tested for their abilities to block Sema3A-induced axon growth cone collapse. Dorsal root ganglia (DRG) were dissected from mouse E12.5 embryos and cultured to establish sensory neuron growth cones that were responsive to Sema3A/NRP1-dependent collapse. He and Tessier-Lavigne (1997) *Cell* 90:739-751. Adding Sema3A to these cultures caused growth cones to retract their actin rich structures. However, if anti-$NRP1^A$ was added to the wells at the same time as Sema3A, collapse was completely blocked. In contrast, anti-$NRP1^B$ had no effect on Sema3A-induced collapse (FIG. 5A).

Figure 5B:
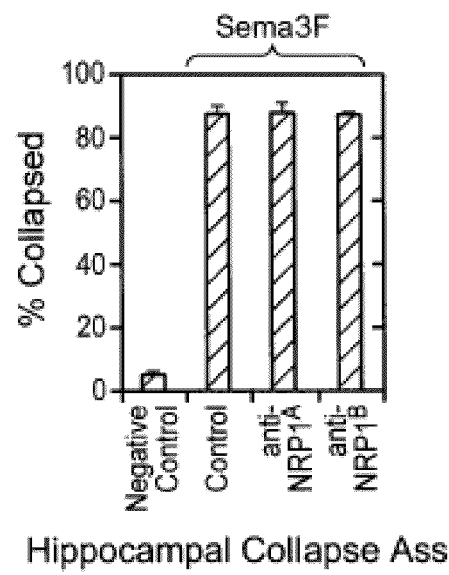

These two antibodies thus have functionally distinct actions: anti-$NRP1^A$ blocks Sema3A function but does not interfere with VEGF binding to NRP1; whereas anti-$NRP1^B$ blocks VEGF binding to NRP1 without effect on Sema3A function. Further studies showed that neither antibody blocks Sema3F/NRP2-dependent collapse of E17 hippocampal growth cones (FIG. 5B), consistent with the observation that neither antibody binds NRP2. The antibodies thus provide selective tools to dissect the role of NRP1 in vascular biology, and means for selectively blocking NRP1 activities.

Figure 6A:
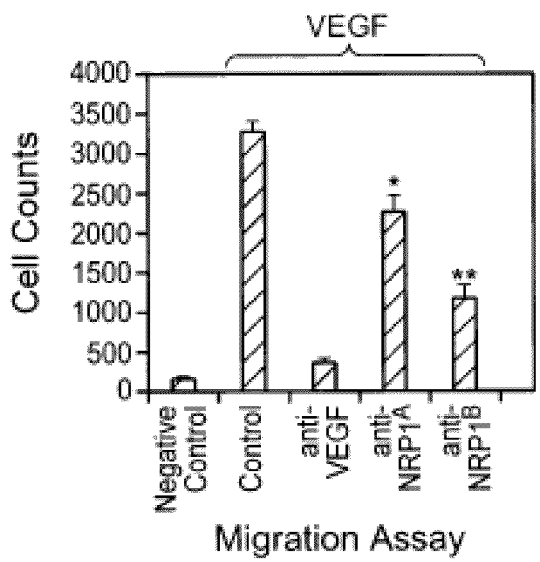
FIG. 6 illustrates that anti-NRP1 antibodies are capable of inhibiting VEGF-induced HUVEC migration and sprouting in vitro. (6A) Quantification of migration assay, (n=6 for each condition). *p=0.00003; **p=9.9×10$^{-11}$; Student's t test. (6B) Quantification of bead sprouting assay, n=12-14 beads per condition.

B. Both Anti-$NRP1^A$ and Anti-$NRP1^B$ Reduce $VEGF_{165}$-Dependent Endothelial Cell Migration and Bead Outgrowth The anti-NRP1 mAbs of the invention were tested in VEGF-driven endothelial cell (EC) migration. Using a transwell system, human umbilical vein endothelial cells (HUVECs) were introduced into the top chamber, while VEGF was added to the bottom chamber to promote EC migration. ECs that had migrated to the bottom chamber were then fixed, stained, and quantified (FIG. 6A). Anti-VEGF antibodies were used as a positive control to block VEGF-driven EC migration in this and subsequent experiments (a cross-species reactive anti-VEGF antibody, B20.4.1, was used in all experiments unless stated otherwise; Liang et al. (2006) *J Biol Chem* 281:951-961.

Anti-NRP1 mAbs were added to cells in the top chamber just prior to the addition of VEGF. Interestingly, both anti-$NRP1^A$ and anti-$NRP1^B$ significantly reduced endothelial cell migration, with anti-NRP1$^B$ providing a stronger block of migration (FIG. 6A). Similar results were obtained using two other types of EC lines, HUAECs and HAECs.

Figure 6B:
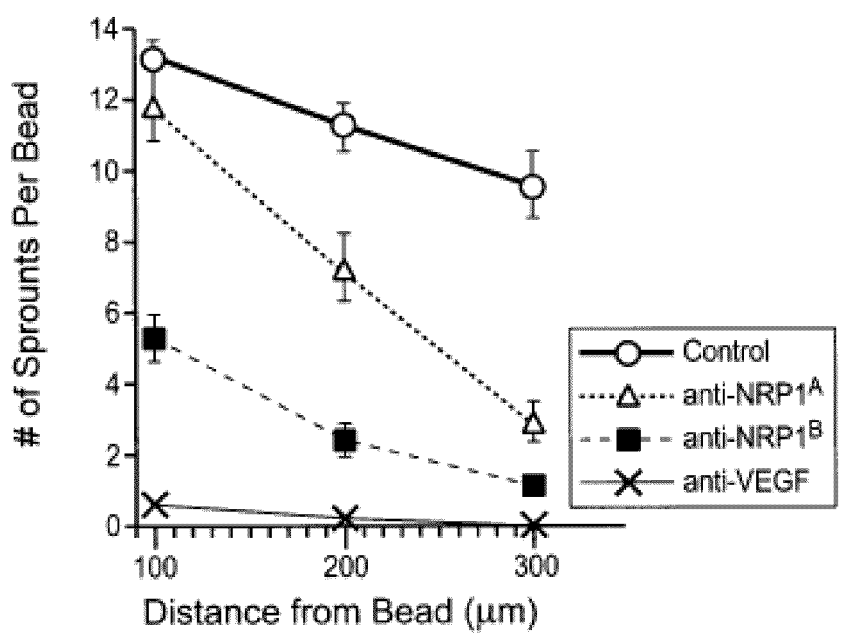

To further dissect the role of NRP1 and anti-NRP1 mAbs in more complex EC functions, an in vitro system of angiogenic sprouting was employed. Nakatsu et al. (2003) *Microvasc Res* 66:102-112. In this assay, ECs coated on beads sprout over a seven days period, resulting in multiple well-defined vessel structures protruding from each bead. Adding either anti-NRP1 mAbs to these cultures resulted in a reduction in vessel length, and in the case of anti-NRP1$^B$ a decrease in the number of sprouts was also observed. This observation was confirmed by quantification (FIG. 6B). Anti-VEGF was used as a positive control and completely blocked sprouting in this assay. The results confirmed strong effects for each anti-NRP1 mAb in reducing EC migration and outgrowth of vessels in this in vitro assay.

C. NRP1 is Necessary for Vascular Remodeling in the Mouse Retina

Figure 7A:
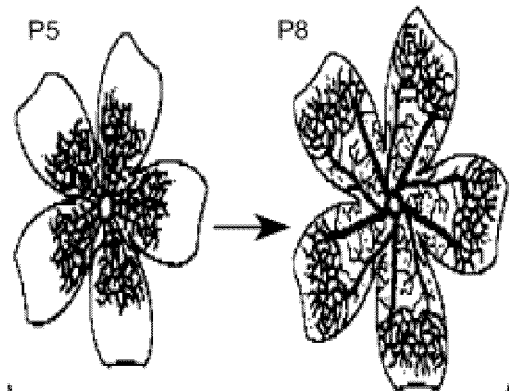
FIG. 7 illustrates anti-NRP1 antobody's in vivo inhibitory effects on vascular remodeling in developing mouse retina. (7A) Illustration of vascular development from postnatal day 5 (P5) to P8. Vessels extend in a concentric pattern to the retina edge. The optic nerve head (ONH) is located in the center of the retina; (7B) Vascular remodeling near the ONH takes place between P5 and P8; (7C) Illustration of vascular sprouting into deeper layers of the retina. Vessels extend sprouts to the outer plexiform layer (OPL) and form a plexus. Later spouts arise between the NFL and OPL layers, eventually giving rise to the inner plexiform layer (IPL); (7D) Quantification of vascular density; total pixel count from 12 representative images from 4 treated retinas of each condition. *p=0.006; **p<0.0001; Student's t test; (7E) Quantification of vascular extension, measured by the ratio of the distance from the ONH to the edge of the vasculature, over the distance from the ONH to the edge of retinal cup. 12 representative measurements were taken from 4 treated retinas.
Figure 7B:
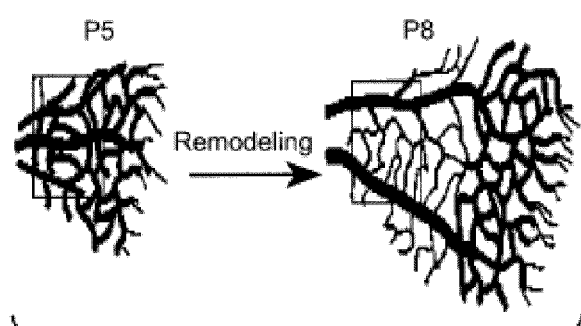
Figure 7C:
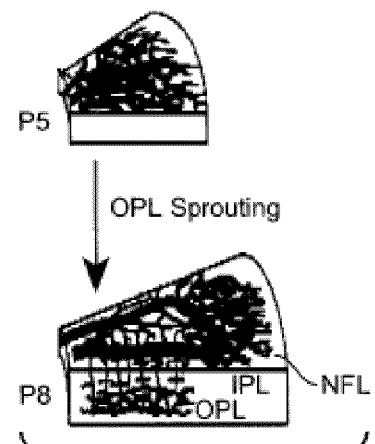

Phenotypes observed in the Nrp1 knock-out mice are consistent with a defect in vascular remodeling. Gu et al. (2003) *Dev Cell* 5:45-57; Kawasaki et al. (1999) *Development* 126: 895-4902; Takashima et al. (2002) *Proc Natl Acad Sci USA* 99:3657-3662. Next, the role of NRP1 in vascular remodeling was tested by analyzing the effects of systemic treatment with the anti-NRP1 mAbs on the developing mouse retina, which is an ideal model to investigate the stereotyped events of vascular sprouting, remodeling, and maturation. Dorrell and Friedlander (2006) *Prog Retin Eye Res* 25:277-95. At birth, an astrocytic network is in place to guide ECs sprouting from central retinal artery located near the optic nerve head (ONH). After one day of postnatal life (P1) the retinal vasculature has developed a morphogenic furrow in the nerve fiber layer (NFL), lying superficial to the ganglion cell layer, that begins to extend toward the edge of the retina in a concentric pattern, reaching halfway by P5 (FIG. 7A). Over the next three days the furrow continues to extend to the edge of the retina, while the vascular plexus closest to the ONH undergoes stereotyped remodeling, consisting of thinning of the vascular plexus into a refined capillary network in the NFL (FIG. 7B), and sprouting of vessels into deeper layers of the retina (FIG. 7C).

Figure 7D:
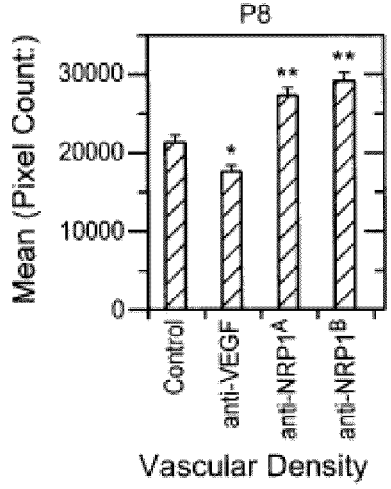
Figure 7E:
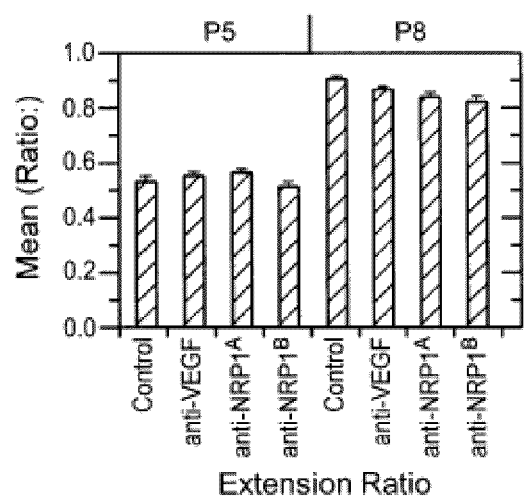

Antibodies were injected into neonatal mice beginning at P1, followed by injections every other day until retinas were collected at P5 and P8. To visualize the vasculature, retinas were stained with isolectin B4 and compared. While the refined capillary network of the IgG control group is well established between P5 and P8, this vascular remodeling is completely inhibited by both anti-NRP1 mAbs. This difference was quantified by comparing the vascular density from representative images taken of the NFL vascular network in regions adjacent to the ONH (FIG. 7D). Because treatment with either anti-NRP1 mAb results in a strong inhibition of vascular remodeling, vascular density is significantly higher in both anti-NRP1$^A$ and anti-NRP1$^B$ treated retinas as compared to controls. Interestingly, the developmental furrow continues to extend in both anti-NRP1 mAb treated retinas, with only a slight inhibition of extension in the anti-NRP1$^B$ treated animals (FIG. 7E). This suggests that development of the retina is not generally inhibited, but that there is instead a specific block in vascular remodeling when treating with either anti-NRP1 mAb.

In contrast to the anti-NRP1 mAbs, anti-VEGF treatment resulted in a reduction of retinal vascular density as compared to control (FIG. 7D). At a qualitative level, vessels in anti-VEGF treated retinas have a reduced complexity at P8, a trend that is present but less obvious at P5. These data suggest that anti-VEGF treatment results in either block of initial sprouting and/or vascular regression. Interestingly, systemic delivery of anti-VEGF does not significantly reduce the extension of the vascular furrow (FIG. 7E). This is likely a consequence of poor antibody diffusion to the extending tip cells due to the lack of vessel lumens in this outer region. Gerhardt et al. (2003) *J Cell Biol* 161:1163-1177.

Evaluating P8 retinas also allowed further investigation of the effects of antibody treatment on angiogenic sprouting. Between P5 and P8, vessels begin to sprout from the NFL vascular network into deeper vascular layers resulting in the formation of the outer plexiform layer (OPL) vascular network, which is superficial to the outer nuclear layer and is the deepest vascular bed in the retina (FIG. 7C). Later in development, sprouting from collaterals that gave rise to the OPL results in an intermediate vascular bead, termed the inner plexiform layer (IPL). Images taken from the OPL at P8 show a complete inhibition of sprouting by both anti-NRP1 mAbs, and by anti-VEGF treatments.

The different phenotypes observed in retinas taken from animals systemically treated with either anti-NRP1$^A$ or anti-NRP1$^B$, as compared to anti-VEGF, suggest that NRP1 may regulate EC function by mechanisms other than enhancing VEGFR2 signaling.

D. Blocking NRP1 Function has Little Effect on VEGFR2 Signaling

Figure 8D:
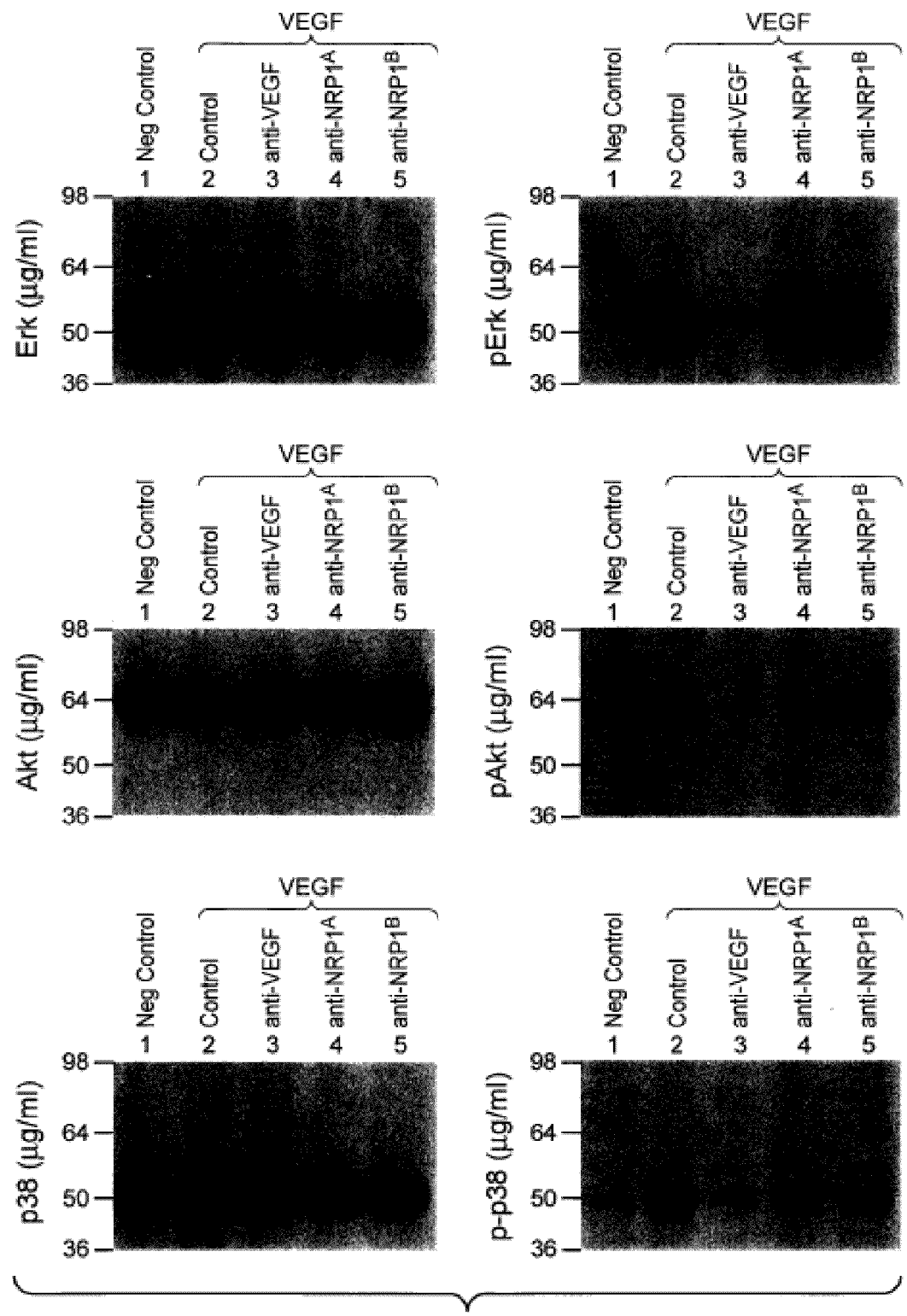
FIG. 8 depicts the effects of anti-NRP1 antibodies on VEGF-induced vascular permeability, HUVEC proliferation, VEGFR2 phosphorylation and VEGFR2 downstream signaling. (8A) Quantification of mouse skin vascular permeability assays. The values showed were the average of 6 independent experiments (p=0.69 for anti-NRP1$^A$, and p=0.989 for anti-NRP1$^B$); (8B) Quantification of HUVEC proliferation in the presence or absence of VEGF (n=5 for each condition); (8C) VEGFR2 phosphorylation level in HUVECs detected by ELISA assay using antibodies that recognized total or tyrosine-phosphorylated VEGFR2. VEGFR2 phosphorylation level in anti-NRP1$^A$ treated cells was not significantly different from the control group (p=0.133). *p=0.00017; Student's t test; (8D) Immunoblot analysis of HUVEC lysates. Cells were treated with the indicated antibodies followed by an incubation with VEGF.

Having observed that NRP1 is required for endothelial cell migration in response to VEGF, we investigated the requirement of NRP1 in EC proliferation and vascular permeability—two defining cellular activities induced by VEGF. Remarkably, treatment with either anti-NRP1$^A$ or anti-NRP1$^B$ had no effect on VEGF-induced permeability, whereas anti-VEGF provided a strong block (FIG. 8A). A similar trend was observed when testing for VEGF-induced EC proliferation, with anti-NRP1$^A$ showing no block of proliferation, and anti-NRP1$^B$ only a slight dose-responsive reduction (FIG. 8B). These results support previously published data showing that siRNA knockdown of NRP1 in ECs does not effect proliferation induced by VEGF (Marga et al. (2005) *Blood* 105:1992-1999), and suggests that NRP1's primary role in VEGF-driven EC behaviors is to mediate cell migration.

The effect of anti-NRP1 antibodies on VEGFR2 signaling was studied. VEGF binds to the second and third extracellular IgG domains of VEGFR2, and activates the receptor by triggering auto-phosphorylation of several tyrosine residues in the intracellular domain. In contrast to anti-VEGF, which completely blocked VEGFR2 phosphorylation induced by VEGF in HUVECs, anti-NRP1$^A$ did not significantly change VEGFR2 phosphorylation levels, whereas anti-NRP1$^B$ resulted in only a modest reduction (FIG. 8C).

Rather than regulating VEGFR2 phosphorylation level directly, NRP1 may act to modulate specific VEGFR2 pathways. To address this possibility, the effect of anti-NRP1 treatment on downstream signaling events mediated by VEGFR2 was examined VEGFR2 has been shown to induce EC proliferation through activation of the mitogen activated protein kinases Erk1/2 (Rousseau et al. (1997) *Oncogene* 15:2169-2177; Takahashi et al. Shibuya (1999) *Oncogene* 18:2221-2230), and to regulate EC survival and vascular permeability through the PI3-Kinase/Akt pathway. Chen et al. (2005) *Nat Med* 11:1188-1196; Gerber et al. (1998) *J Biol Chem* 273:13313-13316; Six et al. (2002) *FEBS Lett* 532:67-69. Consistent with the observation that anti-NRP1 mAb treatments did not significantly change VEGF-induced EC proliferation or vascular permeability, anti-NRP1$^A$ and anti-NRP1$^B$ incubation did not affect VEGF-induced phosphorylation of Erk1/2 or Akt. On the other hand, inhibiting NRP1 function with anti-NRP1 antibodies strongly reduced EC migration. It is possible that NRP1 specifically regulates VEGFR2 pathways required for cell motility, such as the p38 MAP kinase pathway, which has been shown to be required for VEGF-driven actin reorganization and cell migration in ECs. Rousseau et al. (1997) *Oncogene* 15:2169-2177. Anti-NRP1$^A$ and anti-NRP1$^B$ treatments both led to a slight reduction in p38 phosphorylation level in HUVECs (FIG. 8D), lending support to this hypothesis. However, the mild decrease in p38 phosphorylation alone is unlikely to account for the strong reduction we observed in the migration and sprouting assays as described in previous sections (FIG. 6), or explain the qualitatively different phenotypes observed between the anti-NRP1 mAbs and anti-VEGF mAb treatments in the retinal vascular remodeling experiments (FIG. 7).

Example 3

Tumor Inhibitory Activities of Anti-NRP1 Antibodies

Materials and Methods

The human cell lines, H1299 and SK-MES-1 non-small-cell lung carcinomas were obtained from ATCC (Rockville, Md.). For SK-MES-1, each HRLN female nude mouse received a 1 mm$^3$ tumor fragment s.c. implant in the flank. For H1299, 1×10$^7$ tumor cells were injected s.c. in the flank of HRLN female nude mice. Tumor growth was monitored twice weekly by caliper measurements. When tumors reach an average size of 80-120 mm$^3$, mice were sorted to give nearly identical group mean tumor sizes, and treatment was started. This was considered day 1 of each study. All treatments were body-weight adjusted at 0.2 ml/20 g. Tumor volume (mm$^3$)=width$^2$×length/2. Percent tumor growth inhibition (% TGI)=(median tumor volume of the control arm−median tumor volume of the treatment arm/median tumor volume of the control arm)×100. % TGI is only measured as long as all animals remain on they study (for SK-MES-1=day 22; for H1299=day 15). Time to endpoint (TTE)=log$_{10}$ (endpoint volume, mm$^3$)−b/m; were b is the intercept and m is the slope of the line obtained by linear regression of the log-transformed tumor growth data. Percent tumor growth delay (% TGD)=(median TTE for a treatment arm−median TTE for the control arm/median TTE for the control arm)×100.

Mice were anesthetized with Avertin (1.3% tribromoethanol and 0.8% amyl alcohol; Sigma-Aldrich). FITC-labeled *Lycopersicon esculentum* lectin (150 µg in 150 µl of 0.9% NaCl; Vector Laboratories) was injected i.v. 3 minutes before systemic perfusion. The vasculature was perfused transcardially with 4% paraformaldehyde (PFA) in PBS for 2 to 3 min. Tumors were removed and post-fixed by immersion in the same fixative for 16 hrs, followed by an incubation in 30% sucrose overnight for cryoprotection, then embedded in OCT and frozen. Sections (30 µm) were cut and mounted onto glass slides, rehydrated and blocked in PBSt (PBS, 0.5% Triton X-100) with 5% normal goat serum for 2 hrs at room temperature. The sections were incubated overnight with anti-NRP1$^B$ (1:500) or rat anti-mouse PDGFRβ (1:1000; clone APB5, eBioscience) at 4° C. Sections were then washed 4 times in PBSt, and incubated with secondary antibodies, Alexa 488 goat anti-human IgG and Alexa 568 goat anti-rat IgG (1:200; Molecular Probes), for 4 hrs at room temperature. After staining was completed, sections were washed 4 times in PBSt, post fixed with 4% PFA in PBS, followed by another 4 washes in PBS. The final wash solution was removed, and 1-2 drops of Fluoromount-G (SouthernBiotech) were added. Glass coverslips were placed over samples, and images were captured with a Zeiss Axiophot fluorescence microscope.

Results

Blocking the VEGF pathway has been proven to reduce neovascularization in mouse tumor models and in human cancers. Ferrara and Kerbel (2005) *Nature* 438:967-974. However, it is believed that some tumors are less dependent on VEGF for vessel formation, or may become insensitive to anti-VEGF therapies. Jain et al. (2006) *Nat Clin Pract Oncol* 3:24-40; Kerbel et al. (2001) *Cancer Metastasis Rev* 20:79-86. To determine if NRP1 blockade could enhance the tumor growth inhibition provided by blocking VEGF, we selected several xenograft models known to exhibit varying sensitivity to anti-VEGF therapy. Since mouse stromal VEGF, in addition to tumor derived VEGF, has been shown to impact tumor growth, we used anti-VEGF mAbs that recognize both murine and human VEGF. Liang et al. (2006) *J Biol Chem* 281:951-961.

Figure 9A:
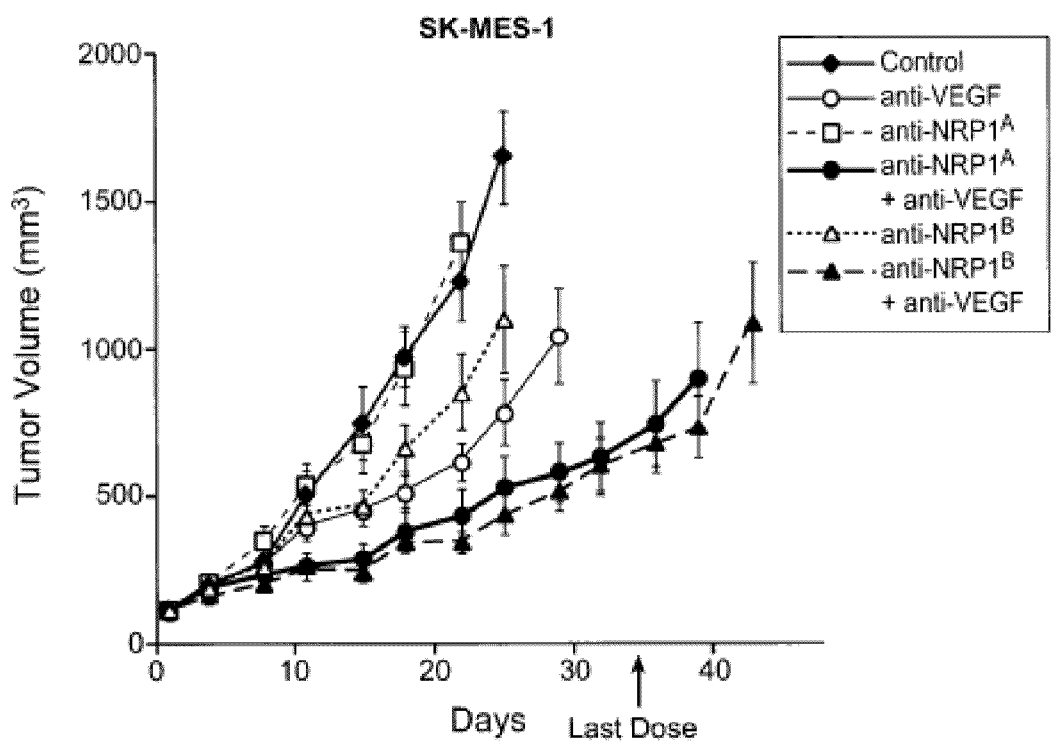
FIG. 9 illustrates tumor growth inhibition effects by anti-NRP1 antibodies (either alone or in combination with anti-VEGF) in various xenograft tumor models. (9A-C) Mean tumor volume graphs of the SK-MES-1, H1299 and Fo5 tumor models, respectively. (9D) Kaplan-Meier plot for the SK-MES-1 tumor model.

These experiments were designed to test the effect of blocking NRP1 alone and in combination with anti-VEGF. Also included were single agent anti-VEGF and isotype control antibody. SK-MES-1 is a NSCLC xenograft model that expresses NRP1 primarily in vascular and stromal tissue, with an intermediate level of expression in tumor cells. In this model, anti-VEGF provided a 52% tumor growth inhibition (TGI), single agent anti-NRP1$^B$ caused a 37% TGI, and anti-NRP1$^A$ had no significant effect on TGI (FIG. 9A).

Figure 9B:
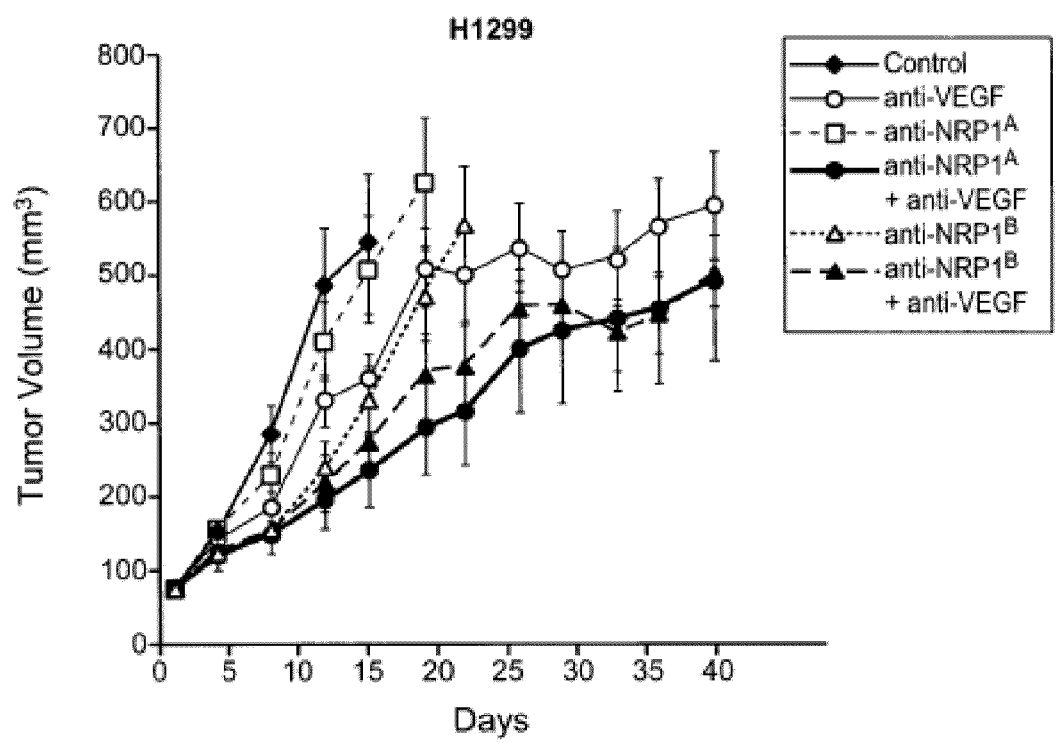
Figure 9C:
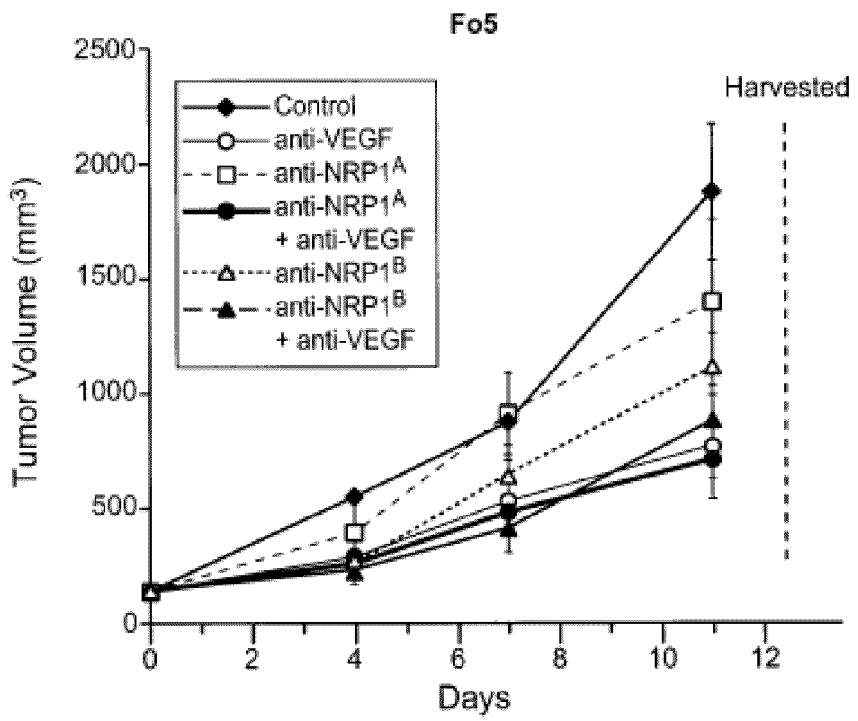
Figure 9D:
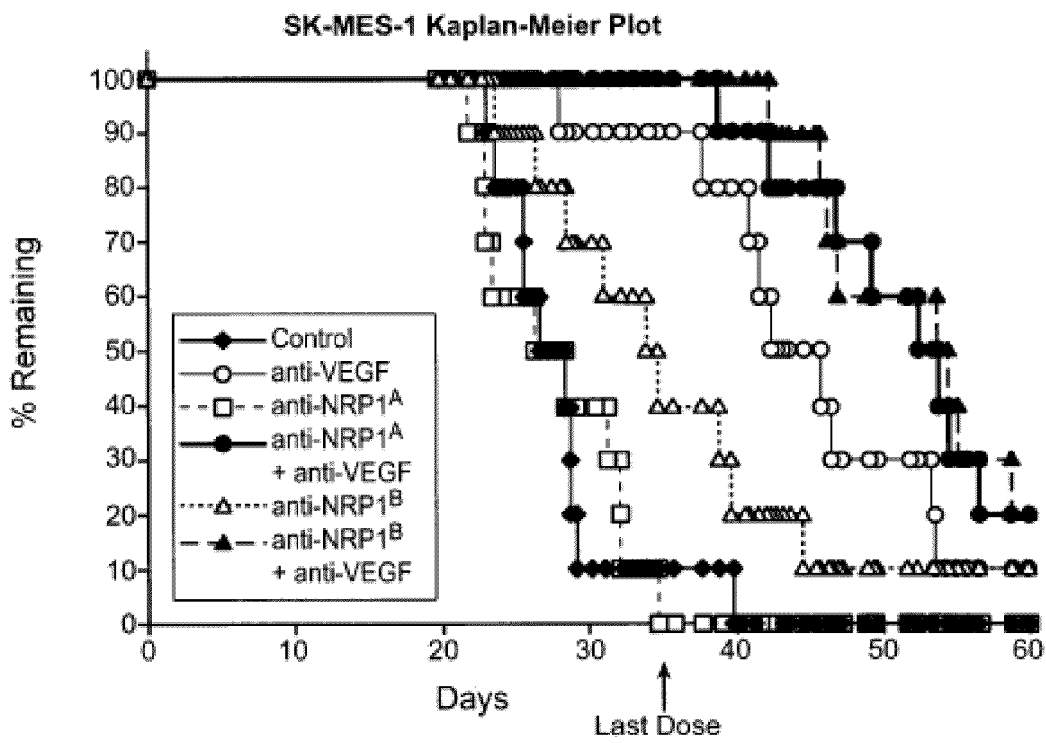
Figure 10A:
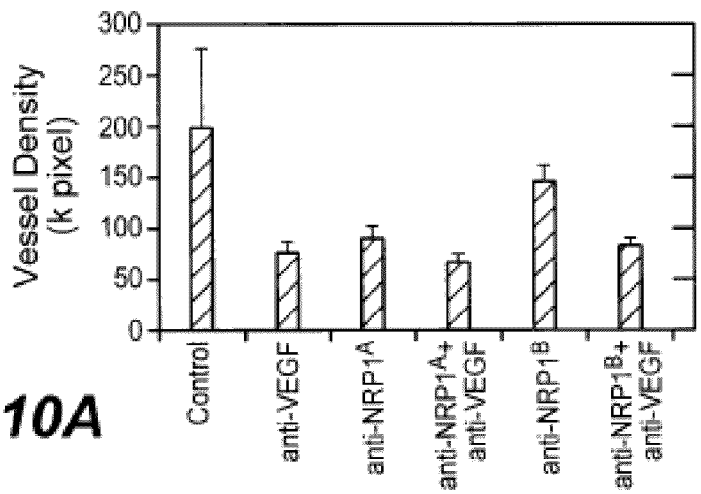
FIG. 10 shows vascular effects by anti-NRP1 antibodies (either alone or in combination with anti-VEGF) in a Fo5 tumor model. (10A) Mean vascular density (measured by lectin perfusion); total pixel count from 3-4 treated tumors of each condition. (10B) Mean perictye density (measured by PDGFRβ staining) (10C) Pericyte/vascular ratio measuring relative pericyte coverage.

Strikingly, the additive effect was observed when either anti-NRP1 antibody was used in combination with anti-VEGF. As depicted in FIG. 10A, anti-NRP1$^A$ used in combination with anti-VEGF increased the TGI from about 52% to about 70%; and anti-NRP1$^B$ used in combination with anti-VEGF increased the TGI to about 77% (FIG. 9A). Similar results were obtained in the H1299 NSCLC xenograft model, which also expresses NRP1 in vascular and stromal tissue at high levels, but in tumor cells to a lesser extent. Single agent anti-NRP1$^B$ showed 39% TGI, anti-VEGF showed 28% TGI, and the combination showed 51% TGI (FIG. 9C).

Animals in the SK-MES-1 model were dosed to day 35 and followed to day 60 to examine the delay in tumor growth (animals were removed from the study when tumor sizes exceeded 1500 mm$^3$; no animals were removed as a result of toxicity). The Kaplan-Meier plot shows a significant effect of both anti-NRP1 mAb combination arms in delaying tumor growth as compared to single agent arms (FIG. 9B). Measurements of tumor growth delay (TGD) show no single agent delay for anti-NRP 1$^A$; 24% TGD for anti-NRP1$^B$; 60% TGD for anti-VEGF; 93% TGD for anti-NRP1$^A$+anti-VEGF combination arm; and 96% for anti-NRP1$^B$+anti-VEGF combination arm.

Similar results to those seen in the NSCLC models were also observed in a murine model of breast cancer, termed founder 5 (Fo5), in which tumors generated by MMTV-Her2 transgenic expression were dissected and implanted in nude mice. Finkle et al. (2004) *Clin Cancer Res* 10:2499-2511. In this model, NRP1 is primarily expressed on vessels and adjacent stroma, and anti-VEGF is again only partially effective at reducing tumor growth (FIG. 9C). Growth inhibition was similar to that seen in the NSCLC models, however to focus on the histological changes in the context of anti-NRP1 and anti-VEGF treatment, animals were harvested on the same day early in the experiment (dashed line; FIG. 9C).

Using the Fo5 model for vascular histology studies, we observed that control tumors showed very large unorganized vessels that generally lack pericyte coverage as determined by PDGFR-β immunohistochemistry. Treatment with anti-VEGF alone resulted in a decrease in vessel diameter and a general reduction in vascular density. In addition, most, if not all vessels that remained in anti-VEGF treated tumors showed close association of pericytes. Similar results were observed with other pericyte markers.

Vessels from tumors treated with either anti-NRP1 mAb alone appear similar in morphology to anti-NRP1 treated vessels in neonatal mouse retinas, with vessels appearing flat and unorganized, maintaining a plexus-like appearance. On the other hand, similar to control treated tumor vessels, tumors treated with either anti-NRP1 mAb also lack significant pericyte coverage. Most interestingly, tumors that were treated with anti-VEGF and either anti-NRP1$^A$ or anti-NRP1$^B$, showed a combined phenotype, with vessel reduction similar to anti-VEGF treated tumors, but with remaining vessels appearing less refined and lacking close pericyte association.

Figure 10B:
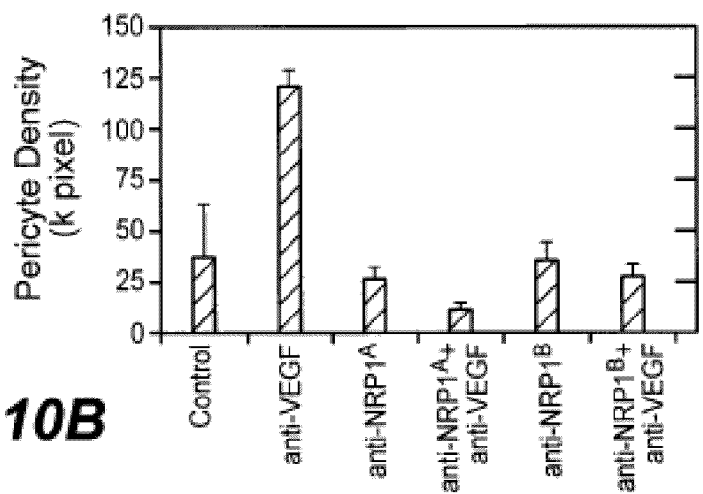
Figure 10C:
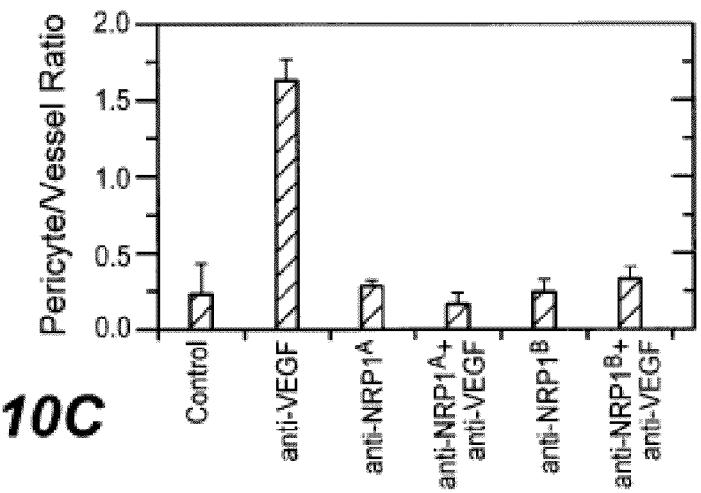

These morphological observations are correlated with the quantified changes in vascular desensity. As shown in FIG. 10, treatment with both anti-NRP1 antibodies and anti-VEGF decreased vascular density (10A). On the other hand, only anti-VEGF seems to increase perictye staining in tumor samples tested, as compared to control. Overall, pericyte/vascular ratio measuring relative pericyte coverage shows that anti-VEGF treated tumors had the highest ratio, which is decreased by anti-NRP1$^A$ and anti-NRP1$^B$ treatment.

The findings that anti-NRP1 (anti-NRP1$^A$ and anti-NRP1$^B$) and anti-VEGF may be acting by blocking different EC functions and/or signaling pathways raised the possibility that combining these antibodies in tumor models could have an additive or synergistic effect in reducing tumor growth. Indeed, a profound additive effect was observed when combining anti-NRP1 with anti-VEGF (FIG. 9). Especially in the case of anti-NRP1$^A$, the results suggest a synergistic, rather than additive effect, since in multiple tumor models the mean tumor volume following single agent anti-NRP1$^A$ treatment was not different from control, but the antibody significantly enhanced tumor response when combined with anti-VEGF, compared to anti-VEGF treatment alone.

In the case of anti-NRP1$^B$, single agent treatment resulted in a significant reduction in tumor growth. Interestingly, these effects are only slightly less potent than anti-VEGF alone. However, the reduction in tumor growth from the combination arms for anti-NRP1$^B$ was similar to the anti-NRP1$^A$ combination arms. The single agent effect of anti-NRP1$^B$ may be due to its relatively stronger inhibitory activity in reducing sprouting and in vivo angiogenesis, compared to anti-NRP1$^A$. On the other hand, both antibodies were equally potent in blocking vascular remodeling in the mouse retinal development assay and inhibiting pericyte association with vessels in the Fo5 tumor model.

It has been proposed that vascular remodeling in the retina takes place in the absence of close pericyte associations, suggesting that pericytes serve to stabilize immature blood vessels ending the plasticity period of vessel remodeling. Benjamin et al. (1998) *Development* 125:1591-1598. Findings of this invention suggest that NRP1 is required for this intricate process of vessel remodeling, consisting of the morphogenesis of the vascular plexus into fine capillaries, followed by further maturation.

The idea of pericytes stabilizing tumor vessels, thus giving rise to anti-VEGF therapy resistance as a consequence of vessels losing their VEGF-dependence, has been proposed and tested experimentally. Bergers et al. (2003) *J Clin Invest* 111:1287-1295; Erber et al. (2004) *Faseb J* 18:338-340. In these studies, it was observed that blocking both the function of VEGF (EC ligand) and PDGF (pericyte ligand) results in further disruption of tumor vasculature. Subsequently, it has been shown in imaging studies that blocking VEGF function alone in tumors results in a significant amount of vascular regression, but the remaining vessels become "normalized" with close pericyte associations, possibly a consequence of immature vessels undergoing vascular remodeling and maturation. Inai et al. (2004) *Am J Pathol* 165:35-52.

Based on the observations obtained in the developing retina, it can be postulated that blocking NRP1 function in tumors would also reduce vascular remodeling of tumor vessels, subsequently inhibiting vessel maturation, therefore keeping vessels in a state of VEGF-dependence. This alone may not have a significant effect on reducing tumor growth, as most tumor vessels are already inherently disorganized. Baluk et al. (2005) *Curr Opin Genet Dev* 15:102-111. This prediction is consistent with the observation that, although anti-NRP1$^A$ strongly inhibits vascular remodeling, we do not see a single agent effect with this antibody in reducing tumor growth. However, it was speculated that blocking vascular remodeling, and the subsequent maturation, in combination with anti-VEGF therapy may render the remaining tumor vessels more susceptible to regression. The experiments of the present invention showed that vessels remaining in tumors treated with either anti-NRP1 mAb in combination with anti-VEGF indeed lack pericyte association. These results suggest that the additive effect we observe in blocking both NRP1 and VEGF function may arise as a consequence of rendering remaining vessels in anti-VEGF treated tumors more vulnerable to regression.

Figure 11A:
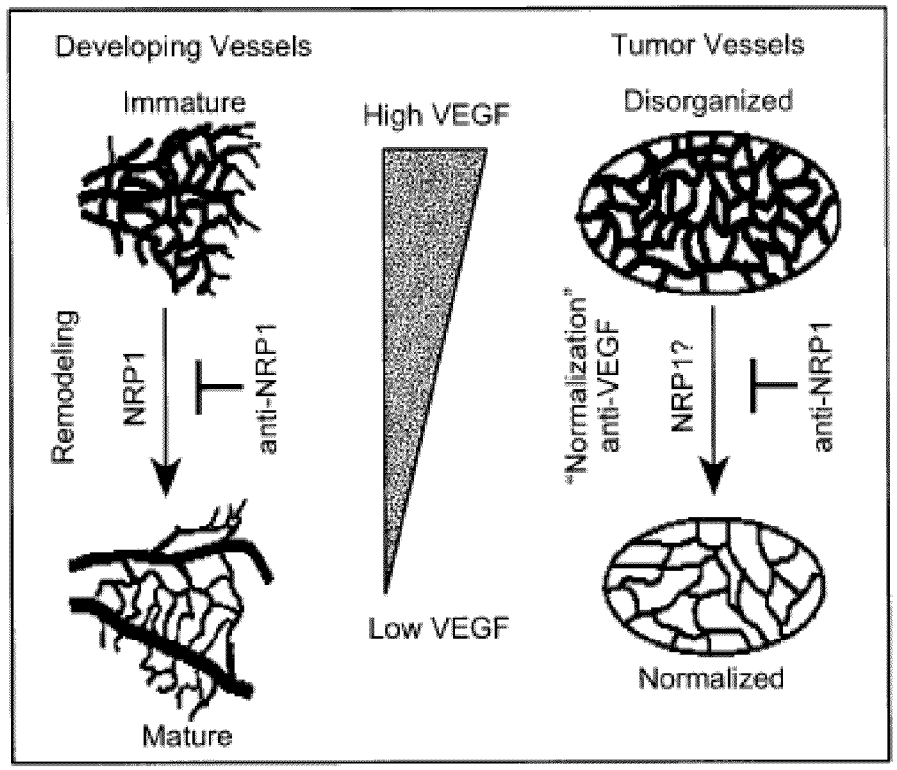
FIG. 11 illustrates addictive effect of NRP1 and VEGF inhibitions on vascular remodeling. 11A presents a model in which blocking NRP1 function in newly formed vessels inhibits vessels from undergoing remodeling and subsequent maturation, rendering vessels dependent on VEGF for survival. 11B shows mean vascular density changes in neonate mice retina in the presence of anti-NRP1B, anti-VEGF or the combination thereof.
Figure 11B:
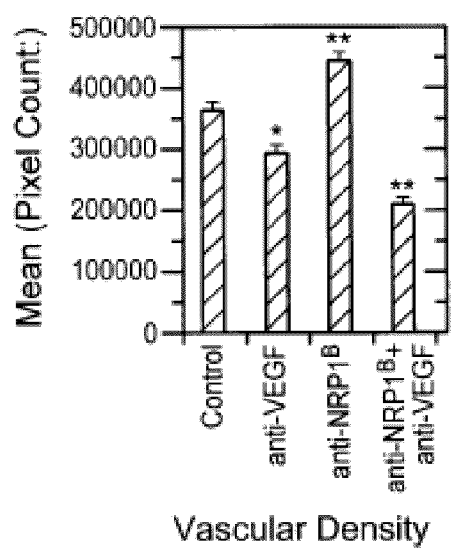

Based on the results obtained in developing retina and xenograft tumor models, it is postulated that blocking NRP1 function in newly formed vessels inhibits vessels from undergoing remodeling and subsequent maturation, thus rendering these vessels more dependent on VEGF for survival (see the model in FIG. 11A). Consistent with this model, we observed a significant decrease in vascular density of the developing retina in neonate mice treated with both anti-NRP1$^B$ and anti-VEGF at half the dose of single agent alone (single dose=10 mg/kg, combination dose=5 mg/kg of each antibody). See FIG. 11B, as compared to FIG. 7D.

Moreover, it is possible that NRP1 may also be required not only for endothelial but also pericyte function. It has recently been reported that bFGF induces upregulation of NRP1 on smooth muscle cells, resulting in the ability of VEGF to induce smooth muscle cell migration. Liu et al. (2005) *Cytokine* 32:206-212. In the present experiment, expression of NRP1 was seen on human smooth muscle cells, as well as on pericytes in various murine and human tumors (for example, expression of NRP1 extends to areas adjacent to lectin positive stain in the Fo5 model).

In conclusion, the experiments described herein demonstrate that blocking NRP1 and VEGF function in tumor models results in an additive effect in reducing tumor growth. Also presented are evidences that NRP1 may also be acting through mechanisms other than VEGFR2 signaling.

What is claimed is:

1. A method for treating a mammal suffering from a disorder associated with pathological angiogenesis comprising administering an anti-neuropilin-1 (NRP1) antibody capable of inhibiting at least one neuropilin (NRP) mediated biological activity, which comprises a light chain variable domain comprising the following CDR amino acid sequences: CDRL1 (RASQSISSYLA; SEQ ID NO:123), CDRL2 (GASSRAS; SEQ ID NO:124) and CDRL3 (QQYMSVPIT; SEQ ID NO:125).

2. The method of claim 1, wherein the antibody comprises a light chain variable domain sequence of SEQ ID NO: 3.

3. The method of claim 1, wherein the antibody comprises a heavy chain variable domain comprising the following CDR amino acid sequences: CDRH1 (GFSFSSEPIS; SEQ ID NO:126), CDRH2 (SSITGKNGYTYYADSVKG; SEQ ID NO:127) and CDRH3 (WGKKVYGMDV; SEQ ID NO:128).

4. The method of claim 3, wherein the antibody comprises a heavy chain variable domain sequence of SEQ ID NO: 4.

5. The method of claim 1, wherein the antibody comprises a light chain variable domain sequence of SEQ ID NO:3 and a heavy chain variable domain sequence of SEQ ID NO:4.

6. The method of claim 1, wherein the antibody is a bispecific antibody.

7. The method of claim 6, wherein the bispecific antibody also binds to hVEGF.

8. The method of claim 7, wherein the portion of the antibody that binds to hVEGF is capable of binding to the same VEGF epitope as the antibody A4.6.1.

9. The method of claim 1, wherein the disorder is a cancer.

10. The method of claim 9, wherein the cancer is selected from the group consisting of breast cancer, colorectal cancer, non-small cell lung cancer, renal cancer, prostate cancer, liver cancer, head and neck cancer, melanoma, ovarian cancer, and mesothelioma.

11. The method of claim 10, wherein the treatment further comprises a second therapeutic agent.

12. The method of claim 11, wherein the second therapeutic agent is an agent selected from the group consisting of an anti-angiogenic agent, an anti-neoplastic composition, a chemotherapeutic agent and a cytotoxic agent.

13. The method of claim 12, wherein the anti-angiogenic agent is a VEGF antagonist.

14. The method of claim 13, wherein the VEGF antagonist is an anti-hVEGF antibody.

15. The method of claim 14, wherein the anti-hVEGF antibody is capable of binding to the same VEGF epitope as the antibody A4.6.1.

16. The method of claim 15, wherein the anti-hVEGF antibody is bevacizumab or ranibizumab.

17. The method of claim 12, wherein the second therapeutic agent is a receptor tyrosine kinase inhibitor selected from the group consisting of vatalanib (PTK787), erlotinib (TARCEVA®), OSI-7904, ZD6474 (ZACTIMA®), ZD6126 (ANG453), ZD1839, sunitinib (SUTENT®), semaxanib (SU5416), AMG706, AG013736, Imatinib (GLEEVEC®), MLN-518, CEP-701, PKC-412, Lapatinib (GW572016), bortezomib (VELCADE®), AZD2171, sorafenib (NEXAVAR®), XL880, and CHIR-265.

18. The method of claim 1, wherein the mammal is a human.

* * * * *